US012712055B1

(12) United States Patent
Egger et al.

(10) Patent No.: US 12,712,055 B1
(45) Date of Patent: Aug. 18, 2026

(54) AUTOMATED SELECTION AND DELIVERY OF ONLINE MENTAL HEALTHCARE AND OTHER THERAPEUTIC SERVICES USING COMPARISON OF MATCHED PAIRS OF GROUPS TO IMPROVE MODE AND DELIVERY OF SERVICES AND EVALUATE INDIVIDUAL PROVIDER PERFORMANCE

(71) Applicant: Little Otter, Inc., San Francisco, CA (US)

(72) Inventors: Rebecca E. Egger, Durham, NC (US); Helen Link Egger, Durham, NC (US); Daniel Egger, Durham, NC (US); Elsa A. Friis, Durham, NC (US); R. Maximillian Helzberg, San Geronimo, CA (US); Jim Inoue, Seattle, WA (US)

( * ) Notice: Subject to any disclaimer, the term of this patent is extended or adjusted under 35 U.S.C. 154(b) by 173 days.

(21) Appl. No.: 18/180,769

(22) Filed: Mar. 8, 2023

Related U.S. Application Data

(60) Provisional application No. 63/318,247, filed on Mar. 9, 2022.

(51) Int. Cl.
*G16H 10/20* (2018.01)
*G16H 20/70* (2018.01)
*G16H 50/30* (2018.01)

(52) U.S. Cl.
CPC ............. *G16H 10/20* (2018.01); *G16H 20/70* (2018.01); *G16H 50/30* (2018.01)

(58) Field of Classification Search
CPC ......... G16H 10/20; G16H 20/70; G16H 50/30
(Continued)

(56) References Cited

U.S. PATENT DOCUMENTS 9,026,476 B2 5/2015 Bist
10,127,927 B2 11/2018 Kalinli-Akbacak
(Continued)

FOREIGN PATENT DOCUMENTS

JP 2009110490 A 5/2009
KR 20210021782 A * 3/2021 ............. G16H 20/70

OTHER PUBLICATIONS

Primm, Mallory ; Understanding the Lived Experiences of Mental Health Professionals Facilitating Psychodrama Teletherapy Groups; Adler University, ProQuest Dissertations & Theses, 2022. 29392921. (Year: 2022).*

(Continued)

*Primary Examiner* — Hiep V Nguyen
(74) *Attorney, Agent, or Firm* — Aldo Noto, Esq.; Rimon PC

(57) ABSTRACT

The disclosed methods and systems facilitate and deliver online mental healthcare and other therapeutic services to a group of entities (individuals). First, data associated with the group is received. Second, data are analyzed to generate an entity index for one or more entities and an entity pair index for one or more pairs of entities. Third, the entity indexes and the entity pair indexes are used to generate a group network index. The group network index indicates a level of performance of the group. Fourth, a set of interventions are identified using the group network index in combination with its weighted components, based on weights assigned to entity indexes and entity pair indexes. A set of online therapeutic services is associated with the set of interventions. Fifth, the set of online therapeutic services are executed and delivered. Sixth, the level of group performance during or after the execution of some or all of the set of online therapeutic services is compared to a prior value, and changes or additional therapeutic services may be recommended. Seventh, groups can be paired with clinically
(Continued)

and demographically similar groups for purposes of prospective trials to compare modes of treatment, and retrospective analysis of individual service provider performance for quality control.

20 Claims, 41 Drawing Sheets

(58) Field of Classification Search
USPC .............................................................. 705/2
See application file for complete search history.

(56) References Cited

U.S. PATENT DOCUMENTS

| | | | | |
|---|---|---|---|---|
| 10,524,715 | B2 | 1/2020 | Sahin | |
| 10,719,796 | B2 | 7/2020 | Tomoeda | |
| 11,296,971 | B1 * | 4/2022 | Jain | H04L 43/08 |
| 2010/0205541 | A1 * | 8/2010 | Rapaport | G06Q 30/02<br>715/753 |
| 2017/0220651 | A1 * | 8/2017 | Mathew | G06F 16/285 |

OTHER PUBLICATIONS

Jingfang Liu and Jiayu Wang; Users' Intention to Continue Using Online Mental Health Communities: Empowerment Theory Perspective; Int. J. Environ. Res. Public Health 2021, 18, 9427. https://doi.org/10.3390/ijerph18189427 (Year: 2021).*

* cited by examiner

AUTOMATED SELECTION AND DELIVERY OF ONLINE MENTAL HEALTHCARE AND OTHER THERAPEUTIC SERVICES USING COMPARISON OF MATCHED PAIRS OF GROUPS TO IMPROVE MODE AND DELIVERY OF SERVICES AND EVALUATE INDIVIDUAL PROVIDER PERFORMANCE

RELATED APPLICATIONS

This application claims priority to provisional patent application 63/318,247, filed Mar. 9, 2022, entitled “Platform for Remote Assessment and Intervening to Improve Group Function,” the content of which is hereby incorporated herein by reference in its entirety.

FIELD OF INVENTION

The invention relates to delivery of online mental healthcare and other online therapeutic services.

BACKGROUND

In the United States, in any given year, about 20% of the adult and adolescent population is experiencing a mental illness and, in a recent poll, 90% of the population responded that the United States is in a mental health crisis. About 75 million children under 18 live in about 60 million American families. Tens of millions of these families suffer from an impairing mental health disorder, and the current mental health service delivery paradigm is failing these families.

Three factors cause this systematic failure: assessment and treatment of individuals in isolation from their families; arbitrary selection of modes of care; and total lack of quality control.

Assessment and Treatment of Individuals in Isolation From their Families

Under the present mental health paradigm, individual people (also referred to as “entities” in this document) are assessed and treated for mental health problems as if they lived in isolation. In fact, when one member of a family is sick, all are impacted. For example, improving the mental health of a parent will reduce mental health symptoms and distress for their children; improving the mental health of a child will reduce mental health symptoms and distress for their parents. Too often, an individual, whether adult or child, is assessed and offered treatment as an individual alone, ignoring the fact that their problems have contributing causes that could be addressed by offering help to one or more other family members. Contributing causes also lie in distressed relationships within the family. Mental health is about more than individuals; it must consider relationships.

What is needed is a system to address mental health at the level of the family, delivering interventions to the individuals within the family who need it most, and to the relationships within the family that are most in need of support. Consider an example of an intervention to address a relationship, that has the effect of improving the mental health of an individual. Providing co-parent counselling to a separated or divorced couple, to assist them in communication and shared decision-making, could be the single most effective intervention to improve their child’s mental health. And it might be the most effective intervention to improve the family’s overall wellbeing as well. What is needed is a system that views families as emergent networks with properties of their own, directing therapeutic interventions so that the family as a whole obtains the greatest benefit.

Arbitrary Selection of Modes of Care

Under the present system, mental health service providers generally operate independently, delivering whatever mode of care that they are trained and licensed to offer. No attempt is made to determine and deliver the mode of intervention(s) that would be optimal in a given situation. The lack of informed selection in delivery of mental health services inevitably results in arbitrary delivery of inappropriate, ineffective, sub-optimal, and even counter-productive care. For example, individuals whose mental illness has a physical cause that can only be cured by medical intervention often spend months or years receiving ineffective interventions before receiving appropriate medical treatment.

What is needed is a system that delivers the optimal mode of care. For example, while more than one type of intervention may be effective in treating anxiety disorder (for example, cognitive behavioral therapy (CBT) and Eye Movement desensitization and reprocessing (EMDR) could both help), what is needed is a system that, for a particular patient’s circumstances, identifies and delivers the optimal mode of care, providing the greatest reduction in impairing symptoms in the shortest time. Furthermore, recognizing that optimization is an ongoing process, what is needed is a statistically valid way to test newly-developed modes of care against the best currently available alternatives.

Total Lack of Quality Control

Under the present system, mental healthcare service providers cannot be assessed for competence and outcomes. Different providers delivering the same mode of care show dramatically different rates of success. No effort is made to determine the actual reasons for these disparities and to address them. Quality control is utterly lacking.

What is needed is a system that allows for statistically valid comparisons of outcomes and efficiency between service providers who offer the same mode of care, so that across groups of providers, significantly inferior and superior performance can be identified and overall quality continually improved.

SUMMARY

In one embodiment of the present disclosure, a method for facilitating online therapeutic services to a group of entities is provided. The method includes receiving, by a server, data associated with a group of entities. Further, the method includes analyzing, by the server, the data associated with the group of entities to generate an entity index for each entity and an entity pair index for each pair of entities in the group of entities. Furthermore, the method includes generating, by the server, a group network index based on the entity index and the entity pair index. In one embodiment, the group network index indicates a level of performance of the group of entities. The method further includes identifying, by the server, a set of interventions using an optimization technique based on the value of the group network index, the entity index and/or entity pair index. Subsequently, the method includes recommending, by the server, a set of online therapeutic services associated with the set of interventions. Further, the method includes executing, by the server, the set of online therapeutic services to improve the level of performance of the group of entities. Finally, the method includes monitoring, by the server, the level of performance during the execution of the set of online therapeutic services for a definite time period, thus, facilitating and providing online therapeutic services to the group of entities to improve performance.

Additionally, or optionally, the method further includes recommending, by the server, a subset of online therapeutic services, from the set of online therapeutic services, to be executed for one or more entities from the group of entities until the group network index reaches a defined target value.

Additionally, or optionally, the set of online therapeutic services correspond to at least one of physical therapy sessions, medical consultations, psychotherapy sessions, and remote training sessions for the one or more entities.

Additionally, or optionally, the set of interventions are identified by analysis of the data using a training set of interventions stored in a training model.

Additionally, or optionally, the level of performance is monitored based on at least one of a value of change in the group network index, the value for change with respect to elapsed time required for the change in the group network index, and intervention cost for the change in the group network index.

Additionally, or optionally, the data comprises at least one of demographic information, health information, behavioral information, emotion recognition information, and interaction information associated with each entity and each pair of entities present in the group of entities.

Additionally, or optionally, the interaction information comprises types of interactions happening within the group of entities, and a frequency of interactions.

Additionally, or optionally, the group network index is at least one of numeric, qualitative, and ordinal categorical.

Additionally, or optionally, the entity index, the entity pair index, and the group network index are timestamped. In one embodiment, the timestamped group network index is generated based on the timestamped entity index, the timestamped entity pair index, a weight associated with each timestamped entity index, and a weight associated with each entity pair index.

Additionally, or optionally, the set of online therapeutic services is recommended upon triaging based on the timestamped entity index, the timestamped entity pair index, and the timestamped group network index. In one embodiment, the set of online therapeutic services are prioritized based on the timestamped entity index, the timestamped entity pair index.

Additionally, or optionally, the level of performance is monitored based on a difference between the timestamped group network index at different time instances.

Additionally, or optionally, the method further includes comparing the timestamped group network index of two or more groups of entities, to allocate on-line therapeutic services across different groups based on urgency.

In another embodiment of the present disclosure, a system for facilitating online therapeutic services to a group of entities is provided. The system includes circuitry configured to receive data associated with a group of entities. The circuitry is further configured to analyze the data associated with the group of entities to generate an entity index for each entity and an entity pair index for each pair of entities in the group of entities. Further, the circuitry is configured to generate a group network index based on the entity index and the entity pair index. In one embodiment, the group network index indicates a level of performance of the group of entities. Furthermore, the circuitry is configured to identify a set of interventions using an optimization technique based on the value of the group network index, the entity index and/or entity pair index. Subsequently, the circuitry is configured to recommend a set of online therapeutic services associated with the set of interventions. The circuitry is further configured to execute the set of online therapeutic services to improve the level of performance of the group of entities. Finally, the circuitry is configured to monitor the level of performance during and after the execution of the set of online therapeutic services for a definite time period, thus, facilitating improved delivery of online therapeutic services to the group of entities.

In yet another embodiment of the present disclosure, a method for facilitating online therapeutic services to improve performance of a group of entities is disclosed. The method includes receiving, by a server, data associated with a group of entities. Further, the method includes sorting, by the server, the data into entity data and pairwise data based on an analysis of the data. In one embodiment, the entity data is associated with each entity present in the group of entities, and the pairwise data is associated with pairs of entities present in the group of entities. In some embodiments, pairwise data may not exist for one or more pairs of entities. Furthermore, the method includes generating, by the server, a timestamped entity index associated with each entity and a timestamped entity pair index for each pair of entities based on the sorted data. The method further includes generating, by the server, a timestamped group network index associated with a unique group identification based on the timestamped entity index and the timestamped entity pair index. In one embodiment, the unique group identification is assigned to the group of entities. Subsequently, the method includes identifying, by the server, a set of interventions associated with the group of entities based on the timestamped group network index, the timestamped entity index, and/or the timestamped entity pair index. Further, the method includes automatically recommending, by the server, a set of online therapeutic services to the group of entities upon identifying the set of interventions. Furthermore, the method includes executing, by the server, the set of online therapeutic services to improve a level of performance of the group of entities. Finally, the method includes monitoring, by the server, the level of performance of the group of entities based on comparing the group network index with a new group network index. In one embodiment, the new group network index is generated upon execution of the set of online therapeutic services, facilitating future delivery of online therapeutic services to improve the performance of the group of entities.

Various embodiments of the present disclosure provide a method and system for facilitating online delivery of therapeutic services to a group of entities, along with automated performance evaluation and recommendation of further online interventions in a continual process.

DETAILED DESCRIPTION

Figure 1A:
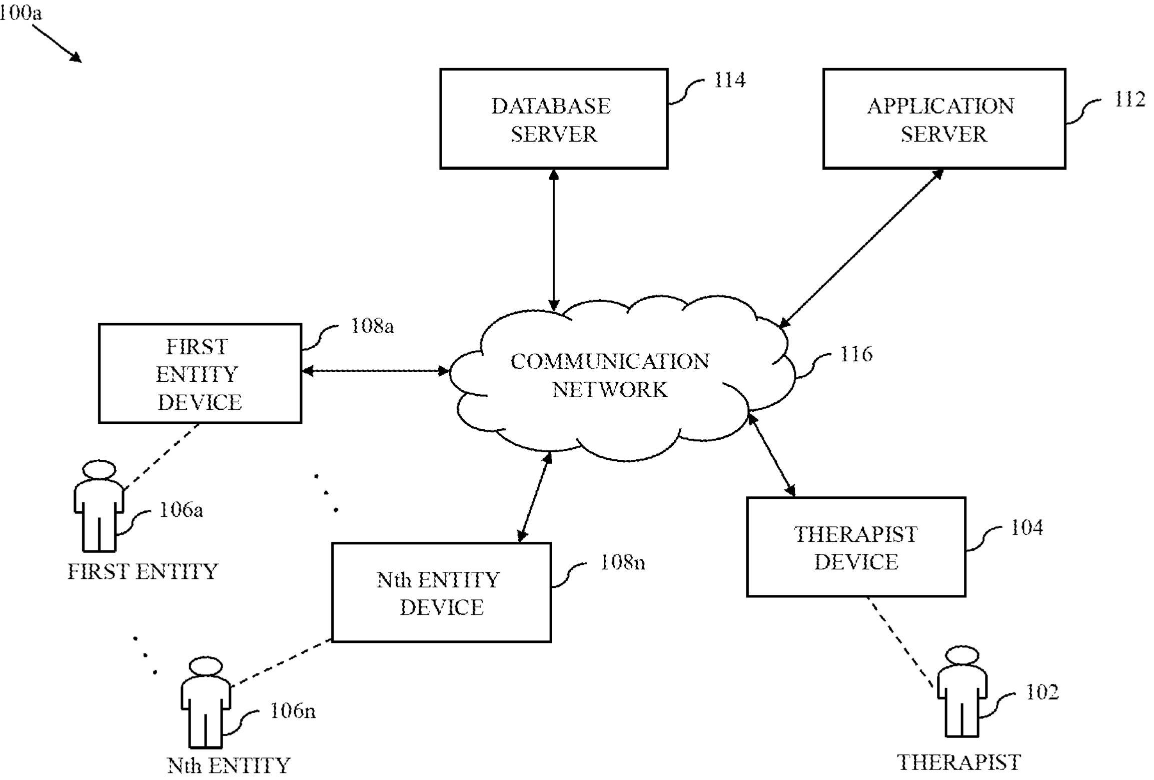
FIG. 1A is a block diagram that illustrates a system architecture of a system for facilitating online therapeutic services to a group of entities, in accordance with an embodiment of the disclosure.

Example apparatus are described herein. Other example embodiments or features may further be utilized, and other changes may be made, without departing from the spirit or scope of the subject matter presented herein. In the following detailed description, reference is made to the accompanying drawings, which form a part thereof.

The example embodiments described herein are not meant to be limiting. It will be readily understood that the aspects of the present disclosure, as generally described herein, and illustrated in the drawings, can be arranged, substituted, combined, separated, and designed in a wide variety of different configurations, all of which are explicitly contemplated herein.

FIG. 1A is a block diagram that illustrates a system architecture 100 of a system for facilitating online therapeutic services to a group of entities (also referred to as individuals), in accordance with an embodiment of the disclosure. The system architecture 100 includes a therapist 102, a therapist device 104, entities 106*a*-106*n* (hereinafter also referred to as "the group of entities"), entity devices 108*a*-108*n*, an application server 112, a database server 114, and a communication network 116.

The group of entities 106*a*-106*n* may include multiple individuals present in a team. In an example, the group of entities corresponds to a family, and also sports teams, groups of military soldiers, corporate teams, groups of scientists or engineers, manufacturing teams, and the like. Further, data associated with the group of entities 106*a*-106*n* is used for analysis of the performance of the group of entities 106*a*-106*n*. The performance of the group of entities 106*a*-106*n* is also referred as the "functioning" of the group of entities 106*a*-106*n*. The group of entities 106*a*-106*n* may be registered on an online service-facilitation platform (also referred to as "performance evaluation platform"). The registration may be initiated, by the group of entities 106*a*-106*n*, by utilizing computing devices, such as the entity devices 108*a*-108*n*, respectively.

Each of the entity devices 108*a*-108*n* may include suitable logic, circuitry, interfaces, and/or code, executable by the circuitry, that may be configured to perform one or more operations. For example, a first entity device 108*a* may be a computing device that is utilized, by a first entity 106*a*, to initiate the one or more operations by means of a service application (associated with the online services facilitating platform and hosted by the application server 112) running on the first entity device 108*a*. For example, the first entity device 108*a* may be utilized, by the first entity 106*a*, to check the analysis and facilitation of online therapeutic services done by the online services facilitation platform. To initiate the facilitation of the online therapeutic services, a registration request may be initiated, by the first entity 106*a*, by utilizing the service application running on the first entity device 108*a*. The first entity 106*a* may further utilize the first entity device 108*a* to capture the data, related to the first entity 106*a*, which is further used to facilitate the online therapeutic services to the group of entities. Various modes of input that may be utilized by the first entity 106*a* to perform the aforementioned functions include, but are not limited to, a touch-based input, a text-based input, a voice-based input, a gesture-based input. Further, the data related to each entity (i.e., a second entity 106*b*, a third entity 106*c* . . . , an $n^{th}$ entity 106*n*) from the group of entities may be transmitted to the application server 112.

For example, the entity devices 108*a*-108*n* may be computing devices that are utilized, by the group of entities 106*a*-106*n*, to initiate the one or more operations by means of a service application (associated with the online service-facilitation platform and hosted by the application server 112) running on the entity devices 108*a*-108*n*. Various functionalities and operations of an $n^{th}$ entity device 108*n* may be similar to functionalities and operations of the first entity device 108*a* as described above. Examples of the entity device 108*a* or 108*n* include, but are not limited to, a personal computer, a laptop, a smartphone, and a tablet computer.

Further, the therapist 102 may be an individual that helps execute interventions associated with the group of entities (i.e., the entities 106*a*-106*n*) based on the performance of the group of entities 106*a*-106*n*. In one example, the therapist 102 may execute (or "deliver") online therapeutic services (also referred to as plans) related to the interventions. The computing device (such as the therapist device 104) may be utilized by the therapist 102 for connecting to the application server 112.

In one embodiment, the therapist 102 may be a performing practitioner for delivering online therapeutic services related to the interventions of the group of entities. In other words, the therapist 102 may be a suitable practitioner for execution of the plans. The therapist 102 may be recommended by the online service-facilitation platform based on the online therapeutic services. In one embodiment, the online service-facilitation platform may analyze information, related to a set of therapists, like a name, a role, years of experience, an expertise, a location, and the like. Further, the online service-facilitation platform may recommend at least one therapist from the set of therapists to the group of entities based on analysis of the information associated with the set of therapists.

The therapist device 104 may include suitable logic, circuitry, interfaces, and/or code, executable by the circuitry, that may be configured to perform one or more operations. In an exemplary embodiment, the therapist device 104 may be a computing device, such as a smartphone, a tablet computer, a laptop, or any other portable computing device. The one or more user interfaces may be received in response to the registration request initiated by the therapist 102.

The application server 112 may include suitable logic, circuitry, interfaces, and/or code, executable by the circuitry, that may be configured to perform one or more operations for facilitating the online therapeutic services to the group of entities. The application server 112 may be a computing device, which may include a software framework, that may be configured to create the application server implementation and perform the various operations associated with the online services facilitating platform. The application server 112 may be realized through various web-based technologies, such as, but not limited to, a Node JS framework, a Java web-framework, a .NET framework, a PHP framework, a python framework, or any other web-application framework. Examples of the application server 112 include, but are not limited to, a personal computer, a laptop, or a network of computer systems. In one embodiment, the application server 112 is implemented as multiple instances of the application server 112 for the group of entities and scalable as per requirement.

In an embodiment, the application server 112 may be configured to process, control, and manage various functionalities and operations such as evaluation initiation, intervention identification, therapeutic services recommendation, therapeutic services execution, and level monitoring. For example, the application server 112 may be configured to receive data, associated with the group of entities, from the entity devices 108*a*-108*n*. The data may comprise identification information, demographic information, health information, behavioral information, emotion recognition information and interaction information associated with each entity present in the group of entities. Upon receiving the data, the application server 112 may analyze the data to generate an entity index for each entity from the group of entities 106*a*-106*n*, and an entity pair index for each pair of entities from the group of entities 106*a*-106*n*. A pair of entities corresponds to a combination of two entities or individuals from the group of entities 106*a*-106*n*. In some embodiments, not all pairs of individuals will have data to generate an entity pair index, and not all individuals will have data to generate an entity index. The application server 112 may be further configured to generate a group network index based on the entity index and the entity pair index. Further, the application server 112 may be configured to identify a set of interventions associated with the group of entities using an optimization technique. Furthermore, the application server 112 may be configured to recommend a set of online therapeutic services associated with the set of interventions. The application server 112 may be configured to execute the set of online therapeutic services to improve the level of performance of the group of entities 106*a*-106*n*. The application server 112 may be further configured to monitor the level of performance of the group of entities 106*a*-106*n* during the execution of the set of online therapeutic services for a definite time period, thus, facilitating subsequent delivery of the online therapeutic services to the group of entities 106*a*-106*n* to improve group performance.

The application server 112 may be further configured to facilitate a subset of online therapeutic services, from the set of online therapeutic services, that needs to be executed for one or more entities from the group of entities 106*a*-106*n* until the group network index reaches a defined value of the group network index. Further, the application server 112 may be configured to compare the timestamped group network index of the group of entities 106*a*-106*n* with a timestamped group network index of another group of entities for allocating the on-line therapeutic services across different groups.

The database server 114 may include suitable logic, circuitry, interfaces, and/or code, executable by the circuitry, that may be configured to perform one or more operations, such as receiving, storing, processing, and transmitting queries, data, or content. The database server 114 may be a data management and storage computing device that is communicatively coupled to the application server 112 to perform the one or more operations. In an exemplary embodiment, the database server 114 may be configured to manage and store training data comprising intervention data and therapeutic services information recommended for the intervention data associated with different group of entities. Further, the training data comprises therapeutic services information associated with the different group of entities performed in the past using the online services facilitating platform. The database server 114 may be configured to receive the training data from the application server 112.

The database server 114 may be further configured to manage and store entity information of each entity (such as the entity 106*a* or 106*n*) and therapist information of each therapist (such as the therapist 102). The entity information of each entity may include at least entity demographic information, entity health information, entity behavioral information, entity emotion recognition information, entity interaction information, and the like. Similarly, the therapist information of each therapist may include at least a therapist name, plans recommended by the therapist, and the like. The entity information may further include an entity device type, and the therapist information further include a therapist device type. In an embodiment, the database server 114 may be configured to generate a data structure including one or more rows and columns for storing the information of the evaluation performed for the group of entities.

In an embodiment, the database server 114 may be configured to receive a query from the application server 112. The query may correspond to an encrypted message that is decoded by the database server 114 to determine a request for retrieving requisite information (such as the entity information, the therapist information, the training data, or any combination thereof). In response to the determined request, the database server 114 may be configured to retrieve and communicate the requested information to the application server 112. Examples of the database server 114 may include, but are not limited to, a personal computer, a laptop, or a network of computer systems.

In operation, the application server 112 receives the data associated with each entity from the group of entities 106*a*-106*n*. The data is timestamped, i.e., a time of receiving the data is recorded. The data is received from the entity devices 108*a*-108*n*. The data comprises demographic information, health information, behavioral information, emotion recognition information, and interaction information associated with each entity present in the group of entities. The demographic information of the group of entities includes at least one of: an entity name, an entity age, an entity hobby, an entity location, and the like. The health information includes at least one of: a medication dosage, a frequency of the medical dosage, a blood pressure, a heart rate, blood tests, a sleep duration, a stress test, and physical activity tracking. The behavioral information includes at least one of: facial expressions, analysis of pauses, speech patterns, interrupting, and body language. The interaction information includes at least one of: types of interactions happening within the group of entities and frequency of interactions happening in the group of entities 106*a*-106*n*. The emotion recognition information includes information related to emotions of the group of entities 106*a*-106*n*. In an embodiment, the data along with the time of receiving the data is stored in the database server 114.

In one embodiment, the data are sorted into entity data and pairwise data. The entity data is associated with each entity from the group of entities 106*a*-106*n*, and the pairwise data is associated with each pair of entities from the group of entities 106*a*-106*n*. In an embodiment, each pair of entities corresponds to combination of two entities, having a relationship, from the group of entities. In one example, assume a family (i.e., the group of entities) of 3 people. The family includes a primary parent, a co-parent, and a child 1. In the example, the three pairs of entities include the primary parent and the co-parent, the primary parent and the child 1, and the co-parent and the child 1.

The pairwise data further comprises relationship data between two entities in each pair of the group of entities. The pairwise data indicate one or more of a quality level, a functioning level, and a stress level in the relationship of the pair of entities. In one embodiment, the pairwise data is received as video feeds. The video feeds are further analyzed to extract the pairwise data associated with each pair of entities. In one example, information like "negative impact of an individual X on a stress level" or "interfering of the individual X with family relationships" is extracted from the video feeds.

In an embodiment, the data is received as the video feeds associated with each entity from the group of entities 106*a*-106*n*. Further, the data associated with the pair of entities is received as video feeds. The video feeds are further processed using a machine learning technique. The machine learning technique analyses the video feeds based on historical data. The historical data comprise facial expressions, emotions, motions, gestures, interaction types associated with each entity and each pair of entities from the group of entities. Based on the analysis, the behavioral information, the interaction information, and the emotion recognition information are extracted from the video feeds. In another embodiment, the data such as the demographic information, and the health information are received as text or a document from the group of entities 106*a*-106*n*. In yet another embodiment, the data is received as an audio feed from the group of entities 106*a*-106*n*. The audio feed is further analyzed using the machine learning technique. Based on the analysis, the behavioral information, the interaction information, and the emotion recognition information are extracted from the audio feed.

In an embodiment, one or more questions are sent to each entity from the group of entities 106*a*-106*n*. Further, answers associated with one or more questions are received from the group of entities 106*a*-106*n*. The answers are further analyzed using artificial intelligence techniques. Based on the analysis, the behavioral information, the interaction information, and the emotion recognition information are extracted from the answers. The artificial intelligence techniques use real-time training data, including behavioral information, interaction information, the emotion recognition information, and the like, for analysis of the answers.

In one exemplary embodiment, the group of entities may be a family comprising six individuals. Further, the application server 112 receives the data associated with each individual (i.e., entity) in the family. Upon receiving, the data is stored as shown in Table 1.

TABLE 1

Example of the data storage categories for a family network.

| Individuals in the Family Network | | | | | | |
|---|---|---|---|---|---|---|
| 1. Primary Caregiver parent | Data on individual (1) | | | | | |
| 2. Child 1 | Data on pairwise relationship (1, 2) | Data on individual (2) | | | | |
| 3. Partner | Data on pairwise relationship (1, 3) | Data on pairwise relationship (2, 3) | Data on individual (3) | | | |
| 4. Co-parent | Data on pairwise relationship (1, 4) | Data on pairwise relationship (2, 4) | Data on pairwise relationship (3, 4) | Data on individual (4) | | |
| 5. Child 2 | Data on pairwise relationship (1, 5) | Data on pairwise relationship (2, 5) | Data on pairwise relationship (3, 5) | Data on pairwise relationship (4, 5) | Data on individual (5) | |
| 6. Child 3 | Data on pairwise relationship (1, 6) | Data on pairwise relationship (2, 6) | Data on pairwise relationship (3, 6) | Data on pairwise relationship (4, 6) | Data on pairwise relationship (5, 6) | Data on individual (6) |
| | (1)-Primary caregiver parent | (2)-Child 1 | (3)-Partner | (4)-Co-parent | (5)-Child 2 | (6)-Child 3 |

Once the data is received, the application server 112 analyses the data of the group of entities 106*a*-106*n*. Based on the analysis, the application server 112 generates an entity index for each entity, and an entity pair index for each pair of entities from the group of entities 106*a*-106*n*. The entity index for each entity is generated based on the data of the entity, i.e., based on the behavioral information, the demographic information, the health information, the interaction information, and the emotion recognition information associated with the entity. The entity index (also referred to as an individual index) of each entity indicates one or more of a performance level, a distress level, or a symptom severity score of each entity in the group of entities 106*a*-106*n*. The entity index is a timestamped entity index, i.e., a time of generation of the entity index is recorded.

Further, the entity pair index (also referred to as a pairwise relationship index) of each pair of entities from the group of entities 106*a*-106*n* is generated based on the pairwise data, the behavioral information, the interaction information, and the emotion recognition information associated with each entity in the pair of entities. The entity pair index indicates one or more of a relationship quality measure, relationship stress or distress measure, or communication effectiveness measure between the two entities present in the pair of entities. The entity pair index is a timestamped entity pair index, i.e., a time of generation of the entity pair index is recorded. In one embodiment, the entity index and the entity pair index are at least one of: numeric or qualitative (ordinal categorical). In an example, the numeric format of the entity index and the entity pair index is an integer or a decimal number. In one embodiment, four categories of ranked, or ordinal categories, would include: “excellent, good, fair, poor.” In another embodiment, the entity index and the entity pair index are at least one of: nominal, ordinal, ratio and categorical form.

In one example, assume four individuals, i.e., entities, present in the group of entities. In the example, the entity index for each entity from the four entities are generated based on analysis of the data associated with each entity. Further, the entity pair index for each pair of entities is generated based on analysis of the pairwise data for each pair of entities.

In one embodiment, an entity profile and an entity pair profile are created upon receiving the data. The entity profile associated with each entity from the group of entities is created based on the entity data and the entity index. Further, the entity pair profile associated with each pair of entities is created based on the entity pair data and the entity pair index.

Further, the application server 112 is configured to generate the group network index for the group of entities 106*a*-106*n*. In one embodiment, a unique group identification is assigned to the group of entities 106*a*-106*n*. In the embodiment, the group network index is associated with the unique group identification. The unique group identification includes, but not limited to an alphanumeric identification number.

Further, the group network index is generated based on the entity index, and the entity pair index. In an embodiment, the group network index is generated by combining the entity index and the entity pair index. The entity index of each entity and the entity pair index of each pair of entities are weighted to determine relative importance, then summed, to generate the group network index. The group network index indicates a level of performance of the group of entities 106*a*-106*n*. The group network index is at least one of numeric or qualitative. In an example, the numeric format of the group network index is an integer or a decimal number. Qualitative ordinal categories would include: “excellent, good, fair, poor.” In another embodiment, the entity index and the entity pair index are at least one of: nominal, ordinal, ratio and categorical form. Further, the group network index is a timestamped, i.e., a time of generation of the group network index is recorded.

In one embodiment, the group network index indicates a severity or urgency of a problem faced by the group of entities 106*a*-106*n*, and along with weighted versions of the entity index and the entity pair index, help in triage or prioritization of intervention delivery to address the problem. The group network index is generated using a weighting technique. The weighting technique includes assigning relative weights to each of the entity index and the entity pair index values. The weights indicate the relative importance of each index as a component contributing to the overall group network index. In one embodiment, the weights assigned to each index are determined empirically through automated optimization on training data. In another embodiment, the weights assigned to the entity index and the entity pair index values are assigned based on human judgment. Further, the entity index of each entity is multiplied by the weights assigned to that entity index, and the entity pair index is multiplied by the weights of the respective entity pair index. Furthermore, the group network index is generated based on an addition of the multiplied entity indexes, and the multiplied entity pair indexes.

Upon generating the group network index, the application server 112 identifies the set of interventions associated with the group of entities 106*a*-106*n*. The set of interventions are identified using the historical data on prior groups, the interventions they received, and their outcomes based on the group network index value. In one embodiment, a “threshold” value is compared to the group network index. The threshold value is predefined based on historical group network indexes related to historical group of entities. The historical group of entities are of same type, i.e., if the group of entities is a family, then the historical group of entities are different families. Based on the comparison of the threshold value and the group network index, the presence or absence of a level of distress requiring intervention is identified. The level of the group network index, in combination with the weighted entity and entity pair scores that comprise its components, determine the modes and priority-level of interventions. The impact of interventions are measured based on a “distance” or difference between two values of the family network index at two points in time. The impact can also be evaluated in terms of “velocity” or improvement in the value of the index divided by time elapsed. The impact can also be evaluated by “efficiency” which is a measure of the change in the index divided by the cost or number of interventions provided.

In another embodiment, the application server 112 identifies the set of interventions based on analysis of the data and the group network index using a training set of interventions stored in memory in a training model. The training model is continuously updated in real-time with the training set of interventions associated with different group of entities. In one example, the different group of entities are of different types or same types. Based on analysis of the data and the group network index, the set of interventions associated with the group of entities are identified.

In yet another embodiment, one or more of the entity index, the entity pair index, and the group network index are compared with threshold values. The entity index is compared with the threshold value of entity index, the entity pair index is compared with the threshold value of entity pair index, and the group entity index is compared with the threshold value of group network index. Based on the comparison of the entity index, the entity pair index, and the group network index with respective threshold values, the set of interventions are identified for the group of entities. The threshold value of entity index and the threshold value of entity pair index are predefined. These thresholds are associated with clinically significant levels of symptoms or impairment, requiring intervention. In one embodiment, the timestamped entity index, the timestamped entity pair index, and the timestamped group network index are compared with threshold values, associated with the entity index, the entity pair index, and the group network index, to identify the set of interventions for the group of entities 106*a*-106*n*.

In an embodiment, the entity index of each entity and the entity pair index of each pair, calculated at two different points in time, are compared. Based on the comparison, further interventions are prioritized.

Further, the application server 112 recommends a set of online therapeutic services (i.e., plans) associated with the set of interventions. The set of online therapeutic services is used to improve the level of performance of the group of entities. The set of online therapeutic services are recommended to the group of entities. The set of online therapeutic services are recommended directly for one or more entities or the group of entities. The set of online therapeutic services corresponds to at least one of medical consultations and treatment, talk therapy, coaching, counselling sessions, and the like, for the one or more entities from the group of entities 106*a*-106*n*. The set of online therapeutic services may be referred as a treatment, a counselling, an interactive activity, or a therapy for the one or more entities from the group of entities 106*a*-106*n*.

In an embodiment, the set of online therapeutic services are provided to one or more entities from the group of entities in real-time. The set of online therapeutic services include at least psychotherapy, coaching, mediation, self-guided programs, medication prescriptions and management, and other medical interventions. The set of plans are recommended in different formats, for example written, charts, graphs, video, audio, by avatar, and the like. In an embodiment, the set of online therapeutic services are recommended through self-help, on-line, recorded, video, live interactions, prescriptions, and the like.

In one embodiment, one or more online therapeutic services are both recommended and delivered, based on the timestamped entity index, the timestamped entity pair index, and the timestamped group network index. Further, the execution of the set of online therapeutic services is prioritized based on the timestamped weighted entity index, and the timestamped weighted entity pair index. In one embodiment, the timestamped weighted entity index of each entity and the timestamped weighted entity pair index associated with each pair of entities are compared to prioritize the set of online therapeutic services.

The application server 112 further executes the set of online therapeutic services for the group of entities. In one embodiment, the execution of online therapeutic services comprises receiving a request from at least one entity from the group of entities. The request is associated with delivery of one or more online therapeutic services from the set of online therapeutic services. Upon receiving the request, the application server 112 automatically identifies the therapist 102 from the set of available therapists. The therapist 102 is identified based on analysis of therapist information associated with the set of therapists. The therapist information includes, but is not limited to, a therapist name, a therapist qualification, work experience, feedback from previous entities, the therapist location, the previous interventions and plans recommended, performance metrics based on prior services provided, and the like. Once the therapist 102 is identified, the application server 112 schedules therapeutic services (i.e., virtual sessions) for the one or more entities, from the group of entities, with the therapist 102. Further, the application server 112 transmits a notification to the therapist 102 and the group of entities 106*a*-106*n* upon scheduling the therapeutic services, thus, executing the online therapeutic services for the group of entities 106*a*-106*n*.

In one embodiment, the set of therapeutic services is further executed by the therapist 102 using the therapist device 104. The set of therapeutic services correspond to sessions conducted by the therapist 102 for the one or more entities or the group of entities. These sessions may be conducted online or in-person.

In one scenario, assume that the therapist or other service provider may have a caseload of 24 active families at any given time, as well as families who completed therapeutic services. Out of the hundreds of other families currently working with other therapists, a group of the same size may be created using digital database search such that attributes such as family structure, demographics, severity of impairment and duration of treatment may be matched as closely as possible. Further, the average rate of improvement (i.e., the velocity), and improvement per session or per other resources expended (i.e., the efficiency) of two historical group of entities are compared. Given the equivalence of the group comprising the therapist's current patient load, and the matched comparison group, statistically valid performance comparisons may be made between the two, to identify under-performing therapists. Recorded and stored video of their sessions may be studied to determine the reasons for underperformance. The under-performing therapist may be retrained or replaced. Furthermore, therapists with exceptionally good performance may also be identified in the same manner. Their recorded and stored video sessions may be studied to help identify superior therapeutic techniques that other therapists may be able to adopt. Furthermore, it may become apparent that certain therapist are obtain particularly good results treating particular diagnoses, or particular family demographics or other attributes, so that directing families to therapists based on those attributes will improve overall results.

In one example, assume a family as the group of entities that has a child with school refusal disorder. The child's symptoms-refusing to go to school-cause stress rising to the level of clinical anxiety for a primary caregiver, as well as stress in the relationship between the primary caregiver and her partner, and stress in the relationship between the primary caregiver and a co-parent living at a different place. Further, the index, in combination with the weighted entity pair index and the weighted entity index values, leads to providing as intervention couples counselling for the primary caregiver and her partner. Furthermore, the set of interventions provided may include co-parent counselling for parents those are no longer in relationship, medical-level individual treatment for the mother for anxiety, and of course direct treatment, either therapy or medical/psychiatric or both, for the child. The set of interventions helps to improve both individual entity pair index and entity index values, and the family group network index.

In the example, the family lacks resources to pursue all the interventions. Further, the weighted values of the of the individual entity pair index and entity index values, enable prioritization of recommended interventions so that the most beneficial can be provided first. Rank-ordering of interventions could lead first to a therapist working directly with the child to reduce the child's symptom's impact on the family. If the child manages to go to school, that will have largest benefit on the entire family network. Because the weight placed on the entity index of the child is high, intervention directly with the child receives highest priority.

During the execution, the application server 112 from time to time recalculates entity index, entity pair index, and family group index values. The level of improvement (or deterioration) is monitored based on the change in the group network index (i.e., the difference between two instances, or the "distance"). Other metrics include the rate of change of the various index values (i.e., the velocity), and changes in index values divided by the cost of services provided or the number of interventions provided. (i.e., the efficiency).

In one embodiment, the level of performance of the group of entities 106*a*-106*n* is monitored based on a difference between the timestamped group network index at different time instances.

In one embodiment, a set of online therapeutic services is delivered for the one or more entities from the group of entities. After delivery, changes in the index values are calculated.

Further, the application server 112 analyses the responses from the one or more entities to monitor the improvement in the group network index. Based on the monitoring, the application server 112 automatically recommends a subset of online therapeutic services from the set of online therapeutic services to the group of entities. The subset of online therapeutic services needs to be executed until the group network index reaches a defined value of the group network index. In one embodiment, an alert for the group of entities is generated. The alert is related to a subset of online therapeutic services, from the set of online therapeutic services, for the one or more entities from the group of entities. In one embodiment, the application server 112 revises the set of online therapeutic services to generate the subset of online therapeutic services for the one or more entities, in real-time, upon monitoring the improvement in the group network index for the definite time period. The subset of online therapeutic services is related to the interventions that needs to be continuously executed for the one or more entities for a definite time. The subset of online therapeutic services is referred as revised plans for the group of entities 106*a*-106*n*.

In one embodiment, the application server 112 compares the timestamped group network index of each group of entities (each family) with a timestamped group network index of all other groups of similarly-situated entities (or families) to triage resources or allocate limited available services among different groups.

In one embodiment, the application server 112 generates a new group network index (i.e., an improved group network index) for the group of entities 106*a*-106*n* based on executing the set of online therapeutic services. The new group network indicates the improved performance of the group of entities 106*a*-106*n*. The new group network index is further compared with the group network index to monitor the level of performance of the group of entities 106*a*-106*n*. The application server 112 further monitors the distance, the velocity, and the efficiency to monitor the level of performance. If the new group network index indicates deterioration rather than improvement of group performance than steps are taken to provide another or different set of intervention and services.

In one embodiment, the application server 112 monitors the distance between indexes, i.e., a previous group network index and an improved group network index. Further, the application server 112 monitors the velocity or rate of change of an index (i.e., the previous group network index and the improved group network index) by dividing by a time elapsed. The time elapsed indicates a difference between two instances of generation of the indexes (i.e., the time of generation of the previous group network index and the time of generation of the improved group network index). Furthermore, the application server 112 monitors the efficiency by dividing a measure of a total expenditure for the set of online therapeutic services, by the difference between the previous group network index and the improved group network index. The total expenditure is monitored during the time elapsed between a calculation of two indexes (i.e., the previous group network index and the improved group network index). Based on the monitoring the response to the online therapeutic services, the subset of plans is recommended to the group of entities 106*a*-106*n* and service recommendations for future, similarly-situated families are improved.

In an embodiment, the application server 112 generate a first network index (i.e., the previous group network index) as an initial index for the group of entities. The first network index is timestamped, i.e., the time of generation of the index is recorded. Further, the set of interventions for the group of entities is identified and delivered. After delivery of services, a second network index (i.e., the improved group network index) is generated for the group of entities. Further, the time of generation of the second index is recorded. Furthermore, the difference, or distance, the velocity, and the efficiency of service delivery are all monitored to support quality control of current service delivery, and optimization of future service delivery.

In one embodiment, the application server 112 refreshes the data based on the monitoring of the group network index for a definite time interval. Further, the application server 112 repeats the process of providing, or delivering, online therapeutic services to the group of entities. The process of facilitating online therapeutic services further comprises analyzing the refreshed data, generating a new group network index, identifying new optimal interventions, and recommending and delivering new online therapeutic services, to improve the performance of the group of entities.

In one exemplary embodiment, a family network health index is computed prior to a therapeutic intervention with the family. The initial index is referred as a first network index. Further, a new network index is generated periodically to evaluate the extent, pace, and efficiency of therapeutic progress.

Distance is simply a name for the difference between two values of an index, the velocity indicates a rate at which changes in the index occur, and the efficiency indicates quantity of resources, such as individual sessions or interventions, required to achieve a given change in the index (or conversely, change in the index per unit of resources expended). In an embodiment, the level of the index is intended to correlate closely with predictive measures of the family health and well-being. The family index may correlate closely with a family's need for all other medical services over the subsequent 90 or 180 days. Once data from large numbers of families are gathered and processed, optimal modes of care, and which relationships or individuals to direct those therapeutic resources to, can be determined using machine learning techniques.

Figure 1B:
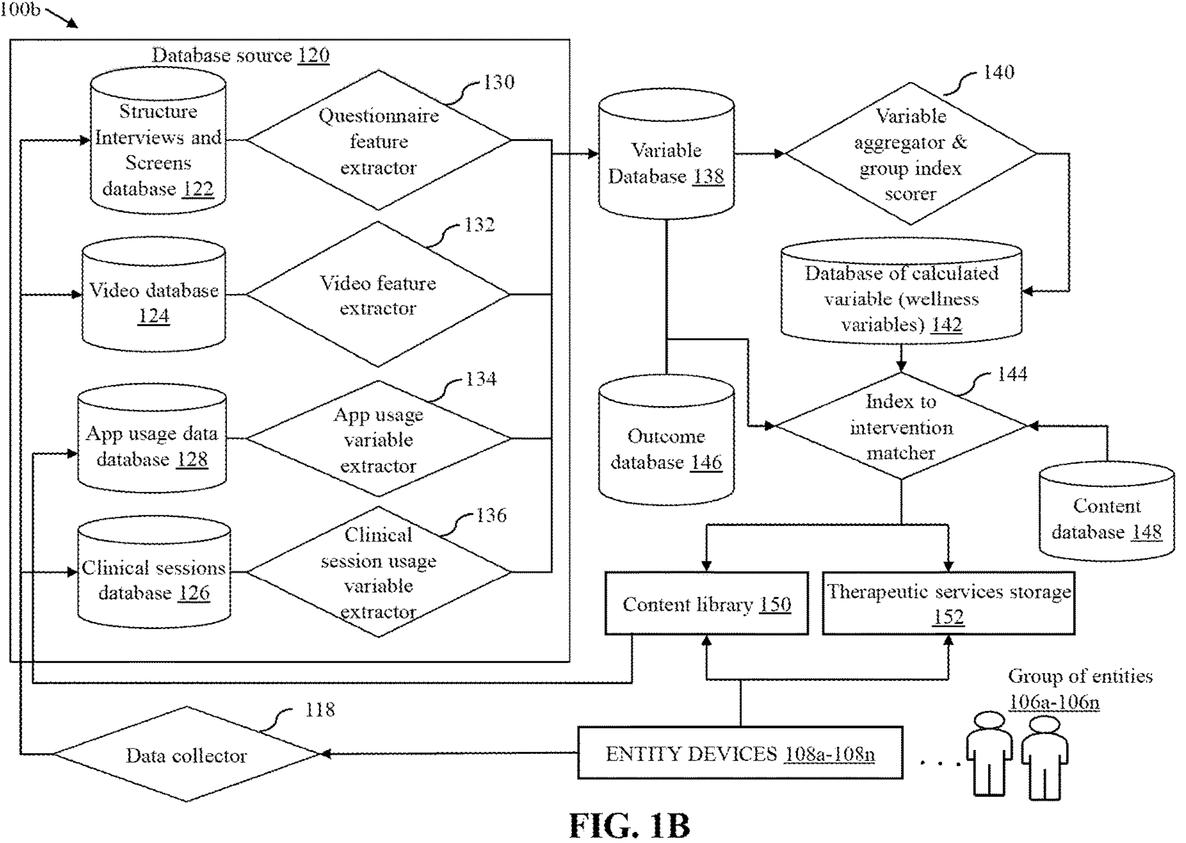
FIG. 1B is a block diagram that illustrates a system architecture representing data collection, identification of interventions, and recommendation of online therapeutic services to a group of entities, in accordance with an embodiment of the disclosure.

FIG. 1B is a block diagram that illustrates a system architecture 100*b* representing data collection, identification of therapeutic interventions, and recommendation of online therapeutic services to a group of entities, in accordance with an embodiment of the disclosure. The system architecture 100*b* includes a data collector 118 and a database source 120. In one embodiment, the data collector 118 is configured to receive data associated with assessments, videos, and sessions from the group of entities 106*a*-106*n*. The data is received via the entity devices 108*a*-108*n*. The data comprises demographic information, health information, behavioral information, emotion recognition information, and interaction information associated with each entity present in the group of entities 106*a*-106*n*. The data collector 118 is further configured to sort the data associated with assessments, videos and session and store the data in respective databases such as a structure interviews and screens database 122, a video database 124, and a clinical sessions database 126 of the database source 120. The data is sorted based on format of the data received from the group of entities 106*a*-106*n*.

The structured interviews and screens database 122 stores the data gathered from the interviews or question answer sessions of the group of entities 106*a*-106*n*. The video database 124 stores the data received as videos from the group of entities 106*a*-106*n*. Further, the clinical sessions database 126 stores the data related to health records received from the group of entities 106*a*-106*n*. Further, an app usage data database 128 of the database source 120 is configured to store data related to usage of the online therapeutic services facilitating platform running on the entity devices 108*a*-108*n*.

The database source 120 further includes a questionnaire feature extractor 130, a video feature extractor 132, an app usage variable extractor 134, and a clinical session usage variable extractor 136. The questionnaire feature extractor 130 is configured to extract the data required to evaluate a performance of the group of entities from the structure interviews and screens database 122 and store the extracted data in a variable database 138. Further, the video feature extractor 132 is configured to extract data (i.e., the video data) required to evaluate a performance of the group of entities from the video database 124 and store the extracted data in the variable database 138. The app usage variable extractor 128 is configured to extract the data required to evaluate a performance of the group of entities from the app usage data database 128 and store the extracted data in the variable database 138. Subsequently, the clinical session usage variable extractor 136 is configured to extract the data from the clinical sessions database 126 and store the extracted data in the variable database 138. The variable database 138 comprises the required data, associated with the group of entities 106*a*-106*n*, for further analysis.

Once the extracted data is stored in the variable database 138, a variable aggregator and group index scorer 140 is configured to extract the data (i.e., the entity data and the entity pair data) from the variable database 138. Further, the variable aggregator and group index scorer 140 generates an entity index, an entity pair index, and a group network index based on the extracted data. The variable aggregator and group index scorer 140 store the indexes in a database of calculated variable (wellness variables) 142.

Further, an index to intervention matcher 144 is configured to analyze the indexes and other granular variables, to identify the set of interventions for the group of entities. The index to invention matcher 144 receives inputs from the database of calculated variable 142, a content database 148, the variable database 138, and an outcome database 146. The set of interventions are identified based on interventions that have succeeded in lowering the index scores the most, at the highest velocity, or with the greatest efficiency across comparable groups of entities. In one embodiment, the content database 148 stores information related to the interventions that have succeeded in improving the index scores at the best according to these metrics, across different groups of entities. The outcome database 146 is configured to track and store effectiveness of specific treatments (i.e., online therapeutic services) on the different group of entities based on using the data from the variable database 138. The outcome database 146 stores an effect of the online therapeutic services on each entity or the group of entities over the defined time.

Furthermore, the index to intervention matcher 144 stores output, i.e., the identified set of interventions, in a content library 150 and a therapeutic services storage 152. In one embodiment, the entity devices 108*a*-108*n* store the data from the group of entities 16*a*-106*n* in the content library 150, and the therapeutic intervention storage 152. In one embodiment, the app usage data database 128 receives the data from the content library 150. The content library 150 includes data related to exercises (i.e., therapeutic services) performed by the group of entities using the online therapeutic services platform (i.e., app). Further, the therapeutic services storage 152 includes data associated with the set of online therapeutic services recommended to the group of entities 106*a*-106*n*. In one aspect, the content library 150 and the therapeutic services storage 152 receives data related to historical therapeutic services recommended to the group of entities 106*a*-106*n*. The set of online therapeutic services are further executed to improve a level of performance of the group of entities 106*a*-106*n*. Further, the level of performance of the group of entities is displayed on the entity devices (i.e., 108*a*-108*n*).

In an exemplary embodiment, assume a group of three families (i.e., Family 1, Family 2, Family 3) each with the same family structure. Each of the three families in this example include six individuals: child 1, the "child of concern" (an initial patient for mental health services), a "primary caregiver" parent, the primary caregiver's "partner" (that lives in the home but is not child 1's biological parent), two additional siblings (that live in the home with the primary caregiver and the partner) referred to as child 2 and child 3, and a "co-parent" (that is divorced or separated from the primary caregiver parent and lives outside the home but remains involved in co-parenting decisions affecting the child 1).

The data associated with each individual in each family is received through multiple modes (i.e., the video feeds, the audio, or the text). The data comprise demographic data such as an age and a gender, physiological or medical record data, video-analysis, questionnaires answered by or about the individual, etc. The data is further stored in the database server 114 according to the time of collection and the individual to whom the data refer. In an embodiment, individual-level data of different types are available, and is gathered for four (4) of the six (6) individuals in the family network. In this example, the family network comprises all six individuals, but data are only available on the primary caregiver parent, the child 1 (the child of concern), the child 2 (sibling), and the child 3 (sibling).

Further, the data of each individual in the family is assessed to generate an index based on established clinical criteria for mental health conditions. In an embodiment, the index is generated based on established empirical measures of individual adverse functioning (here called "impact").

The index may be present in a numerical range indicating zero as an absence of problems, and a maximum number as a severe clinical diagnosis or severe level of functional impairment. The individual index range for each individual in this exemplary embodiment for whom data are available is shown in Table 2.

TABLE 2

Individual index and range

| Individual index | Index range |
|---|---|
| Primary parent clinical levels of anxiety and/or depression (Anxiety_clinical + depression_clinical) | (0-2) |
| Child 1 - Primary child of concern - impact (impact_child_score) | (0-7) |
| Child 2 - impact (impact_child_score) | (0-7) |
| Child 3 - impact (impact_child_score) | (0-7) |

Further, pairwise relationship data for two individuals A,B is distinct from individual data. The pairwise relationship data corresponds to the way individual A affects individual B, positive or negative (a directed link); or a way of communication and functioning of the two individuals (an undirected link). The pairwise relationships, whether directed or undirected, are of differing relative importance and may be weighted differently in assessing overall network function.

In this exemplary embodiment, undirected pairwise relationship data are available for seven of the most important relationships (out of a theoretical total of fifteen (15) undirected links in a network of six nodes). The pairwise relationship index and the index ranges for this example are shown in Table 3.

TABLE 3

Pairwise relation index and index range

| Undirected Link Indexes | Index range |
|---|---|
| Primary parent and Child 1 (Child of concern) (impact_you_score) | (0-4) |
| Primary parent and Coparent (co-parenting_score) | (1-6) |
| Primary parent and Partner (partner_relationship_score) | (1-5) |
| Child 1 (Child of Concern) and Child 2 (impact_family_score) | (0-4) |
| Child 1 and Child 3 (impact_family_score) | (0-4) |
| Child 1 and Coparent (family_stress_score) | (0-4) |
| Child 1 and Partner (family_stress_score) | (0-4) |

Further, the individual and relationship-based indexed are processed to generate a single family network index (elsewhere called a "global" index or "network health" index). The above eleven indexes may be processed to derive the single-family network index. The simplest type of index, used in the present example, is simply the sum of weighted scores for each recorded index. More complex index calculations could include interaction effects between variables, if-then logic, and other non-linear combinations of the indexes, including interpolations for missing index values. The weights assigned to each of the indexes may be determined by prior empirical research or assigned using human judgment.

In an embodiment, a weighted sum of the above eleven indexes is used to create a numerical value of the family network index. Further, in this embodiment, changes in the family network index are expressed as percentages.

In this specific example, it is not necessary to interpolate or estimate values for the "missing" indexes for individuals and relationships that lacked direct assessment data. This is because group comparisons are performed only against other families with the same six-person family structure and same data-availability.

In the exemplary embodiment, the available indexes are each multiplied by the following weights, as shown in Table 4, then summed to create a single family network index.

TABLE 4

Index range and multiplication to generate single family network index.

| Index | Range and multiplication |
|---|---|
| Primary parent clinical levels of anxiety and/or depression (anxiety_clinical + depression_clinical) | (Range 0-2) multiplied by 5 |
| Child 1 - Primary child of concern - impact (impact_child_score) | (Range 0-7) multiplied by 2 |
| Child 2 - impact (impact_child_score) | (Range 0-7) multiplied by 1 |
| Child 3 - impact (impact_child_score) | (Range 0-7) multiplied by 1 |
| Primary parent and Child 1 (Child of concern) (impact_you_score) | (Range 0-4) multiplied by 1 |
| Primary parent and Coparent (co-parenting_score) | (Range 0-6) multiplied by 1 |
| Primary parent and Partner (partner_relationship_score) | (Range 0-5) multiplied by 1 |
| Child 1 (Child of Concern) and Child 2 (impact_family_score) | (Range 0-4) multiplied by 0.5 |
| Child 1 and Child 3 (impact_family_score) | (Range 0-4) multiplied by 0.5 |
| Child 1 and Coparent (family_stress_score) | (Range 0-4) multiplied by 1 |
| Child 1 and Partner | (Range 0-4) multiplied by 1 |

In the network analysis, the network indexes on the individual and the relationship level are generated, and the family network index is generated.

The indexes (11+1) may be used for triage within a family (level of care needed based on severity), rank-ordering of priorities for delivery of therapeutic interventions to a family, or for triage across multiple families.

In one example, the family network index is a measure of the distress and impact of the mental health challenges within the family. The family network index is used further to automatically triage families to initial assessment with the therapist. The therapist may be a for example a licensed mental health professional, or a trained master's level professional (e.g., BCBA, early childhood specialist, educator). Further, the individual and relationship indexes are used within the triage by evaluating the relative severity of each individual and relationship index compared to the data.

Further, the family network index is used in combination with the weighted individual and relationship indexes to rank optimal interventions from most urgent to least urgent (i.e., the highest to lowest weighted components of the family network index). The set of interventions may include evidence-based psychosocial interventions (at the child and parent level). The set of interventions may further include psychiatric evaluation and medications, clinical parenting interventions for clinically significant parent-child relationship challenges. Further, the set of interventions may include parenting interventions and support for "typical" but problematic parent-child relationship challenges, parent-partner couple's counselling. The set of interventions may include parent-alignment guidance and support, self-guided interventions, personalized content that includes activities, educational material, etc.

The family network index, and the weighted individual index and pairwise relationship index components, may define the urgency of intervention, the intensity of the interventions, and the relative ordering of the interventions. The intensity of the interventions includes the frequency of interventions, a length of individual interventions, and an intensity of between session/asynchronous interactions via messaging and/or phone calls.

The family may receive an alert by email, through a secure platform, text or other means that indicates a recommendation to proceed with one or more interventions (e.g., child therapy for separation anxiety, parent treatment for anxiety, and parent-partner counseling). In an embodiment, each intervention is part of a family-level care team with each of the providers integrating care and evaluating the efficacy of care at the level of the family mental health index. However, the family might not be able to afford or be ready to start multiple therapies at one time. Further, the application server 112 recommends starting with the highest ranked intervention (e.g., child's separation anxiety) for the family's mental health improvement.

If the family mental health is not sufficiently improving, then the application server 112 recommends the next-highest-ranked intervention to pursue in order to improve the impact at the level of the family mental health. The application server 112 is configured to track the individual, relationship, and family mental health index values as an essential part of the treatment session or the engagement level. The index defines the performance evaluation platform of care from triage to assessment, to intervention, to outcome monitoring, and on-going monitoring even when interventions are done.

Family groups are not static in their demographics, their membership, or in their mental health needs. Further, an individual child's normal development (growing from infant to toddler to preschooler to school-age to adolescence) changes how a family is best served. Furthermore, changes in family structure (e.g., new baby or parent divorce or re-marriage) or functioning (e.g., parent gets ill and no longer able to work, parent was primary parent goes back to work and other parent becomes primary parent) occurs over the time. Environmental context changes (e.g., moving, new school, parent loses job) take place over the time. In the embodiment, the application server 112 creates a dynamic index that captures the changes in the group of entities, and determines and provides optimal interventions as they change.

In one embodiment, for families with the 6-person structure of the example, the group network index ranges from a theoretical minimum of zero to a maximum of 65. In the alternative to the simple numerical range, the index may be expressed as a percentile against a comparable population (that is, less than 50% would be fewer problems than the median family in the population, 50% would be a median, and the more severe the problems, the higher the percentile).

Further, the table 5 shows the first index, a second index, the total number of therapeutic interventions performed between the first index and the second index, and the total number of days elapsed between the first index and the second index. (For convenience, total days are also given as fractional months, assuming at 30.5-day average month).

In an embodiment, the interventions may vary in intensity and cost but for simplicity here only the total number of interventions is counted. Therapeutic interventions may be targeted at an individual, or a pair of individuals together, and are not limited to the child of concern. For example, interventions could include talk therapy with the child of concern and/or the primary caregiver, co-parent counselling with primary caregiver and co-parent, or couples counselling with the primary caregiver and partner.

TABLE 5

Two Indexes for Three Families with Elapsed Time and Interventions

| | First Index | Second Index | Interventions | Total Days Elapsed | Months elapsed |
|---|---|---|---|---|---|
| Family 1 | 25 | 13.5 | 19 | 143 | (4.7) |
| Family 2 | 4 | 20.0 | 9 | 93 | (3.05) |
| Family 3 | 14 | 8.0 | 24 | 148 | (4.85) |

Further, the index data of in Table 5 is processed to calculate distance, velocity and efficiency. The distance is computed based on a simple difference between scores. It gives a measure of change in family wellness during the time elapsed between calculation of index 1 and the index 2. The computation of the distance is as shown in Table 6.

TABLE 6

Computation of distance.

| | Difference | Distance | Distance (as percentage) |
|---|---|---|---|
| Family 1 | (25-13.5) = | 11.5 | 46% improvement |
| Family 2 | (24-20) = | 4 | 16.67% improvement |
| Family 3 | (14-8) = | 6 | 42.8% improvement |

Furthermore, velocity is computed as a rate of change in distance based on the difference between the index 1 and the index 2 scores, divided by the elapsed time between the Indexes. The computation of the velocity is as shown in the below Table 7.

TABLE 7

Computation of velocity.

| | Distance Raw | Improvement percentage | Elapsed days time | Elapsed months | Velocity (%) |
|---|---|---|---|---|---|
| Family 1 | 11.5 | 46% improvement | 143 | 4.70 | 9.8% per month |

TABLE 7-continued

Computation of velocity.

| | Distance Raw | Improvement percentage | Elapsed days time | Elapsed months | Velocity (%) |
|---|---|---|---|---|---|
| Family 2 | 4 | 16.67% improvement | 93 | 3.05 | 5.5% per month |
| Family 3 | 6 | 42.8% improvement | 148 | 4.85 | 8.8% per month |

Subsequently, the efficiency is a measure based on the difference between the index 1 and index 2, divided by the total number of interventions provided. The computation of efficiency is as shown in the below Table 8.

TABLE 8

Computation of efficiency.

| | Distance Improvement | Interventions | Efficiency, % change per intervention |
|---|---|---|---|
| Family 1 | 46% | 19 | 2.4% |
| Family 2 | 16.67% | 9 | 1.9% |
| Family 3 | 42.8% | 24 | 1.8% |

In this example, all three families saw significant improvement as measured by the family network health index (elsewhere, "global" index or "family network index"), with the distance, expressed as a percentage of the first index, ranging from 16.67% to 46%. The velocity, or rate of improvement during treatment, was quite consistent between families, ranging from 5.5% to 9.8% per month. Finally, the average efficiency of treatment was very consistent between families, ranging from 1.8% to 2.4% per intervention. Various other functionalities and operations of the application server 112 have been described in detail in conjunction with FIGS. 2-11.

Figure 2:
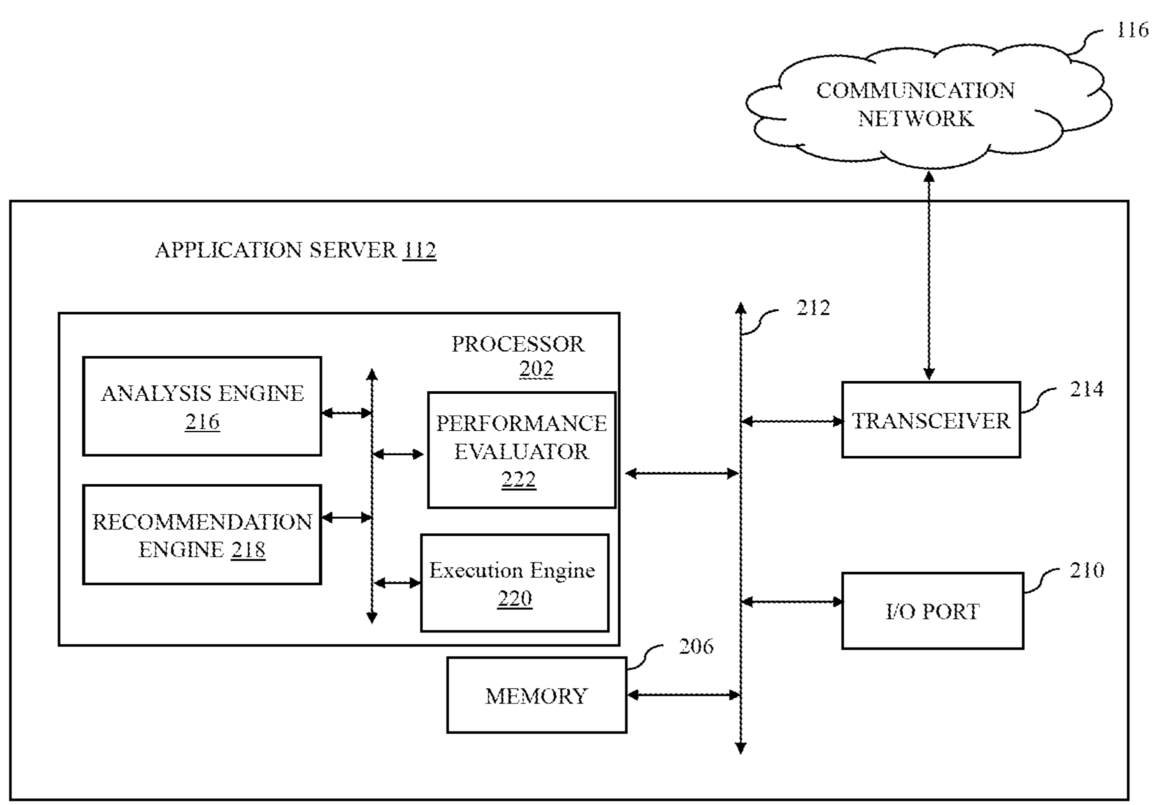
FIG. 2 is a block diagram that illustrates an application server of the system of FIG. 1A-1B for facilitating online therapeutic services to the group of entities, in accordance with an embodiment of the disclosure.

FIG. 2 is a block diagram that illustrates the application server 112 of the system for facilitating online therapeutic services to the group of entities, in accordance with an embodiment of the disclosure. An embodiment of the disclosure, or portions thereof, may be implemented as computer readable code on the system for facilitating the online therapeutic services to the group of entities. In one example, the application server 112 and the database server 114 of FIG. 1 may be implemented in the system using hardware, software, firmware, non-transitory computer readable media having instructions stored thereon, or a combination thereof and may be implemented in one or more computer systems or other processing systems. Hardware, software, or any combination thereof may embody modules and components used to implement the method for facilitating online therapeutic services to the group of entities of FIG. 3.

The application server 112 may include a processor 202 that may be a special purpose or a general-purpose processing device. The processor 202 may be a single processor, multiple processors, or combinations thereof. The processor 202 may have one or more processor "cores." Further, the processor 202 may be connected to a communication infrastructure 204, such as a bus, a bridge, a message queue, multi-core message-passing scheme, or the like. The processor 202 may further comprise an analysis engine 216, a recommendation engine 218, an execution engine 220, and a performance evaluator 222. The analysis engine 216, the recommendation engine 218, the execution engine 220, and the performance evaluator 222 may be configured to execute the steps of the method for facilitating online therapeutic services to the group of entities as mentioned in FIG. 3.

In an embodiment, the analysis engine 216 is configured to receive the data associated with the group of entities. Further, the analysis engine 216 is configured to analyze the data associated with the group of entities to generate the entity index for each entity and the entity pair index for each pair of entities in the group of entities. Upon generating the entity index and the entity pair index, the analysis engine 216 is configured to generate the group network index.

Further, the recommendation engine 218 is configured to identify the set of interventions using an optimization technique based on the group network index value, and optionally, a threshold for clinical levels of symptoms or impairment. Subsequently, the recommendation engine 218 is configured to recommend the set of online therapeutic services associated with the set of interventions.

The execution engine 220 is further configured to execute the set of online therapeutic services for the group of entities. The set of online therapeutic services are executed to improve the level of performance of the group of entities.

Further, the performance evaluator 222 is configured to monitor the level of performance of the group or entities during the execution of the set of online therapeutic services for a definite time period, thus facilitating the online therapeutic services to the group of entities.

The application server 112 may further include a memory 206. Examples of the memory 206 may include RAM, ROM, and the like. Further, the removable storage drive may read from and/or write to a removable storage device in a manner known in the art. In an embodiment, the removable storage unit may be a non-transitory computer readable recording media.

The application server 112 may further include an input/output (I/O) port 210, a communication interface 212, and a transceiver 214. The I/O port 210 may include various input and output devices that are configured to communicate with the processor 202. Examples of the input devices may include a keyboard, a mouse, a joystick, a touchscreen, a microphone, and the like. Examples of the output devices may include a display screen, a speaker, headphones, and the like. The communication interface 212 may be configured to allow data to be transferred between the application server 112 and various devices that are communicatively coupled to the application server 112. Examples of the communication interface 212 may include a modem, a network interface, i.e., an Ethernet card, a communication port, and the like. Data transferred via the communication interface 212 may be signals, such as electronic, electromagnetic, optical, or other signals as will be apparent to a person skilled in the art. The signals may travel via a communications channel which may be configured to transmit the signals to the various devices that are communicatively coupled to the application server 112. Examples of the communication channel may include a wired, wireless, and/or optical medium such as cable, fiber optics, a phone line, a cellular phone link, a radio frequency link, and the like.

Further, the transceiver 214 is configured to transmit information or receive information via the communication interface 212. The memory 206 may refer to non-transitory computer readable mediums that may provide data that enables the application server 112 to implement the method for evaluation of performance of the group of entities illustrated in FIG. 3.

Figure 3A:
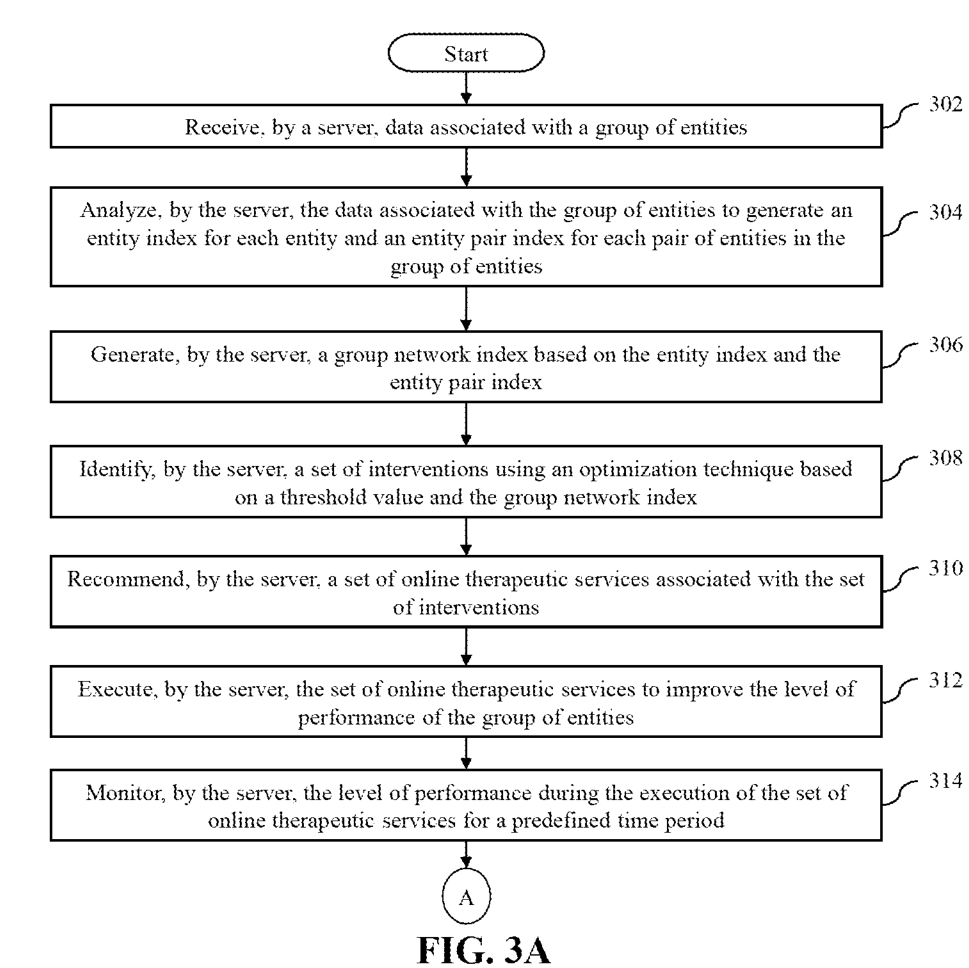
FIGS. 3A-3C, collectively, represent a flow chart that illustrates a method for facilitating online therapeutic services to a group of entities, in accordance with an embodiment of the disclosure.
Figure 3B:
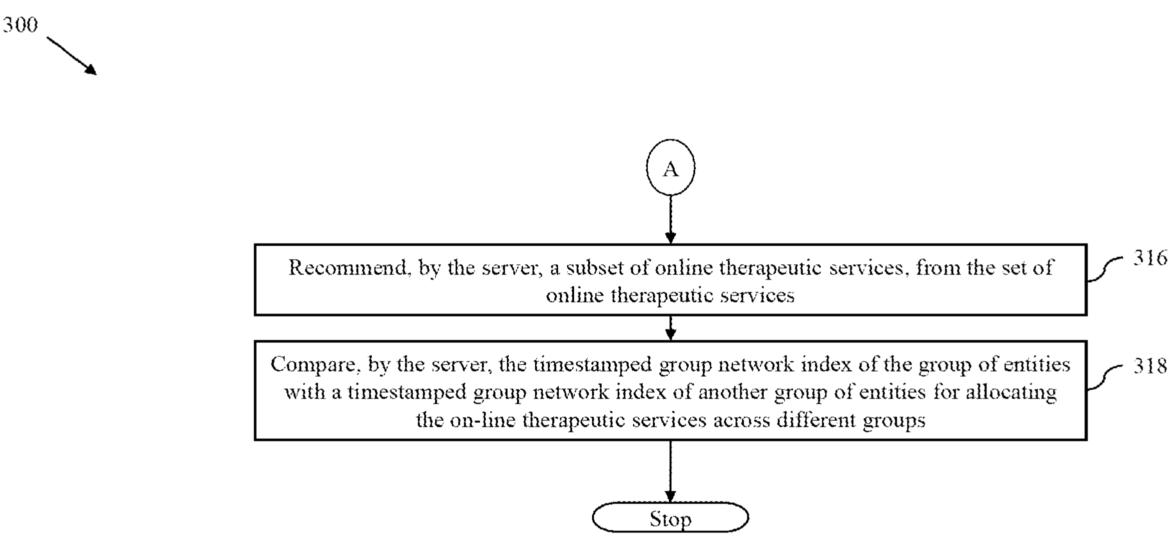
Figure 3C:
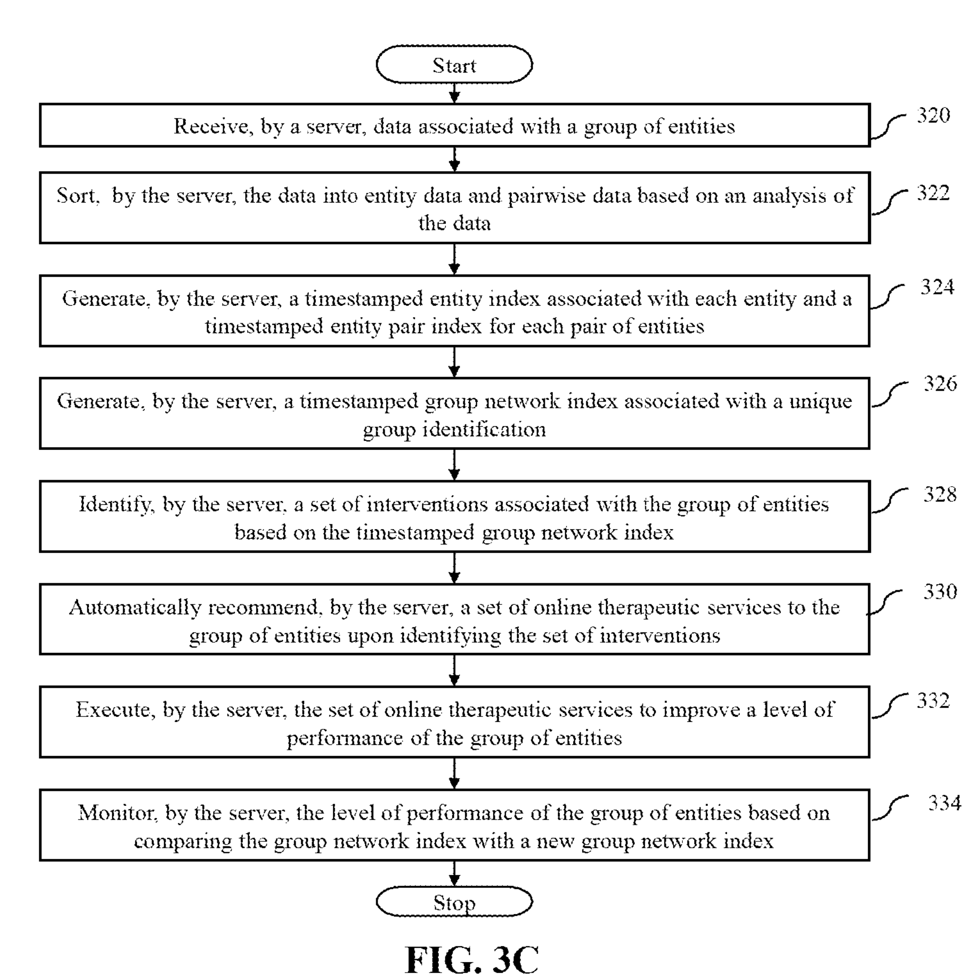

FIG. 3A-3C, collectively, represents a flow chart 300 that illustrates a method for facilitating online therapeutic services to a group of entities, in accordance with an embodiment of the disclosure.

The method is initiated at 302 when data associated with the group of entities is received. Further, at 304, the data associated with the group of entities is analyzed to generate an entity index for each entity and an entity pair index for each pair of entities in the group of entities.

At 306, a group network index is generated based on the entity index and the entity pair index. In an embodiment, the group network index indicates a level of performance of the group of entities.

At 308, a set of interventions are identified using an optimization technique based on a the group network index value.

At 310, a set of online therapeutic services associated with the set of interventions are recommended to the group of entities 106*a*-106*n*.

At 312, the set of online therapeutic services are executed to improve the level of performance of the group of entities.

At 314, the level of performance is monitored during the execution of the set of online therapeutic services for a definite time period, thus facilitating the online therapeutic services to the group of entities.

At 316, a subset of online therapeutic services, from the set of online therapeutic services, are recommended to be executed for one or more entities from the group of entities until the group network index reaches a defined target value of the group network index.

At 318, group network index values for comparable groups are compared in order to triage, or allocate limited therapeutic services (online or off-line) across different groups.

FIG. 3C represents a flow chart 300 that illustrates an embodiment of the method for facilitating online therapeutic services to a group of entities, in accordance with an embodiment of the present subject matter.

At 320, data associated with a group of entities is received.

At 322, the data is sorted into entity data and pairwise data based on an analysis of the data. In one embodiment, the entity data is associated with each entity present in the group of entities, and the pairwise data is associated with each pair of entities present in the group of entities.

At 324, a timestamped entity index associated with each entity and a timestamped entity pair index for each pair of entities are generated based on the sorted data.

At 326, a timestamped group network index associated with a unique group identification based on the timestamped entity index and the timestamped entity pair index. In one embodiment, the unique group identification is assigned to the group of entities.

At 328, a set of interventions associated with the group of entities are identified based on the timestamped group network index, the timestamped entity index, and the timestamped entity pair index.

At 330, a set of online therapeutic services are automatically recommended to the group of entities upon identifying the set of interventions.

At 332, the set of online therapeutic services are executed to improve a level of performance of the group of entities.

At 324, the level of performance of the group of entities is evaluated based on comparing the group network index with a new group network index. In one embodiment, the new group network index is generated upon execution of some or all of the set of online therapeutic services, thus measuring the impact of the online therapeutic services on the performance of the group of entities.

Figure 4:
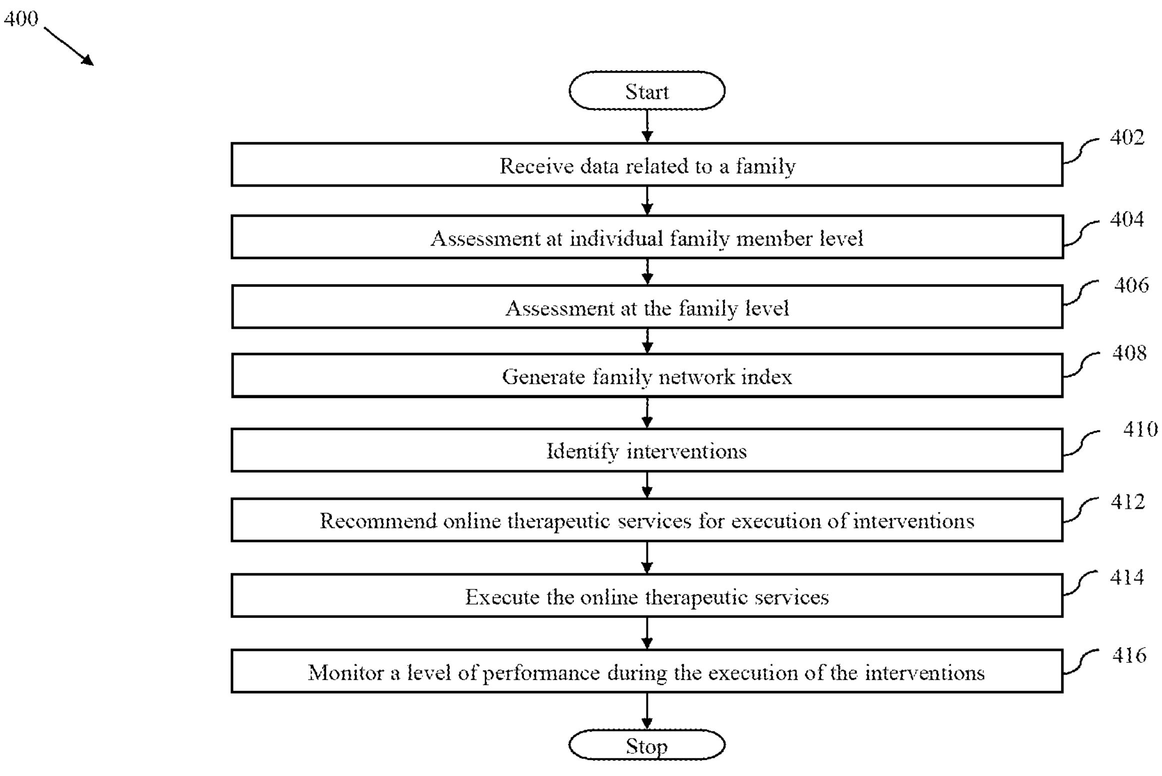
FIG. 4 represents a flow chart that illustrates a method for facilitating online therapeutic services to a family, in accordance with an embodiment of the disclosure.

FIG. 4 represents a flow chart 400 that illustrates a method for facilitating online therapeutic services to a family, in accordance with an embodiment of the present subject matter. In one embodiment, at 402, data associated with the family is received. In an embodiment, the family is the group of entities. The data is associated with children and adults, including a primary caregiver present in the family. The data includes the emotion recognition information, and interaction information relating to the caregiver and the child. The interaction information includes a frequency of interaction, and types of interactions. Further, the data comprises mental health screen data, such as generalized screens like Strengths and Difficulties Questionnaire (SDQ), and specialized screens, such as Spence Children's Anxiety Scale. The data further comprises structured interview results, structured and unstructured videos of behavior and emotions, and video data of behavior and interaction. The data further comprises video data including, but is not limited, to facial expressions and emotion-inference, analysis of pauses, speech patterns, and interrupting, etc. The video data is further used for analysis of body language and play, analysis of motion and identification of motor deficits or developmental delays, and the like. Further, in some embodiments, the data includes a physical location, health or biological data, such as medication dosage and frequency, blood pressure, a heart rate or pulse, and blood tests including for example drug tests and other types of drug tests. In some embodiments, the data further comprises a sleep duration, a stress test, and a physical activity tracking. Further, the data includes demographics and risk factors, such as age, ethnicity, location or geocoding, an adverse childhood events, and socioeconomic status.

At 404, the data is analyzed to assess each family member (i.e., entity). Based on the analysis, an entity index for each family member is generated.

At 406, the data is analyzed to assess each pair of entities in the family. Based on the analysis, an entity pair index for each pair in the family is generated. The entity pair indexes includes caregiver-child dyad relationship indexes, other adult-child dyads, child-child dyads and adult-adult dyads.

At 408, a family network index is generated based on a weighted combination of the entity indexes and the entity pair indexes. The family network index can take multiple forms, including numeric and ordinal categories such as "poor", "moderate", and "positive".

At 410, a set of interventions are identified using optimization based on historical experience with other families with similar attributes. The set of interventions, referred as optimal interventions, are associated with the family. The set of interventions lead to improvement in functioning of the family.

At 412, online therapeutic services are recommended and delivered to the family by different means or formats, such as electronic, paper, charts, graphs, video, audio, by avatar and the like. The set of online therapeutic services include direct child services, direct parent services, direct parent-child services, and couples services. The set of online therapeutic services include psychotherapy, medication management, self-guided programs and/or video programs, nutrition management, exercise management, sleep management and the like.

At 414, the set of online therapeutic services is executed to improve the level of performance of the group of entities 106*a*-106*n*.

At 416, a level of performance of the family is monitored before and after delivery of online therapeutic services. Further, when the data are refreshed, new interventions may be recommended and delivered.

FIGS. 5A-5J, collectively, represent an exemplary embodiment 500 of facilitating online therapeutic services to the family, in accordance with an embodiment of the disclosure. In one embodiment, an entity index related to individuals in the family, an entity pair index related to each pair of individuals in the family, and a family network index are represented as blocks with different patterns in the FIGS. 5A-5J. In the embodiment, a level of performance associated with the entity indexes, the entity pair indexes, and the family network index is indicated by the different patterns. In one embodiment, a diagonal lines pattern indicates a "poor" index (i.e., poor level of performance), a dotted pattern indicates a "moderate" index (i.e., moderate level of performance), and no pattern (i.e., blank pattern) indicates a "positive" index (i.e., excellent level of performance). This is an example of an ordinal (ordered from worst to best) categorical expression of the family network index.

Figure 5A:
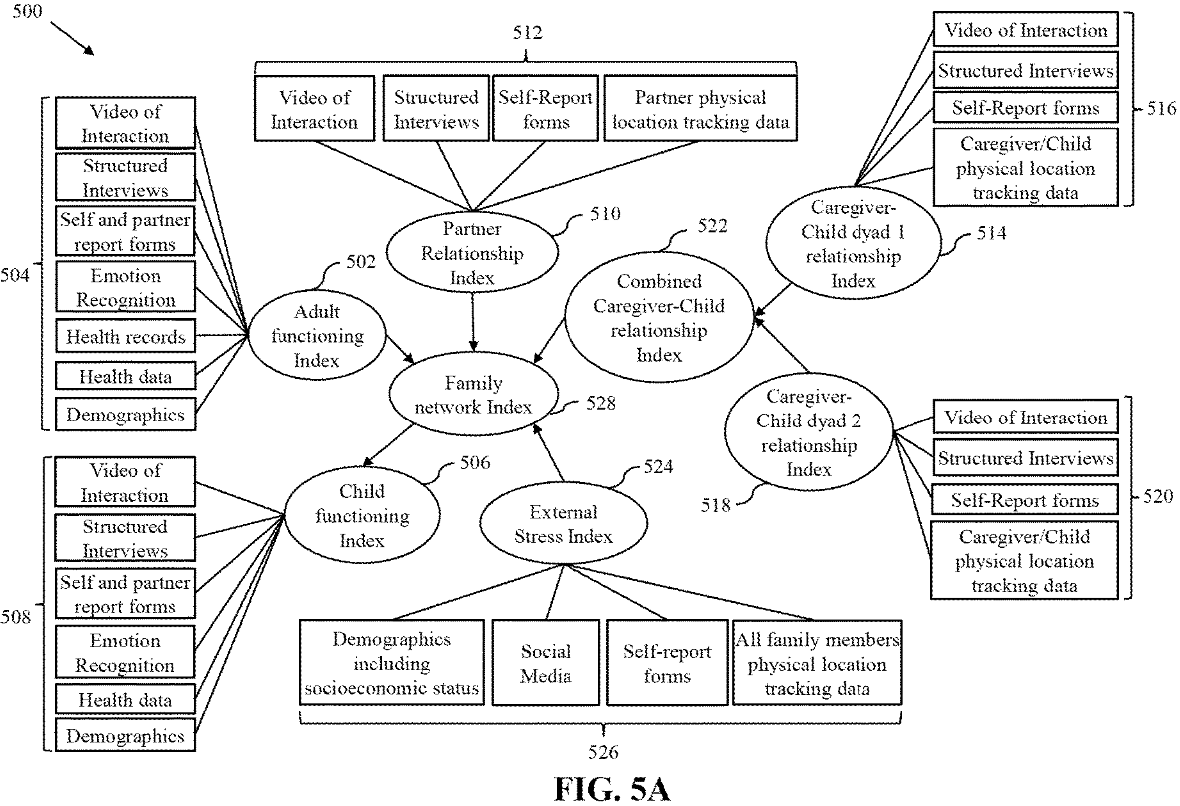
FIGS. 5A-5J, collectively, represent an exemplary embodiment for facilitating online therapeutic services to the family, in accordance with an embodiment of the disclosure.

FIG. 5A shows generation of a family network, in accordance with an embodiment of the disclosure. In an embodiment, an adult functioning index 502 is generated based on data 504 including, for example, a video of interactions, structured interviews, self and partner report forms, emotion recognition information, health records, health data and demographics of an adult in the family. Further, a child functioning index 506 is generated based on data 508 including, for example, a video of interactions, structured interviews, self and partner report forms, emotion recognition information, health records, health data and demographics of a child in the family.

Further, a partner relationship index 510 is generated based on data 512 including, for example, the video of interactions, the structured interviews, the self-report forms and a partner location data. An external stress index 524 is generated based on data 526 including the demographic such as a socioeconomic status, social media information, the self-report forms, and location information of each family member. Furthermore, a caregiver-child dyad 1 relationship index 514 is generated based on data 516 including, for example, the video of interactions, the structured interviews, the self-report forms and the location information of the caregiver and the child. Subsequently, a caregiver-child dyad 2 relationship index 518 is generated based on data 520 including, for example, the video of interactions, the structured interviews, the self-report forms and the location information of the caregiver and the child.

Further, the adult functioning index 502, the child functioning index 506, the partner relationship index 510, the external stress index 524, and the combined caregiver-child relationship index 522 are used to generate a family network index 528. The family network index 528 indicates the performance of the family.

Figure 5B:
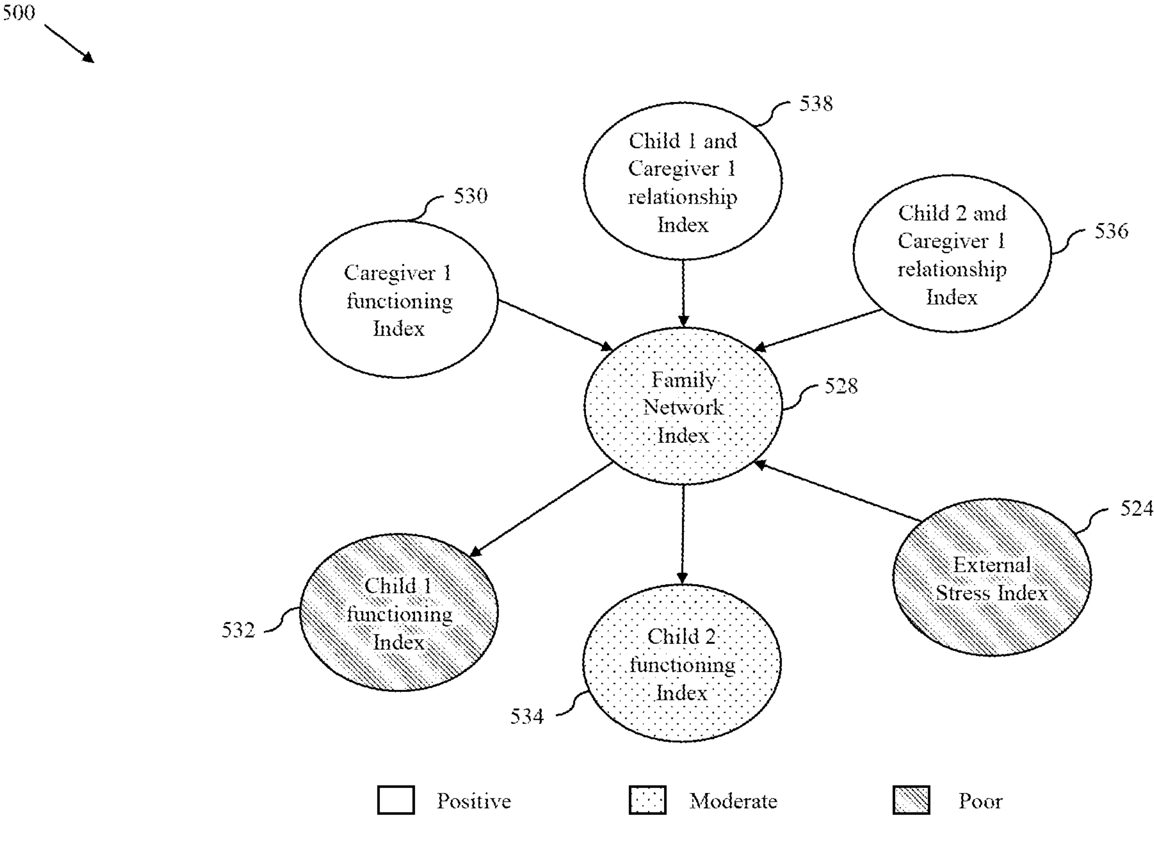
Figure 5C:
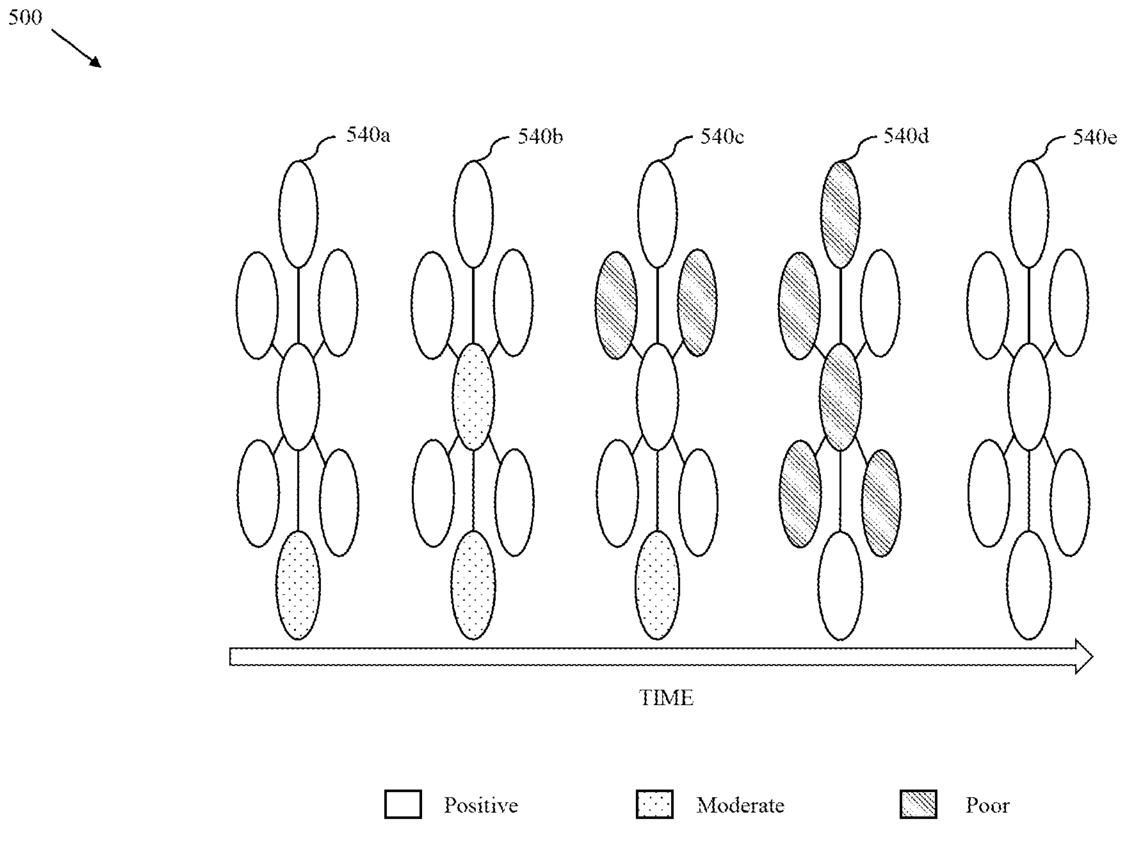

FIGS. 5B-5C, collectively, shows an analysis of the data to generate the family network index 528, in accordance with the embodiment of the disclosure. In an embodiment, the data associated with the family is received from multiple sources. The data is further analyzed to generate indexes such as the external stress index 524, a caregiver-1 functioning index 530, a child-1 functioning index 532, a child-2 functioning index 534, a child-1 and caregiver-1 relationship index 538, and a child-2 and caregiver-1 relationship index 536. The indexes are further combined to generate the family network index 528. FIG. 5B shows that the child-1 functioning index 532 and the external stress index 524 are poor, and the child-2 functioning index 534 is moderate, and hence the family network index 528 is moderate. The family network index 528 indicates the level of performance of the family.

Further, FIG. 5C represents different time instances, i.e., 540*a*, 540*b*, 540*c*, 540*d*, and 540*e*, showing an improvement in the family network index 528. The family network index 528 improves over the time instances (i.e., 540*a*-540*c*) based on changes in the child-1 functioning index 532, the child-2 functioning index 534, and the external stress index 524.

Figure 5D:
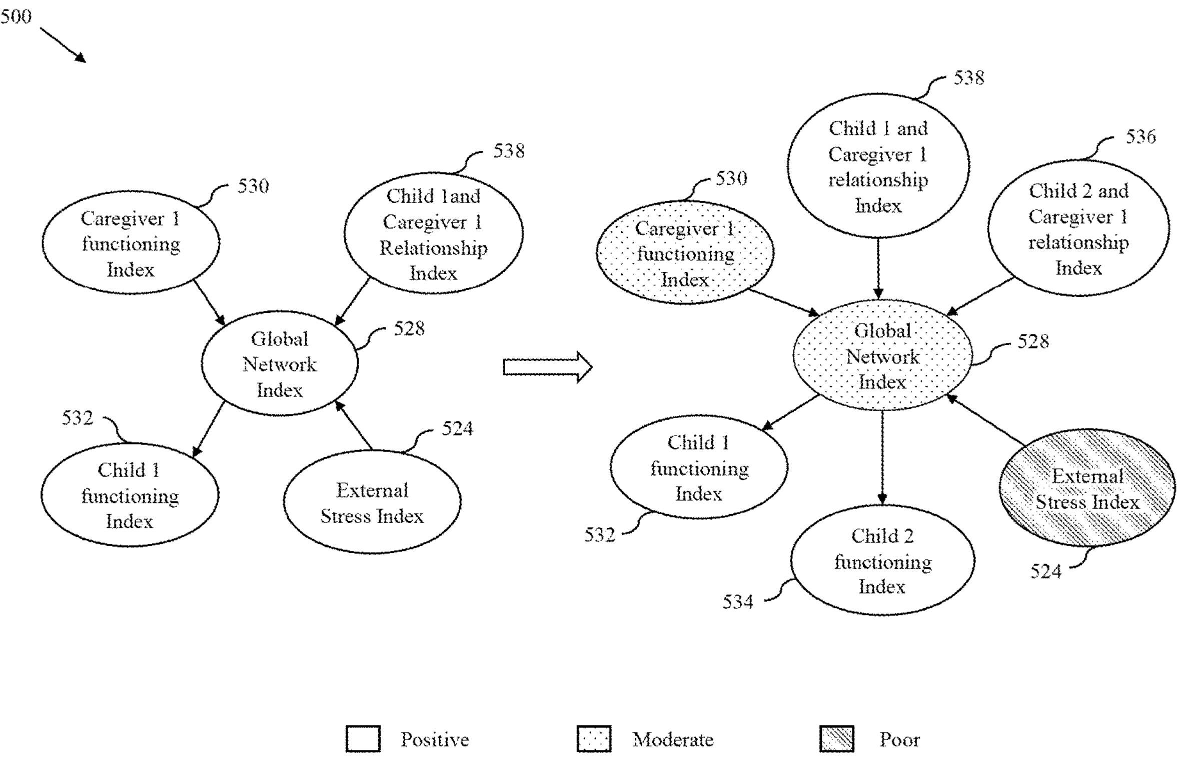

FIG. 5D shows an exemplary embodiment for change in the family network index upon an addition of a child in the family, in accordance with an embodiment of the disclosure. In the exemplary embodiment, a global network index 528 (also referred to as the family network index) is generated based on the caregiver-1 functioning index 530, the child-1 functioning index 532, the external stress index 524, and the child-1 and caregiver-1 relationship index 538. Further, a new child, i.e., child-2, is added to the family. In an embodiment, a new node related to the child-2 functioning is added to the family network, and changes in the family network index are monitored. Upon addition of the child-2, the family network index 528 is generated based on the caregiver-1 functioning index 530, the child-1 functioning index 532, the child-2 functioning index 534, the child-2 and caregiver-1 functioning index 536, the child-1 and caregiver-1 functioning index 538, and the external stress index 524. The addition of the new child, i.e., the child-2, changes a stress level in the family and impacts the caregiver-1 functioning index 530. Further, multiple interconnected relationships are monitored based on the changes in the family. Furthermore, relationships may be analyzed as either undirected or directed link between two individuals. Subsequently, a magnitude of the relationships is estimated. The change in the family leads to the external stress index 524 being poor, the caregiver-1 functioning index 530 being moderate, and hence the family ("global") network index 528 being moderate.

Figure 5E:
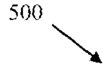
Figure 5E:
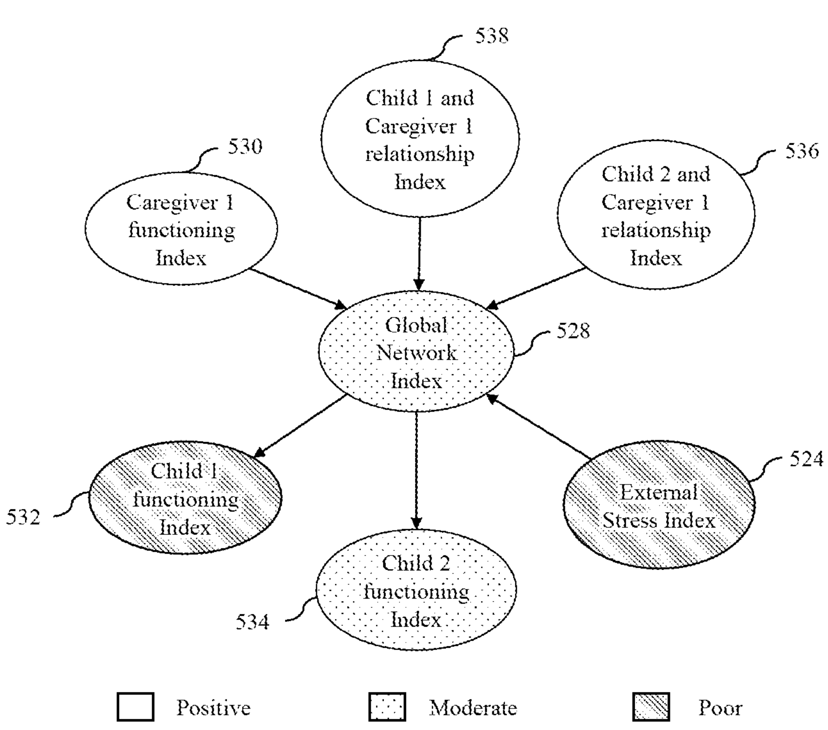
Figure 5F:
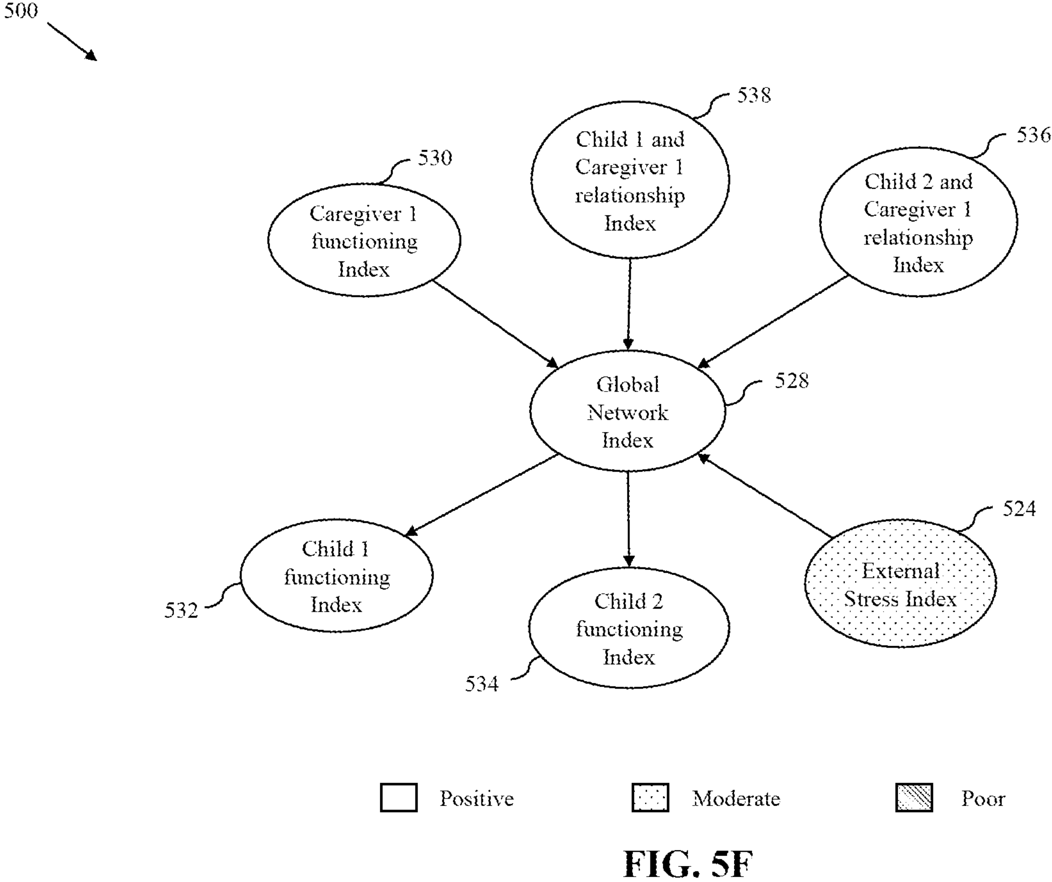

FIG. 5E-5F, collectively, shows an exemplary embodiment of facilitating online therapeutic services to the family, in accordance with an embodiment of the disclosure. In the exemplary embodiment, a single parent family, i.e., the caregiver-1, is facing stress due to COVID-19. Further, the child-1 is having impairing social-emotional behavioral concerns, and the child-2 has subclinical concerns. The data related to the family is received. Further, the individual indexes, i.e., the caregiver-1 functioning index 530, the child-1 functioning index 532, the child-2 functioning index 534, and the external stress index 524 are generated. Furthermore, the pairwise indexes, i.e., the child-2 and caregiver-1 functioning index 536, and the child-1 and caregiver-1 functioning index 538 are generated. Subsequently, the global network index 528, for the family, is generated based on the individual indexes and the pairwise indexes. Further, the set of interventions are identified. The set of interventions include a family support around coping with COVID-19 and problem-solving financial challenges, and parent engaged child mental health support for the child-1.

Further, the set of online therapeutic services associated with a set of interventions is recommended. The set of online therapeutic services include two parent/family sessions, six sessions for the child-1 mental health support. Further, the set of online therapeutic services are executed for the definite time period. Based on the execution, a response of the execution of the set of online therapeutic services are monitored. The response includes full response for treatment to the caregiver-1, and full response from the child-1 and the child-2.

FIG. 5F shows the change in the indexes of the members (i.e., entities) in the family, in accordance with an embodiment of the disclosure. Upon executing the set of online therapeutic services, the external stress index 524 is improved from poor to moderate, the child-1 functioning index 532 is improved from poor to positive, and the child-2 functioning index 534 is improved from moderate to positive. Further, the global network index 528 (i.e., the family network index) is improved from moderate to positive. Furthermore, the set of online therapeutic services are revised based on the improvement in the global network index 528. The revised online therapeutic services include skills generalization work and graduation.

Figure 5G:
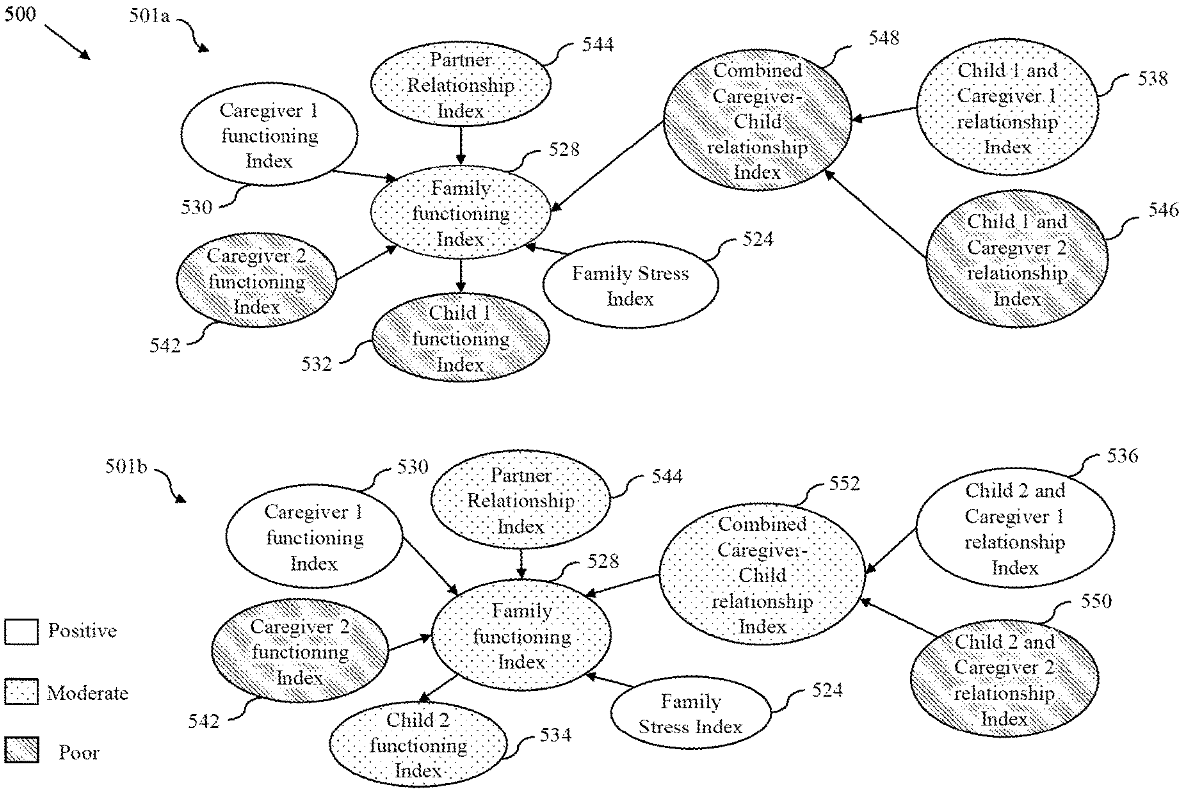
Figure 5H:
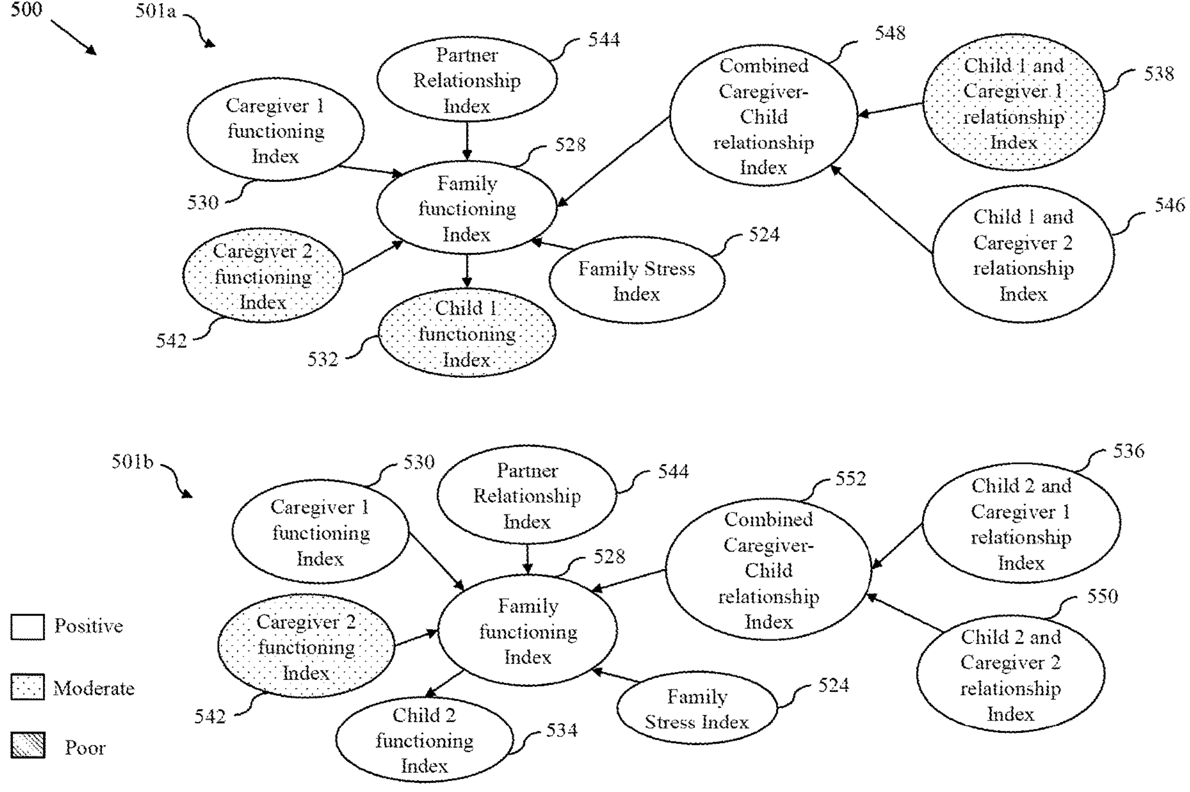

FIGS. 5G-5H, collectively, shows another exemplary embodiment of facilitating online therapeutic services to the family, in accordance with an embodiment of the disclosure. In the exemplary embodiment, caregiver-2's social emotional functioning is impacting a relationship with both children (i.e., the child-1 and the child-2), and the partner (i.e., the caregiver-1). Further, the children's social emotional concerns are raised due to the caregiver-2's issue. The child-1 appears to have additional concerns and may need additional direct care. The issue is severe and quick improvement is prioritized. The data associated with the family is received and indexes are generated. In a scenario 501*a*, of FIG. 5G, generation of the family network index 528 (also referred to as a family functioning index) for the child-1 is shown. In the scenario, the family network index 528, for the child-1, is generated based on the caregiver-1 functioning index 530, a caregiver-2 functioning index 542, the child-1 functioning index 532, the external stress index 524 (i.e., a family stress index), a partner relationship index 544, and a combined caregiver-child relationship index 548. The combined caregiver-child relationship index 548 is generated based on the child-1 and caregiver-1 relationship index 538, and a child-1 and caregiver-2 relationship index 546. In another scenario 501*b*, generation of the family network index 528 (also referred to as a family functioning index) for the child-2 is shown. The family network index 528, for the child-2, is generated based on the caregiver-1 functioning index 530, the caregiver-2 functioning index 542, the child-2 functioning index 534, the external stress index 524 (i.e., a family stress index), the partner relationship index 544, and a combined caregiver-child relationship index 552. The combined caregiver-child relationship index 552 is generated based on the child-2 and caregiver-1 relationship index 536, and a child-2 and caregiver-2 relationship index 550.

Further, a set of recommended therapeutic interventions are generated. The set of interventions include the caregiver-2 mental health treatment, parenting strategies, and the child 1 mental health treatment. The set of online therapeutic services include three sessions of adult mental health support, three sessions for parenting support, and three sessions for child-1 mental health support. The response related to the set of online therapeutic services is monitored. The response includes partial response from the caregiver-2, partial response from the child-1, and full response from the child-2. The revised online therapeutic services include continue with child 1 mental health support.

Further, the indexes are improving, based on the set of online therapeutic services, as shown in FIG. 5H. As shown in the scenario 501*a* of FIG. 5H, the caregiver-2 functioning index 542 is improving from poor to moderate, the child-1 functioning index 532 is improving from poor to moderate, the child-1 and caregiver-2 relationship index 546 is improving from poor to positive, and the combined caregiver-child relationship index 548, for the child 1, is improving from poor to positive. Further, as shown in the scenario 501*b* of FIG. 5H, the child-2 functioning index 534 is improving from moderate to positive, the caregiver-2 functioning index 542 is improving from poor to moderate, the child-2 and caregiver-2 relationship index 550 is improving from poor to positive, and the combined caregiver-child relationship index 552, for the child-2, is improving from moderate to positive. Furthermore, the family network index 528, for the child-1 and child-2 (i.e., as shown in the scenarios 501*a* and 501*b*), is improving from moderate to positive. The revised plan is further generated upon improvement in the family network index. The revised plan includes continuing with the child-1 mental health support.

Figure 5I:
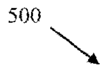
Figure 5I:
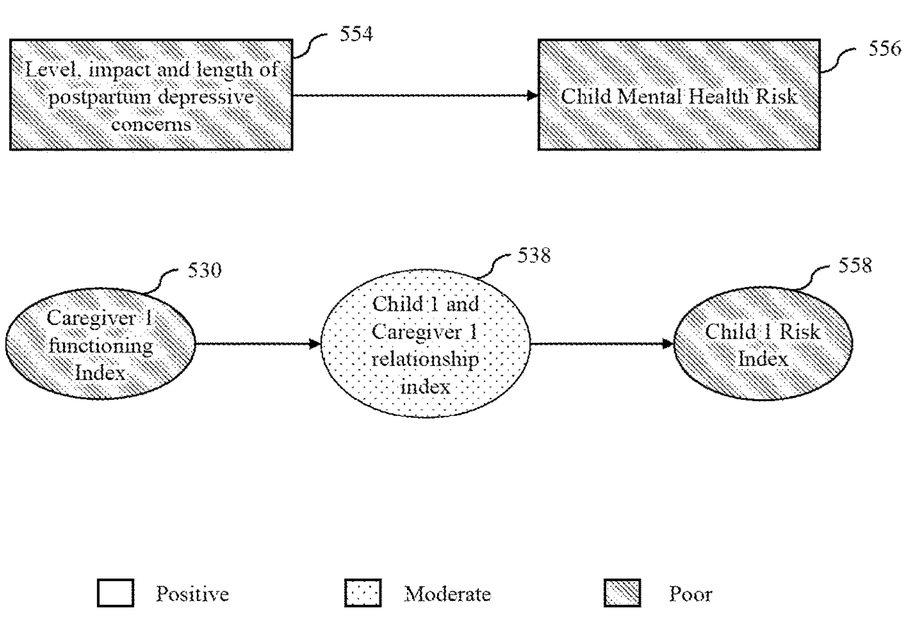
Figure 5J:
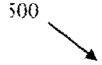
Figure 5J:
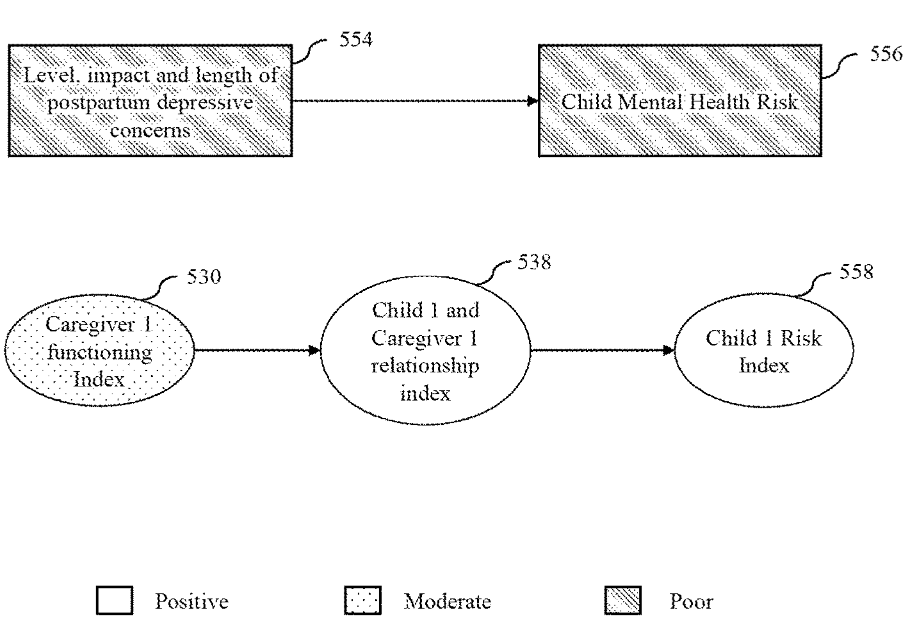

FIGS. 5I-5J, collectively, presents yet another exemplary embodiment of facilitating online therapeutic services to the family, in accordance with an embodiment of the disclosure. In the exemplary embodiment, the caregiver-1 is experiencing postpartum depression that is impacting the child-1 development and future child mental health concerns. In an embodiment, a level, impact, and length of the postpartum depressive concerns 554 leads to the child mental health risk 556. The caregiver-1 functioning index 530 is poor that impacts the child-1 and caregiver-1 relationship index 538 being moderate, and a child-1 risk index 558 being poor. The set of interventions are identified based on the data associated with the family. The set of interventions include the caregiver-1 mental health treatment, and parenting strategies.

Further, the post-treatment estimation of prevention efforts includes cost, mental health burden, and broader socio-developmental impacts. The set of online therapeutic services recommended includes six sessions for adult mental health support, three sessions for parenting support. The response of the set of online therapeutic services includes partial response from the caregiver-1, full response for the caregiver-child relationship. Based on the plans, the indexes are changing as shown in FIG. 5J. The caregiver-1 functioning index 530 is improving from poor to moderate, the child-1 and caregiver-1 relationship index 538 is improving from moderate to positive, and the child-1 risk index 558 is improving from poor to positive. Further, the revised online therapeutic services include continuing with the caregiver-1 mental health support.

Figure 6:
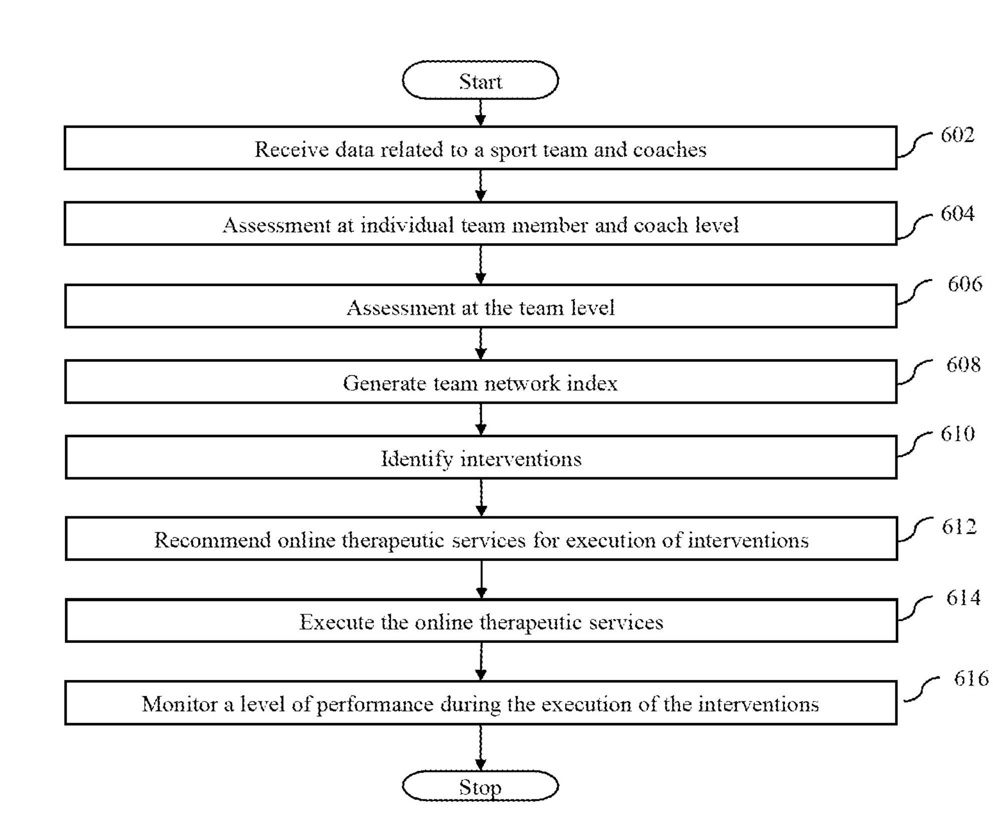
FIG. 6 represents a flow chart that illustrates a method for facilitating online therapeutic services to an athletic sports team, in accordance with an embodiment of the disclosure.

FIG. 6 illustrates a flow chart 600 that illustrates a method for facilitating online therapeutic services to an athletic sport team, in accordance with an embodiment of the present subject matter. In one embodiment, at 602, data associated with the athletic sport team is received. In the embodiment, the athletic sport team is the group of entities. The data comprises the emotion recognition information, and the interaction information relating to one or more coaches and players. The interaction information includes a frequency of interaction, types of interactions, and a video of interaction. The data comprises health records, such as generalized screens like mood and feelings questionnaire, specialized screen like depression: Beck's Depression Inventory, and surgical histories. The data further comprises health or biological data, such as medication dosage and frequency, blood pressure, sleep duration and/or sleep study, heart rate or pulse, stress test, blood tests including for example drug test, physical activity tracking (e.g., exercise, steps, stairs, weights, etc.), and the like. The data further comprises videos of player and coach behavior. The data comprises demographics, including at least years of experience in sport or position, the age, the location, and speed/strength assessments. Further, the data comprises sports performance data, including for example one or more of win/loss record, other individual, and team statistics.

At 604, the data associated with each player and coach is analyzed to generate an entity index for each individual in the sports team. The entity index includes a coach functioning index, a player functioning index, and an external stress index.

At 606, the data associated with the player and coach is analyzed to generate an entity pair index. The entity pair index includes a coach-player dyad relationship indexes, player-player dyad relationship indexes, and a coach relationship index. Further, the coach-player dyad relationship indexes are combined to generate a combined coach-player relationship index.

At 608, the coach functioning index, the player functioning index, the external stress index, the coach-player dyad relationship indexes, the player-player dyad relationship indexes, the coach relationship index, and the combined coach-player relationship index are combined to generate a sport team network index. The sports team network index reflects the functioning of the sports team. The sports team network index may be in multiple forms, including one or more of: numeric, qualitative, ordinal and categorical satisfaction index. Further, subscales include team performance, player performance and/or mental health, position-level performance and/or mental health, coach mental health, dyadic relationships e.g., player 1<->coach 1, player 2<->player 3, and functioning.

At 610, a set of interventions associated with the athletic sport team are identified using an optimization technique. The set of interventions leads can be optimized on any of: distance, velocity, and efficiency.

At 612, a set of online therapeutic services are recommended for execution of the set of interventions. The set of online therapeutic services are recommended to coaches and/or players. The set of online therapeutic services are targeted for direct player services, direct coach services, and direct player-coach services. The set of online therapeutic services include individual and/or group talk therapy, nutrition and sleep management, strength training and/or exercise regime, self-guided programs and/or video programs, supplemented services (e.g., infrequent counseling sessions with digital supplemented), medication/drug management.

At 614, the set of online therapeutic services are executed to improve the level of performance of the group of entities.

At 616, the level of performance of the group of entities is monitored based on the execution of the set of online therapeutic services. Further, the data is refreshed, new interventions are identified, and new online therapeutic services are recommended for the execution of the new interventions.

FIGS. 7A-7G, collectively, represent an exemplary embodiment 700 of facilitating online therapeutic services to the sport team, in accordance with an embodiment of the disclosure. In one embodiment, an entity index related to individuals in the sport team, an entity pair index related to each pair of individuals in the sport team, and a sport team network index are represented as blocks with different patterns in the FIGS. 7A-7G. In the embodiment, a level of performance associated with the entity indexes, the entity pair indexes, and the sport team network index is indicated by the different patterns. In one embodiment, a diagonal lines pattern indicates a poor index (i.e., poor level of performance), a dotted pattern indicates a moderate index (i.e., moderate level of performance), and no pattern (i.e., blank pattern) indicates a positive index (i.e., positive level of performance).

Figure 7A:
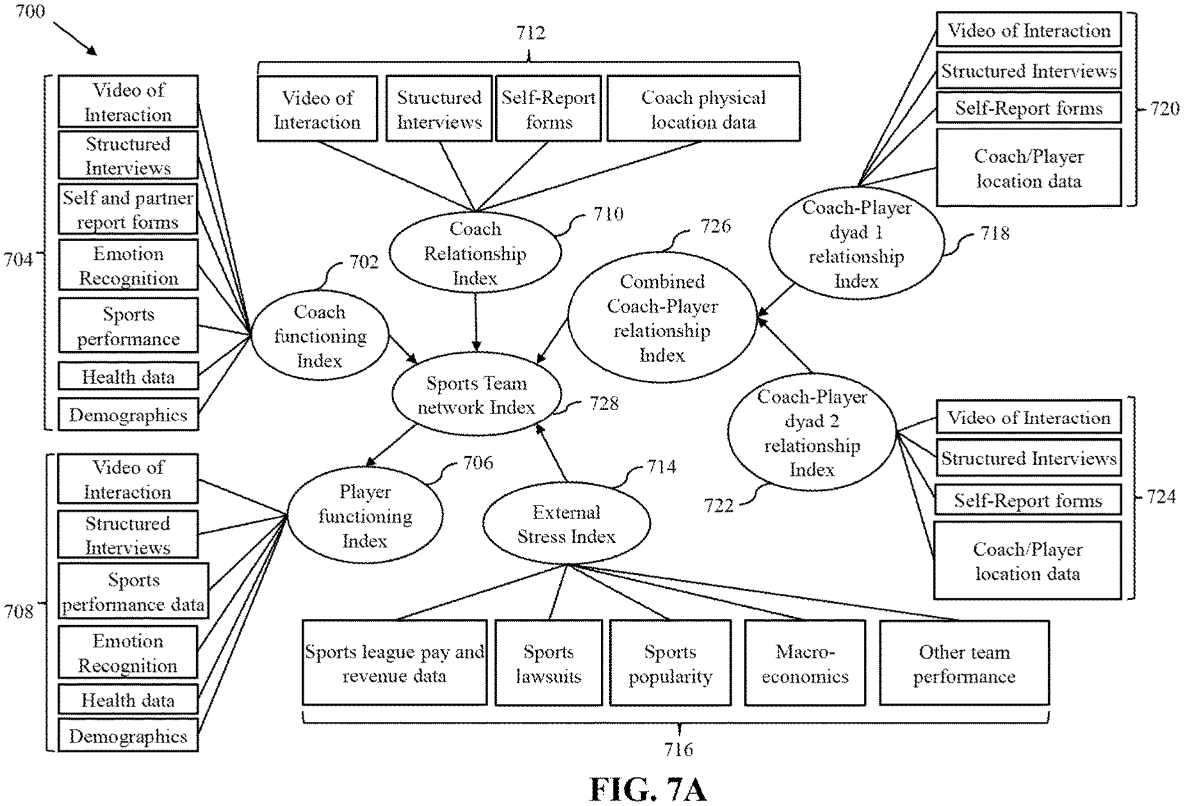
FIGS. 7A-7G, collectively, represent an exemplary embodiment for facilitating online therapeutic services to the athletic sports team, in accordance with an embodiment of the disclosure.

FIG. 7A shows generation of the sports team network, in accordance with an embodiment of the disclosure. In an embodiment, a coach functioning index 702 is generated based on data 704 including video of interactions, structured interviews, self and partner report forms, the emotion recognition information, health records, health data, and demographics of the coach associated with the sport team. Further, a player functioning index 706 is generated based on data 708 including video of interactions, structured interviews, self and partner report forms, the emotion recognition information, health records, health data, and demographics of each player in the sport team. Furthermore, a coach relationship index 710 is further generated based on data 712 including video of interactions, structured interviews, self-report forms and coach location data. An external stress index 714 is generated based on data 716 including, for example, sports league play, revenue data, sport lawsuits, sport popularity, macro-economics and rival team performance.

Furthermore, a coach-player dyad 1 relationship index 718 is generated based on data 720 including video of interactions, structured interviews, self-report forms and location information of the coach and the player. Subsequently, a coach-player dyad 2 relationship index 722 is generated based on data 724 including video of interactions, structured interviews, self-report forms and the location information of the coach and the player. Further, the coach-player dyad 1 relationship index 718 and the coach-player dyad 2 relationship index 722 are combined to generate a combined coach-player relationship index 726. Further, the coach functioning index 702, the player functioning index 706, the coach relationship index 710, the external stress index 714, and the combined coach-player relationship index 726 are used to generate the sport team network index 728.

Figure 7B:
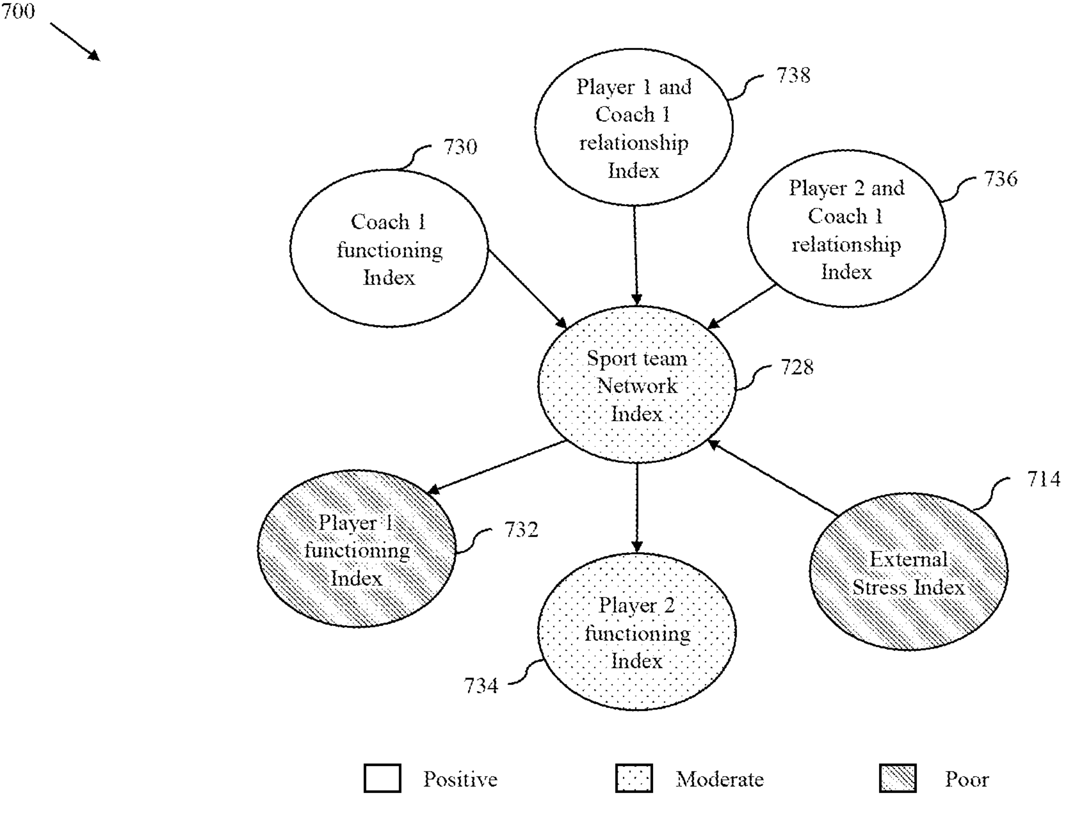
Figure 7C:
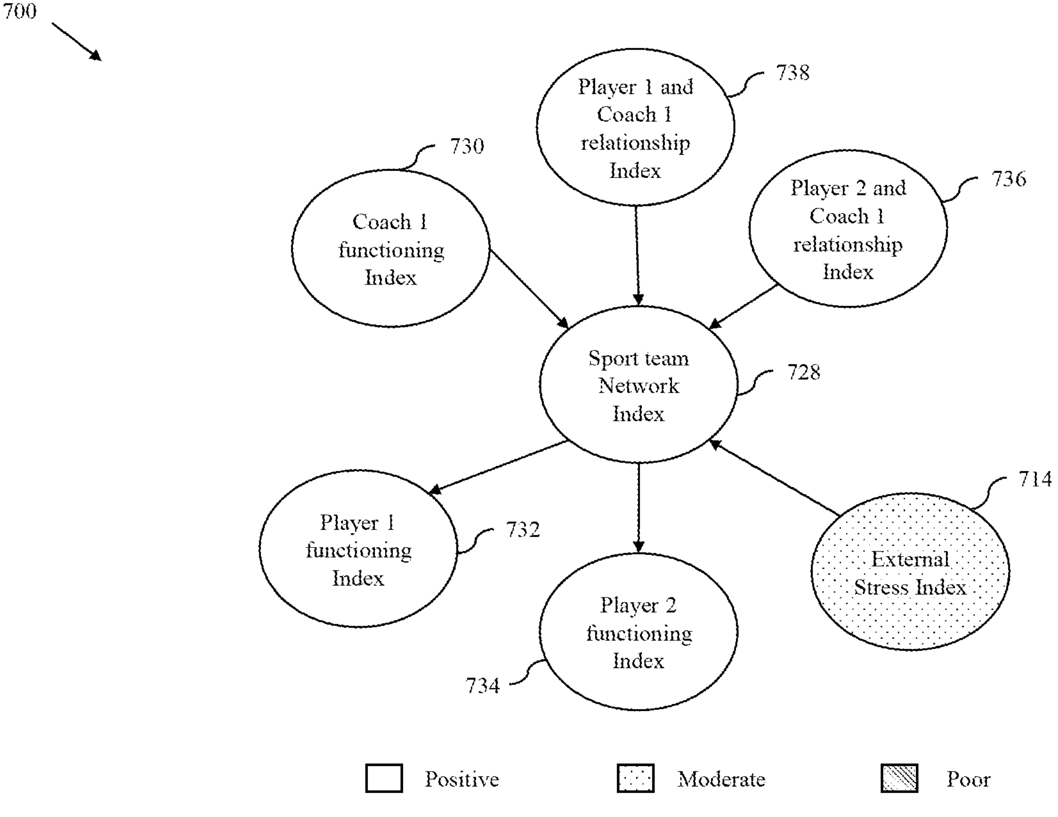

FIGS. 7B-7C, collectively, shows an exemplary embodiment for facilitating online therapeutic services to the sport team. In the embodiment, a player-1 has exhibited major performance issues in the past, that has coincided with the death of a family member and a minor ankle injury. Further, a player-2 has had a minor decline in performance. The sport team has lost the last few games, while the local rival has continued a winning streak. As shown in the FIG. 7B, the sport team network index 728 is generated based on a coach-1 functioning index 730, a player-1 functioning index 732, a player-2 functioning index 734, the external stress index 714, a player-1 and coach-1 relationship index 738, and a player-2 and coach-1 relationship index 736. Further, the player-1 functioning index 732 is poor, the player-2 functioning index 734 is moderate, the external stress index 714 is poor, and hence the sport team network index 728 is moderate. In an embodiment, the data related to the sport team is received. Further, the set of interventions are identified as physical therapy for player-1's ankle, and mental health support for the player-1.

Further, the set of online therapeutic services are recommended to the sport team. The set of online therapeutic services include ten physical therapy sessions for the player-1, and five sessions of psychotherapy for player-1 with focus on grief. The response to the online therapeutic services includes full response from the player-1 and the player-2. Based on the online therapeutic services, the indexes improve as shown in FIG. 7C. The player-1 functioning index 732 is improved from poor to positive, the player-2 functioning index 734 is improved from moderate to positive, the external stress index 714 is improved from poor to moderate, and the sport team network index 728 is improved from moderate to positive. Further, the set of online therapeutic services is revised based on the improvement in the sport team network index 728. The revised online therapeutic services include continuation of physical therapy and psychotherapy for the definite time.

Figure 7D:
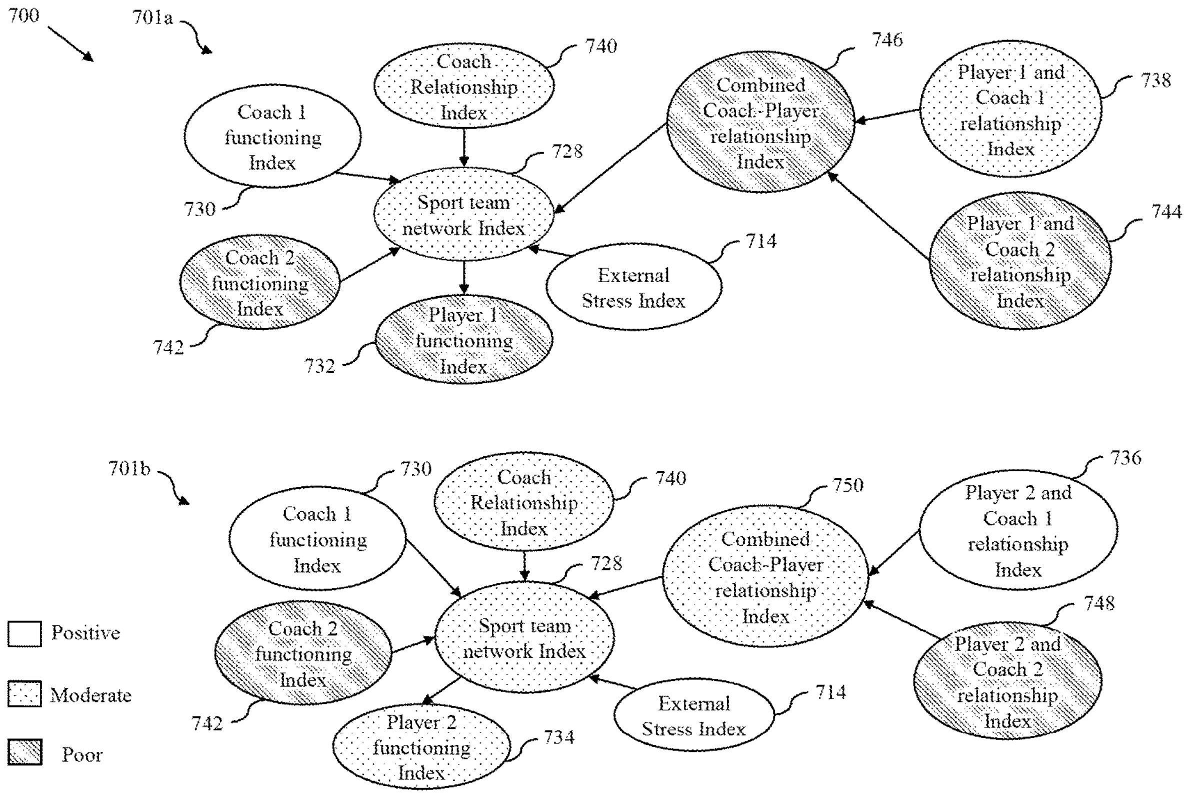
Figure 7E:
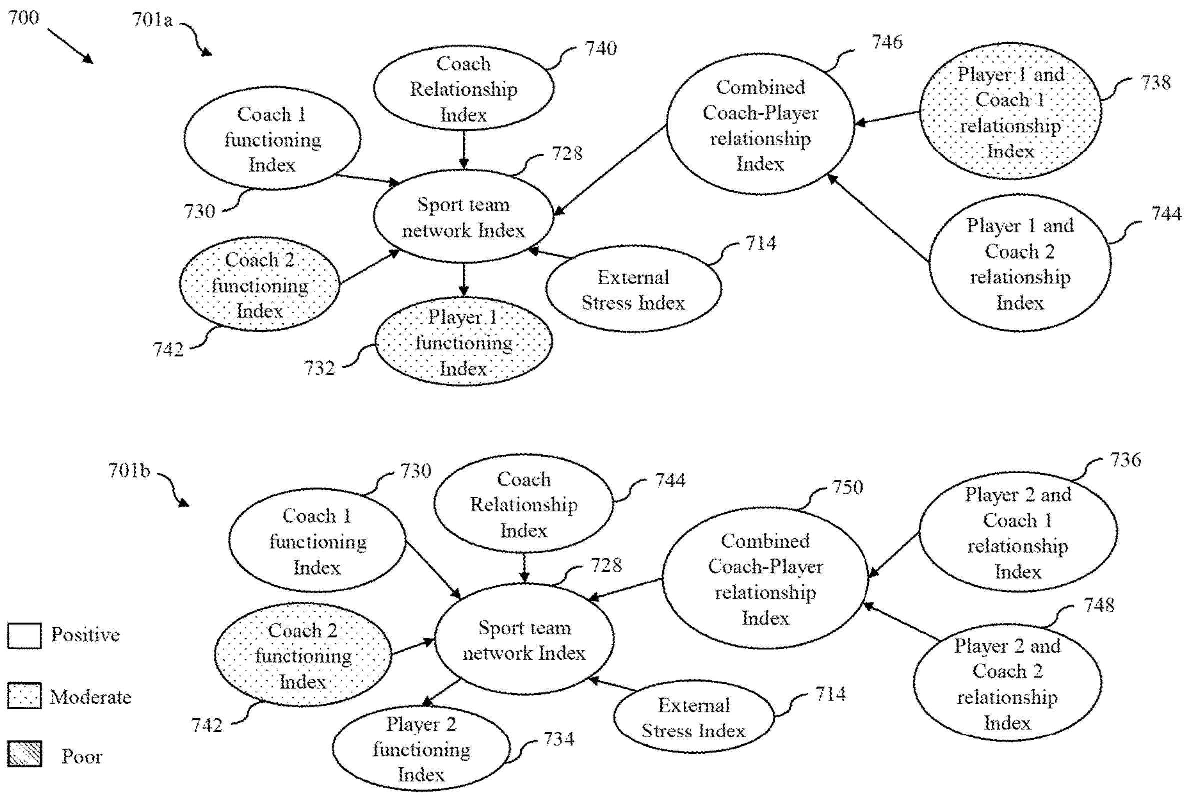

FIGS. 7D-7E, collectively, shows another exemplary embodiment of facilitating online therapeutic services to the sport team, in accordance with an embodiment of the disclosure. In the exemplary embodiment, a coach-2's social emotional functioning is impacting the relationship with players and coaches. Further, the social emotional concerns of the player-1 and the player-2 are raised. The player-1 appears to have additional concerns. The issue is severe and quick improvement is prioritized. In a scenario 701*a*, of FIG. 7D, generation of the sport team network index 728, for the player-1, is shown. The sport team network index 728, for the player-1, is generated based on the coach-1 functioning index 730, a coach-2 functioning index 742, the player-1 functioning index 732, the external stress index 714, a coach relationship index 740, and a combined coach-player relationship index 746. Further, the combined coach-player relationship index 746, for the player-1, is generated based on the player-1 and coach-1 relationship index 738 and a player-1 and coach-2 relationship index 744. In another scenario 701*b*, generation of the sport team network index 728, for the player-2, is shown. The sport team network index 728, for the player-2, is generated based on the coach-1 functioning index 730, a coach-2 functioning index 742, the player-2 functioning index 734, the external stress index 714, the coach relationship index 740, and a combined coach-player relationship index 750. Further, the combined coach-player relationship index 750, for the player-2, is generated based on the player-2 and coach-1 relationship index 736 and a player-2 and coach-2 relationship index 748. The data associated with the sport team is received, and the set of interventions is identified. Further, the set of interventions include the coach-2 talk therapy, coaching strategies, and player-1 talk therapy.

The set of online therapeutic services are further recommended to the sport team to execute the set of interventions. The set of online therapeutic services include three psychotherapy sessions for coach-2, three coaching strategy sessions with entire coaching staff, three psychotherapy sessions for the player-1. The response to the online therapeutic services includes partial for coach-2, partial response for player-1, and full for the player-2.

Further, the indexes change for different entities like coach and players, based on the set of online therapeutic services, as shown in FIG. 7E. As shown in the scenario 701*a* of FIG. 7E, the coach-2 functioning index 742 is improved from poor to moderate, the player-1 functioning index 732 is improved from poor to moderate, the player-1 and coach-2 functioning index 744 is improved form poor to positive, and the combined coach-player relationship index 746, for the player-1, is improved from poor to positive. Further, as shown in the scenario 701*b* of FIG. 7E, the player-2 functioning index 734 is improved from moderate to positive, the coach-2 functioning index 742 is improved from poor to moderate, the player-2 and coach-2 relationship index 748 is improved from poor to positive, and the combined coach-player relationship index 750, for the player-2, is improved from moderate to positive, the coach relationship index 740, for the player-1 and the player-2, is improved from moderate to positive. Furthermore, the sport team network index 728, for player-1 and player-2, is improved from moderate to positive. Further, the set of online therapeutic services is revised based on the improvement in the sport team network. The revised online therapeutic services include continuation of psychotherapy.

Figure 7F:
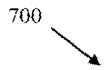
Figure 7F:
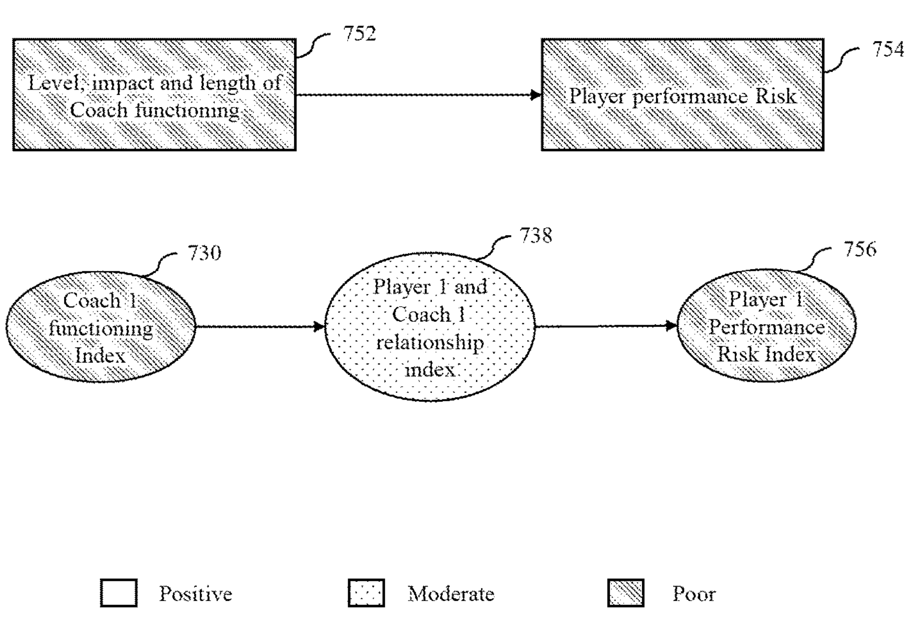
Figure 7G:
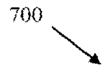
Figure 7G:
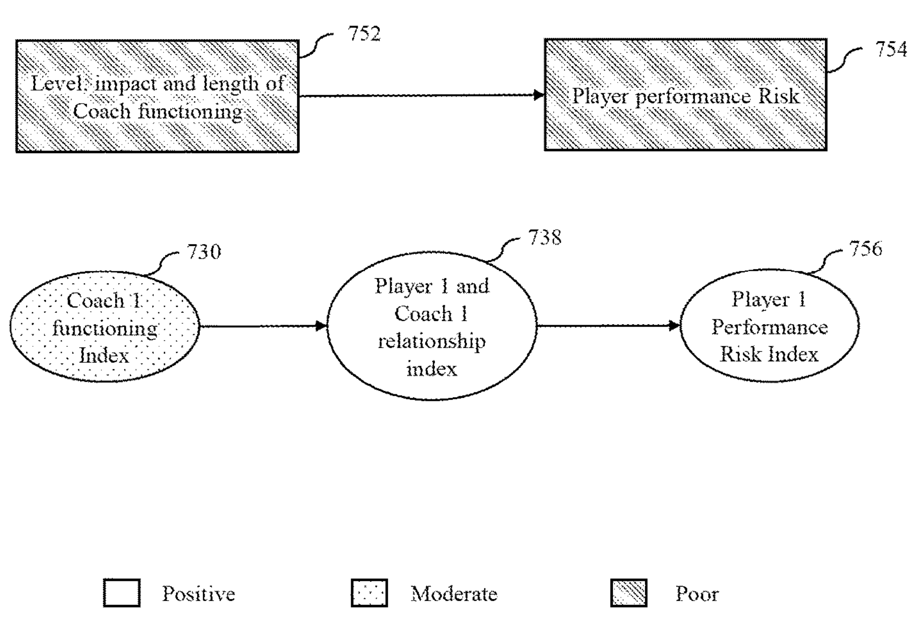

FIGS. 7F-7G shows another exemplary embodiment for facilitating online therapeutic services to the sport team, in accordance with an embodiment of the disclosure. In the exemplary embodiment, after a second losing season, and an inability to partner effectively with a former star player that has left the sport team, the coach-1 is in a poor mental state and ineffective in coaching. Further, the player-1 may join and replace the former star this season. Further, a level, impact, and length of the coach functioning 752 impacts a player performance risk 754. Furthermore, the set of interventions are identified based on the data received related to the sport team. The set of interventions include the coach-1 psychotherapy, and the coach-1 position-relevant coaching.

Further, the set of online therapeutic services recommended for the set of interventions include six psychotherapy sessions with the coach-1, and three position-specific coaching sessions with the coach-1. Further, response of the set of online therapeutic services is monitored. The response comprises partial response from the coach-1, and full response for the coach-player relationship. Based on the set of plans, the coach-1 functioning index 730, the player-1 and coach-1 relationship index 738, and a player-1 performance risk index 756 is improved. The improvement in the indexes is shown in FIG. 7G. The coach 1 functioning index 730 is improved from poor to moderate, the player-1 and coach-1 relationship index 738 is improved from moderate to positive, and the player-1 performance risk index 756 is improved from poor to positive. Further, the set of online therapeutic services is revised based on the improvement in the indexes. The revised online therapeutic services include continuation of psychotherapy for the coach-1.

Figure 8:
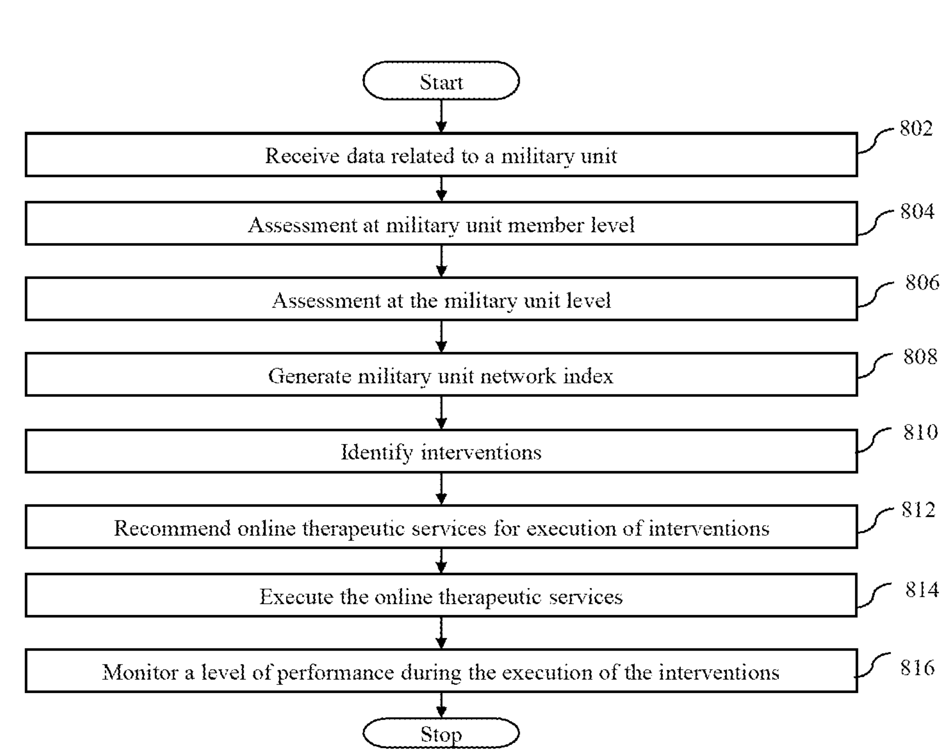
FIG. 8 represents a flow chart that illustrates a method for facilitating online therapeutic services to a military unit, in accordance with an embodiment of the disclosure.

FIG. 8 shows a flow chart 800 that illustrates facilitating online therapeutic services to a military unit, in accordance with an embodiment of the disclosure. In an embodiment, the military unit is the group of entities. At 802, data related to the military unit, including leadership and individuals, is received. The data comprises the emotion recognition data, and the interaction data relating to leadership and soldiers. The interaction data comprises a frequency of interaction, types of interactions and interaction data (e.g., e-mails, messaging). The data further comprises the mental health screen data, such as generalized screens, like mood and feelings questionnaire, specialized screens, like depression: Beck's Depression Inventory. Further, the data comprises health/biological data, such as for example a medication dosage and frequency, blood pressure, heart rate, stress test, sleep duration and/or sleep study, blood tests (including drug tests), other drug tests, physical activity tracking, and other biological data. Furthermore, in some embodiments, the data comprises video data of leadership and individual behavior. Also, the data in some examples comprises the demographics information including years of experience in military, military unit, role, and position. The demographics information further comprises age, an education level, training received, and location.

At 804, an entity index associated with each individual in the military unit is generated based on the analysis of the data. The entity index comprises a leader functioning index, a soldier functioning index and an external stress index.

At 806, an entity pair index related to multiple pairs in the military unit is generated. The entity pair index comprises leader-soldier dyad relationship indexes, soldier-soldier dyad relationship indexes, and a leader relationship index. Further, in one embodiment, the leader-soldier dyad relationship indexes are combined into new index, i.e., a combined leader-soldier relationship index.

At 808, the major indexes (i.e., the entity index, entity pair index, and the combined leader-soldier relationship index) are combined to create a military unit network index, that reflects the functioning of the military unit. The military unit network index (or group network index) may take multiple forms, including numeric, qualitative, ordinal and categorical. In addition to the military unit network index providing an overall score, various subordinate indicators, such as subscales or subscores may be used in identifying the recommended intervention. These subscales or subscores may include, for example, team performance (e.g., combat success, lack of losses), individual performance and/or mental health, role-level performance and/or mental health, leadership performance and/or mental health, dyadic relationships for example, soldier 1<->leader/commander 1 and soldier 2<->soldier 3, and functioning.

At 810, a set of interventions are identified for the miliary unit using the optimization technique. The set of interventions are evaluated through use of the group network index, using the metrics of distance, velocity, and efficiency. The set of interventions are delivered to the leadership and/or individuals in the group.

At 812, a set of online therapeutic services related to the set of interventions are recommended to the military unit. The set of interventions target direct individual services, direct leadership services, and direct leadership-individual services. The set of plans include individual and/or group psychotherapy, nutrition and sleep management, self-guided programs, and supplemented services (e.g., infrequent counseling sessions with digital supplementation).

At 814, the set of online therapeutic services are executed and delivered to improve the level of performance of the group of entities 106*a*-106*n*. In some embodiment, therapeutic services are also delivered in-person.

At 816, the level of performance is monitored based on execution of the set of online therapeutic services. Further, the data is refreshed, new interventions are identified, and new online therapeutic services are recommended for the execution of the new interventions.

FIGS. 9A-9G, collectively, represent an exemplary embodiment 900 of facilitating online therapeutic services to the military unit, in accordance with an embodiment of the disclosure. In one embodiment, an entity index related to individuals in the military unit, an entity pair index related to each pair of individuals in the military unit, and a military unit network index are represented as blocks with different patterns in the FIGS. 9A-9G. In the embodiment, a level of performance associated with the entity indexes, the entity pair indexes, and the military unit network index is indicated by the different patterns. In one embodiment, a diagonal lines pattern indicates a poor index (i.e., poor level of performance), a dotted pattern indicates a moderate index (i.e., moderate level of performance), and no pattern (i.e., blank pattern) indicates a positive index (i.e., positive level of performance).

Figure 9A:
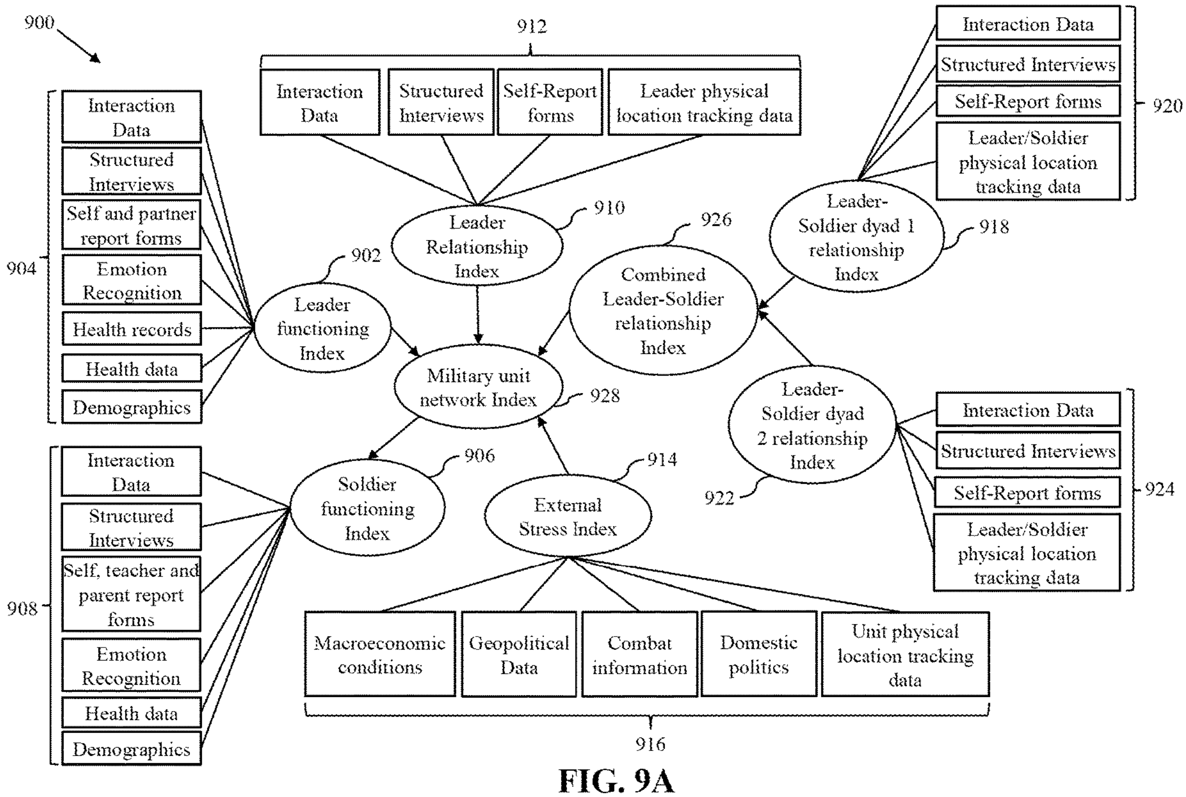
FIGS. 9A-9G, collectively, represent an exemplary embodiment for facilitating online therapeutic services to the military unit, in accordance with an embodiment of the disclosure.

FIG. 9A shows generation of the military unit network, in accordance with an embodiment of the disclosure. In an embodiment, a leader functioning index 902 is generated based on data 904 including video of interactions, structured interviews, self and partner report forms, emotion recognition information, health records, health data (such as blood tests, physical activity tracking and the like), and demographics of the leader present in the military unit. Further, a soldier functioning index 906 is generated based on data 908 including video of interactions, structured interviews, self and partner report forms, emotion recognition information, health records, health data, and demographics of each soldier in the military unit. Furthermore, a leader relationship index 910 is generated based on the data 912 including interaction data, structured interviews, self-report forms, and leader location data. An external stress index 914 is generated based on the data 916 including macro-economic conditions, geopolitical data, combat information, domestic politics, and unit physical location tracking data.

Furthermore, a leader-soldier dyad 1 relationship index 918 is generated based on data 920 including video of interactions, structured interviews, self-report forms, and location information of the leader and the soldier. Similarly, a leader-soldier dyad 2 relationship index 922 are generated based on data 24 including video of interactions, structured interviews, self-report forms, and location information of the leader and the soldier. Further, the leader-soldier dyad 1 relationship index 918 and the leader-soldier dyad 2 relationship index 922 are combined to generate a combined leader-soldier relationship index 926. Further, the leader functioning index 902, the soldier functioning index 906, the leader relationship index 910, the external stress index 914, and the combined leader-soldier relationship index 926 are used to generate the military unit network index 928.

Figure 9B:
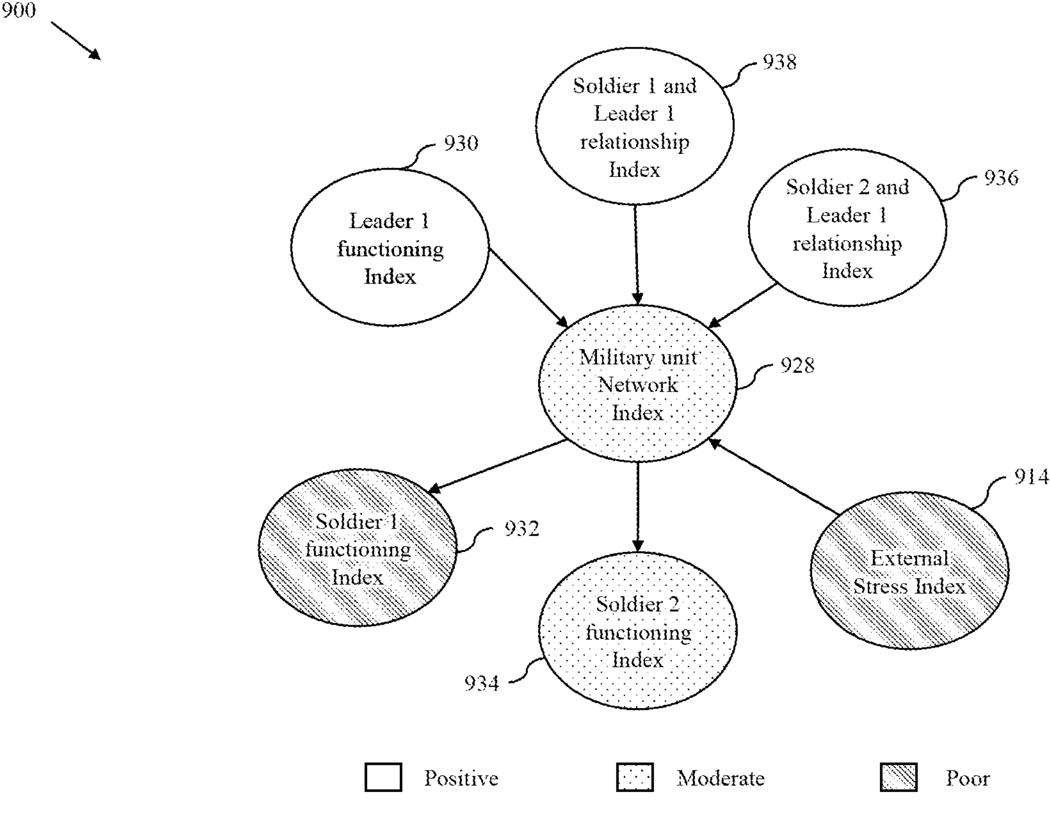
Figure 9C:
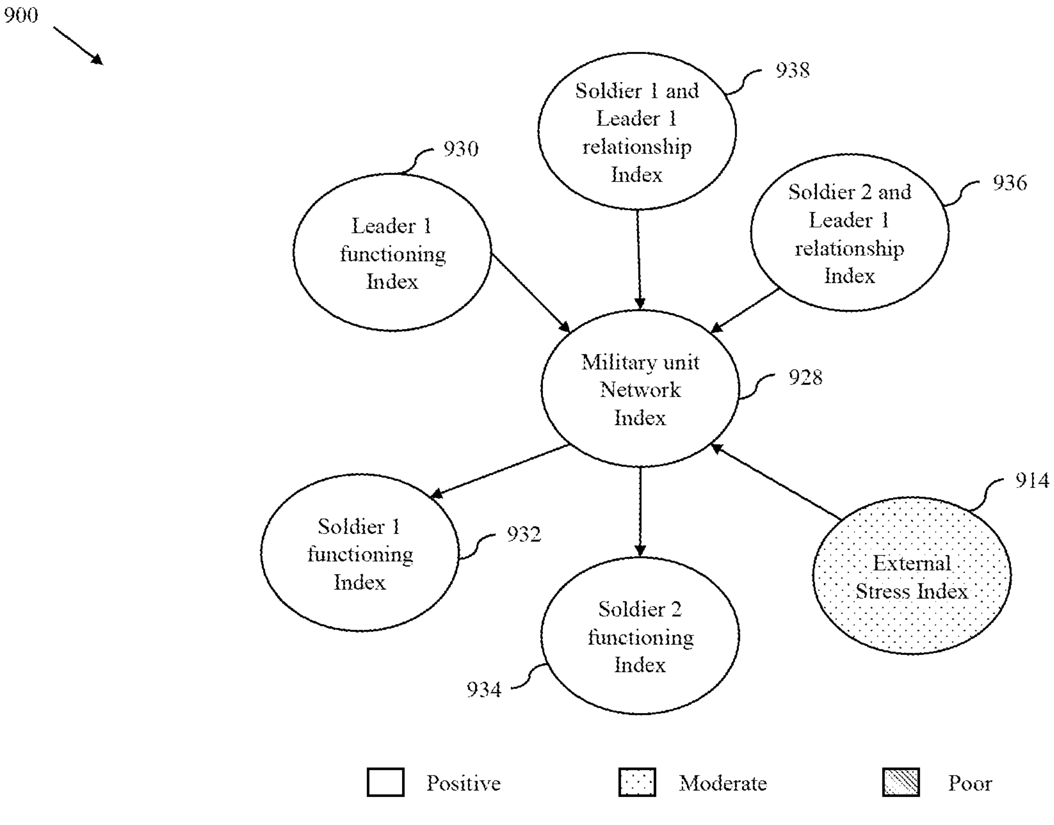

FIGS. 9B-9C, collectively, represent an exemplary embodiment of facilitating online therapeutic services to the military unit, in accordance with an embodiment of the disclosure. In the exemplary embodiment, the military unit is facing stress due to a return from combat. The soldier-1 is having impairing mental health concerns with a potential PTSD diagnosis, and the soldier-2 has struggled recently as well, in part due to interactions with the soldier-1. The military unit network index 928 is generated based on a leader-1 functioning index 930, a soldier-1 functioning index 932, a soldier-2 functioning index 934, the external stress index 914, a soldier-1 and leader-1 relationship index 938, and a soldier-2 and leader-1 relationship index 936. In an embodiment, data associated with the military unit is received. Further, the set of interventions are identified. The set of interventions include psychotherapy for the soldier-1, and psychotherapy for the soldier-2.

The set of online therapeutic services are recommended for execution of the set of interventions. The set of online therapeutic services include four psychotherapy sessions for the soldier-1 with focus on PTSD, and two psychotherapy sessions for the soldier-2. The response to the set of online therapeutic services is monitored over time. The response is positive for the soldier-1 and the soldier-2. Based on the response, the functioning index improves as shown in the FIG. 9C. The soldier-1 functioning index 932 improves from poor to positive, the soldier-2 functioning index 934 improves from moderate to positive, the external stress index 914 improves from poor to moderate, and the military unit network index 928 improves from moderate to positive. Further, the set of online therapeutic services is revised based on the response from the military unit. The revised online therapeutic services include continued psychotherapy for the soldier-1. Further, the data is refreshed, and the process is repeated.

Figure 9D:
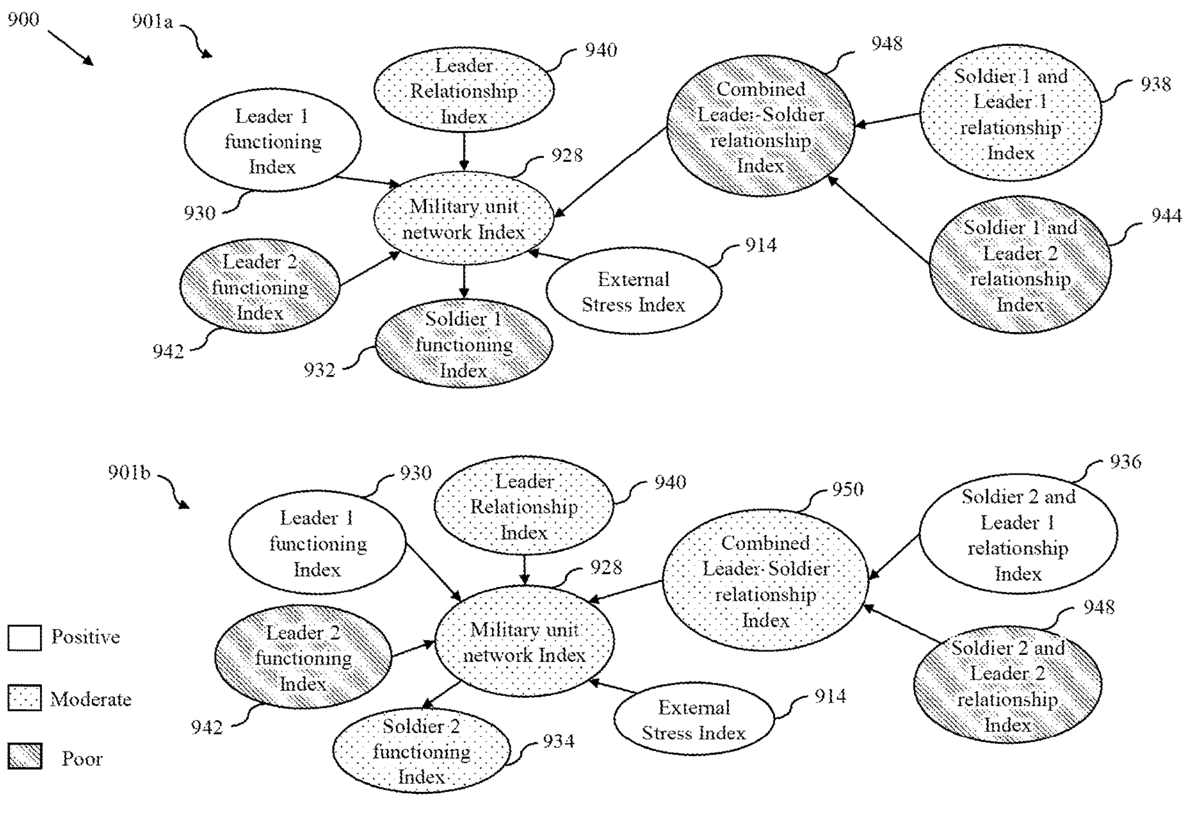
Figure 9E:
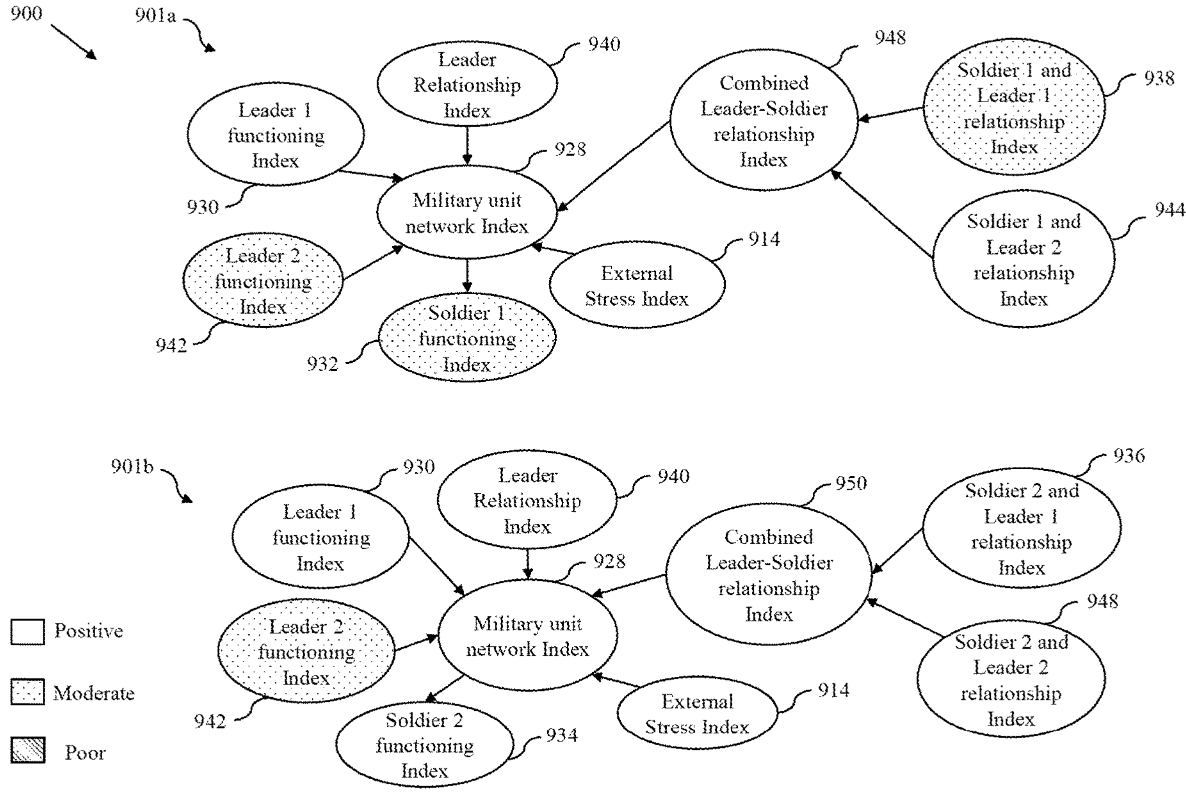

FIGS. 9D-9E, collectively, represent another exemplary embodiment for facilitating online therapeutic services to the military unit, in accordance with an embodiment of the disclosure. In the exemplary embodiment, leader-2's social emotional functioning is impacting the relationship with soldiers and other leaders. Further, the social emotional concerns of the soldier-1 and the soldier-2 are raised due to leader-2's issue. The soldier-1 appears to have additional concerns. The issue is severe and quick improvement is prioritized. In a scenario 901*a*, of the FIG. 9D, generation of the military unit network index 928, for the soldier-1, is shown. The military unit network index 928, for the soldier-1, is generated based on the leader-1 functioning index 930, the soldier-1 functioning index 932, a leader-2 functioning index 942, the external stress index 914, a leader relationship index 940, and a combined leader-soldier relationship index 946. The combined leader-soldier relationship index 946, for the soldier-1, is generated based on the soldier-1 and leader-1 relationship index 938, and a soldier-1 and leader-2 relationship index 944. In a scenario 901*b*, of FIG. 9D, generation of the military unit network index 928, for the soldier-2, is shown. The military unit network index 928, for the soldier-2, is generated based on the leader-1 functioning index 930, the soldier-2 functioning index 934, the leader-2 functioning index 942, the external stress index 914, the leader relationship index 940, and a combined leader-soldier relationship index 950. The combined leader-soldier relationship index 950, for the soldier-2, is generated based on the soldier-2 and leader-1 relationship index 936, and a soldier-2 and leader-2 relationship index 948.

Further, the set of interventions are identified based on analysis of the data associated with the military unit. The set of interventions include leader-2 psychotherapy, leadership strategy training, and soldier-1 psychotherapy.

Furthermore, the set of plans for online therapeutic services for executing the set of interventions is recommended. The set of online therapeutic services include four psychotherapy sessions for the leader-2, two leadership strategy sessions with all of leadership, and four psychotherapy sessions for the soldier-1. The response for the online therapeutic services is monitored over the time. The response includes partial response from the leader-2 and the soldier-1, and full response from the soldier-2.

Based on the response, the functioning in the indexes occurs as shown in the FIG. 9E. As shown in the scenario 901*a*, of the FIG. 9E, the leader-2 functioning index 942 for soldier-1 improves from poor to moderate, the soldier-1 functioning index 932 improves from poor to moderate, the leader relationship index 940, for the soldier-1, improves from moderate to positive, the soldier-1 and leader-2 relationship index 944 improves from poor to positive, and the combined leader-soldier relationship index 946, for the soldier-1, improves from poor to positive. Further, as shown in the scenario 901*b* of the FIG. 9E, the leader-2 functioning index 942 improves from poor to moderate, the soldier-2 functioning index 934 improves from moderate to positive, the soldier-2 and leader-2 relationship index 948 improves from poor to positive, the leader relationship index 940, for the soldier-2, improves from moderate to positive, and the combined leader soldier relationship index 950, for the soldier-2, improves from moderate to positive. Furthermore, the military unit network index 928, for the soldier-1 and soldier-2, improves from moderate to positive. Further, the revised online therapeutic services for the military unit includes continuing of the psychotherapy.

Figure 9F:
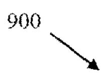
Figure 9F:
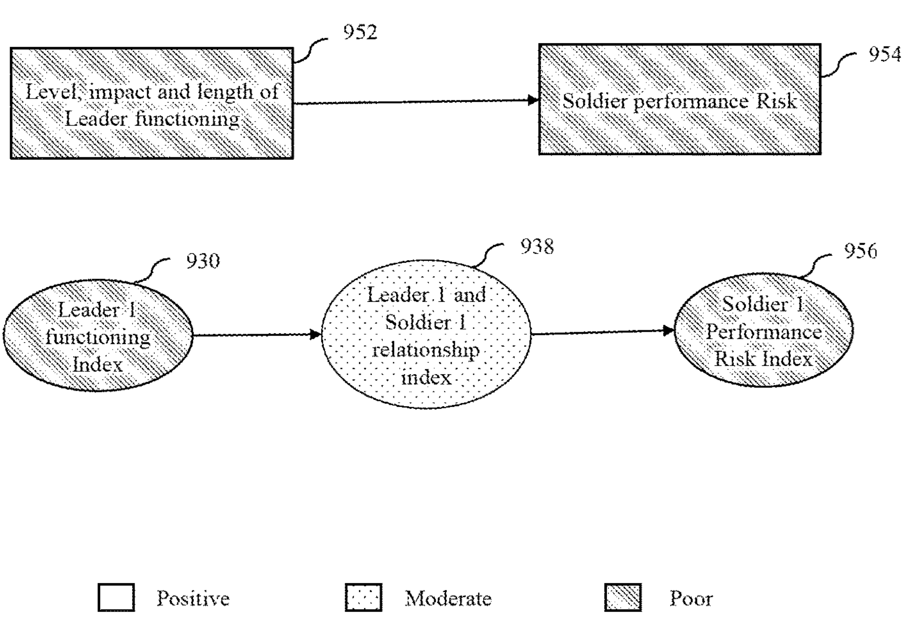
Figure 9G:
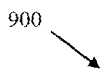
Figure 9G:
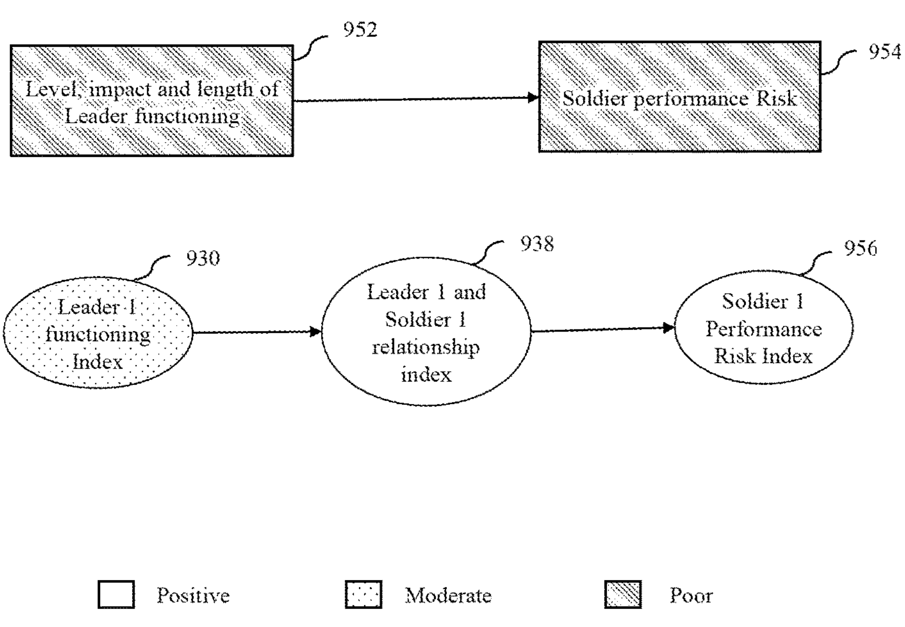

FIGS. 9F-9G, collectively, represents yet another exemplary embodiment for facilitating online therapeutic services to the military unit, in accordance with an embodiment of the disclosure. In the exemplary embodiment, the unit lost a number of soldiers in combat, and an inability to partner effectively with a former soldier that was killed in action, the leader-1 is in a poor mental state and ineffective in leading soldiers of similar rank. The soldier-1 may join and replace the former soldier this year. In an embodiment, a level, impact and length of the leader functioning 952 is leading to a soldier performance risk 954. Further, the set of interventions are identified based on analysis of the data. The set of interventions include leader-1 psychotherapy, and leader-1 rank-relevant coaching.

Further, the set of online therapeutic services include six psychotherapy sessions with the leader-1, and three rank-specific coaching sessions with the leader-1. The response for the set of plans is monitored over the time. The response includes partial response from the leader-1, and full response for the leader-soldier relationship. Based on the response, the improvement in the indexes occurs as shown in the FIG. 9G. The leader-1 functioning index 930 is improved from poor to moderate, the leader-1 and soldier-1 relationship index 938 is improved from moderate to positive, and a soldier-1 performance risk index 956 is improved from poor to positive. Further, the revised online therapeutic services include continuing with leader-1 mental health support.

Figure 10:
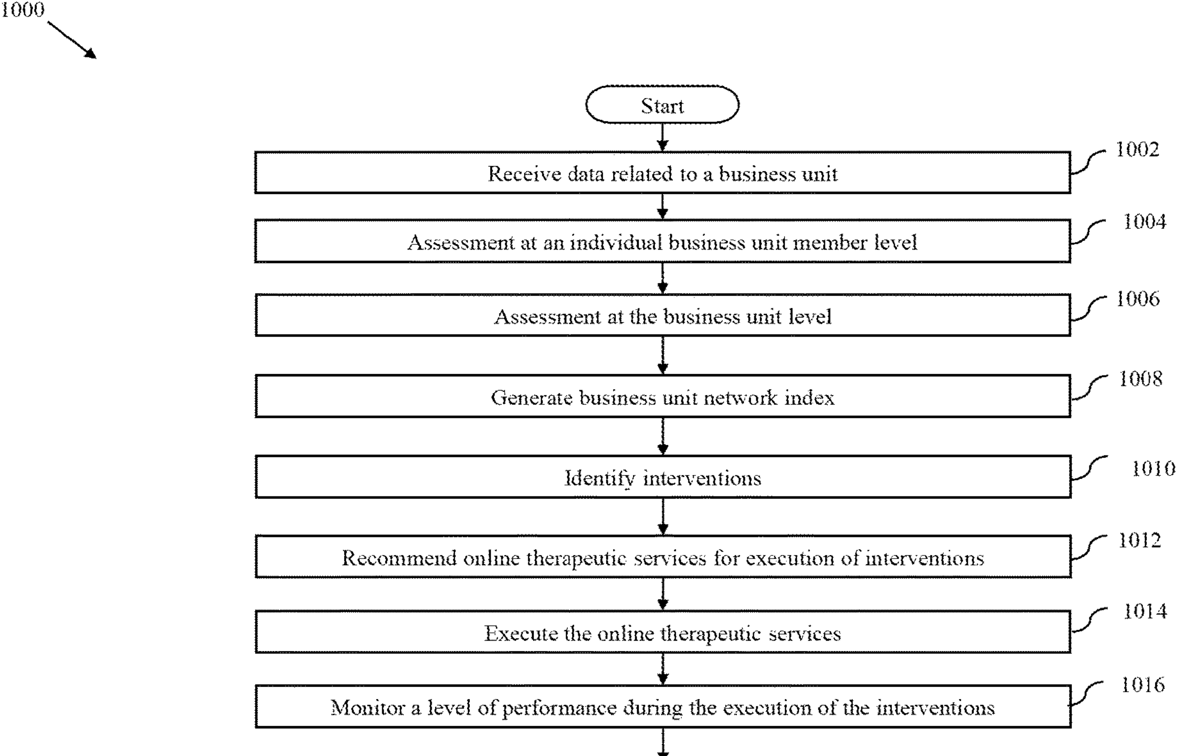
FIG. 10 represents a flow chart that illustrates a method for facilitating online therapeutic services to a business unit, in accordance with an embodiment of the disclosure.

FIG. 10 represents a flow chart 1000 that illustrates a method for facilitating online therapeutic services to a business unit at corporation, in accordance with an embodiment of the disclosure. At 1002, data related to the business unit is received by a server system. The data comprises, for example, emotion recognition data, and interaction data relating to managers and data on individual contributors. The interaction data includes a frequency of interaction, and types of interactions and the interaction data itself (e.g., e-mail). The data comprises mental health screen data, such as generalized screens like mood and Feelings Questionnaire, and Specialized screens, like Depression: Beck's Depression Inventory. The data may further comprise video/voice data of manager and individual contributor behavior. Further, the data comprises demographics, including years of experience in field, corporation, department, and role/title. In some embodiments, the demographic data further comprises a location, team and unit Key Performance Indicators, performance reviews, and client report forms.

At 1004, the data associated with the business unit is analyzed to generate an entity index for each individual in the business unit. The entity index comprise manager functioning index, an Individual Contributor (IC) functioning index, and an external stress index.

At 1006, an entity pair index is generated for each pair of the business unit based on analysis of the data. The entity pair index includes manager-individual contributor dyad relationship indexes, individual contributor-individual contributor dyad relationship indexes, and manager relationship index. Further, the manager-individual contributor dyad relationship indexes are combined to generate a combined manager-individual contributor relationship index.

At 1008, the entity index of each individual, the entity pair indexes, and the combined manager-individual contributor relationship index are combined to create a business unit network index. The business unit network index reflects the functioning of the business unit. The business unit network index may be in multiple forms, such as numeric, qualitative, ordinal and categorical. Further, in addition to the business unit network index, subscales or subscores may be used by the system to recommend services. These subscales or subscores include, for example, business unit team performance (e.g., timely completion of projects, revenue, profit), individual contributor performance and/or mental health, role-level performance and/or mental health, manager performance and/or mental health, dyadic relationships such as individual contributor 1<->manager 1 and individual contributor 2<->individual contributor 3, satisfaction, and functioning.

At 1010, a set of interventions are identified using the optimization technique. The set of interventions leads to best outcomes with respect to the unit network index, measured by metrics of distance, velocity, and efficiency. The set of intervention are delivered to managers and/or individual contributors.

At 1012, a set of online therapeutic services associated with the set of interventions are recommended. The set of interventions target direct manager services, direct individual contributor services, and direct manager-individual contributor services. The set of online therapeutic services include, for example, individual and/or group psychotherapy or counseling, nutrition management, self-guided programs, and supplemental services (e.g., infrequent counseling sessions with digital content supplementation).

At 1014, the set of online therapeutic services is executed to improve the level of performance. Online therapeutic services are delivered using computers over private or public networks. In some embodiments, offline services are provided.

At 1016, the level of performance is monitored based on the execution of the set of online therapeutic services. Further, the data is refreshed, new interventions are identified, and new online therapeutic services are recommended for the execution of the new interventions.

FIGS. 11A-11G, collectively, represent an exemplary embodiment 1100 of facilitating online therapeutic services to the business unit, in accordance with an embodiment of the disclosure. In one embodiment, an entity index related to individuals in the business unit, an entity pair index related to each pair of individuals in the business unit, and a business unit network index are represented with different patterns in the FIGS. 11A-11G. In the embodiment, a level of performance associated with the entity indexes, the entity pair indexes, and the business unit network index is indicated by the different patterns. In one embodiment, a diagonal lines pattern indicates a poor index (i.e., poor level of performance), a dotted pattern indicates a moderate index (i.e., moderate level of performance), and no pattern (i.e., blank pattern) indicates a positive index (i.e., positive level of performance).

Figure 11A:
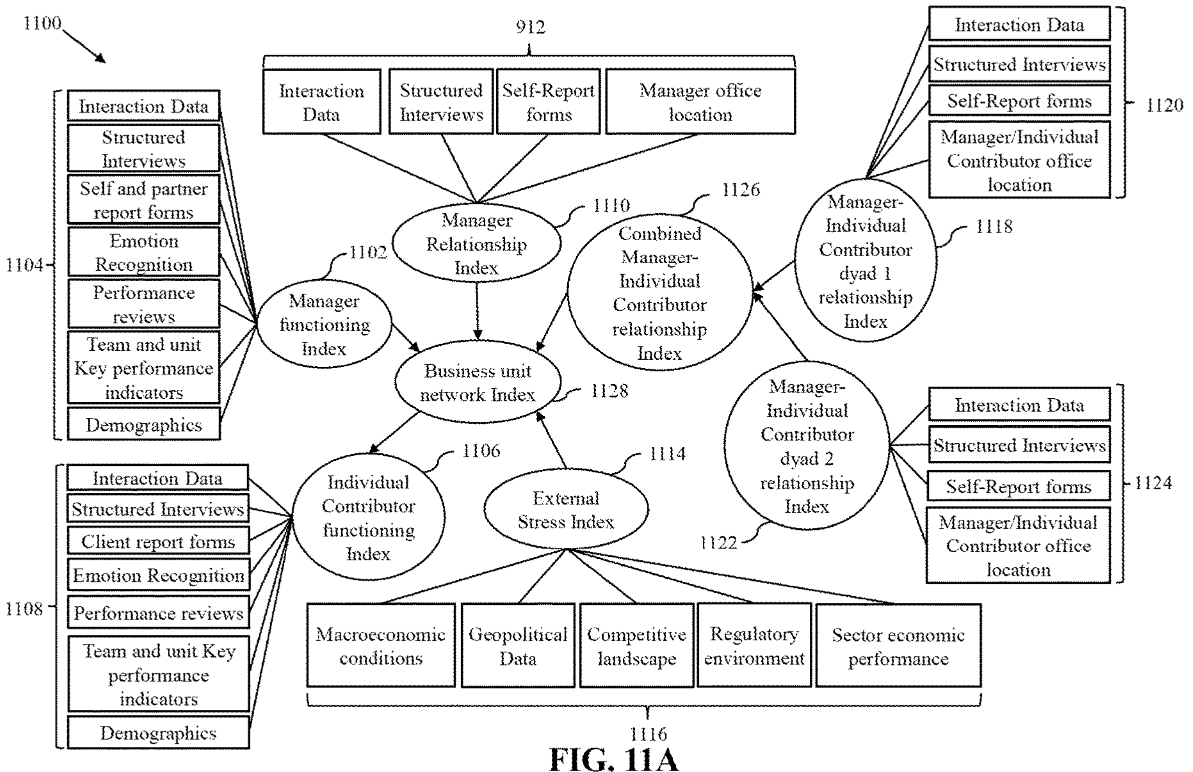
FIGS. 11A-11G, collectively, represent an exemplary embodiment for facilitating online therapeutic services to the business unit, in accordance with an embodiment of the disclosure.

FIG. 11A shows generation of a business unit network, in accordance with an embodiment of the disclosure. In an embodiment, a manager functioning index 1102 is generated based on data 1104 including interaction data, structured interviews, self and partner report forms, emotion recognition information, performance reviews, team and unit Key Performance indicators, and demographics of the manager associated with the business unit.

Further, an individual contributor functioning index 1106 is generated based on the gathered data 1108 including interaction data, structured interviews, self and partner report forms, emotion recognition information, performance reviews, team and unit Key Performance indicators, and demographics of each individual contributor in the business unit. Furthermore, a manager relationship index 1110 is generated based on data collected manager data or leader data 912 including interaction data, the structured interviews, self-report forms and a manager office location. An external stress index 1114 is generated based on received outside or external forces data 1116 including macro-economic conditions, geopolitical data, competitive landscape, regulatory enforcement, and sector economic performance.

Furthermore, a manager-individual contributor dyad 1 relationship index 1118 is generated based on gathered relationship 1 data 1120 including interaction data, structured interviews, self-report forms, and location information of the manager and individual contributor. Similarly, a manager-individual contributor dyad 2 relationship index 1122 is generated based on gathered relationship 2 data 1124 including the interaction data, the structured interviews, the self-report forms and the location information of the manager and the individual contributor. Further, the manager-individual contributor dyad 1 relationship index 1118, and the manager-individual contributor dyad 2 relationship index 1122 are combined to generate a combined manager-individual contributor relationship index 1126. Further, the manager functioning index 1102, the individual-contributor functioning index 1106, the manager relationship index 1110, the external stress index 1114, and the combined manager-individual contributor relationship index 1126 are used to generate the business unit network index 1128.

Figure 11B:
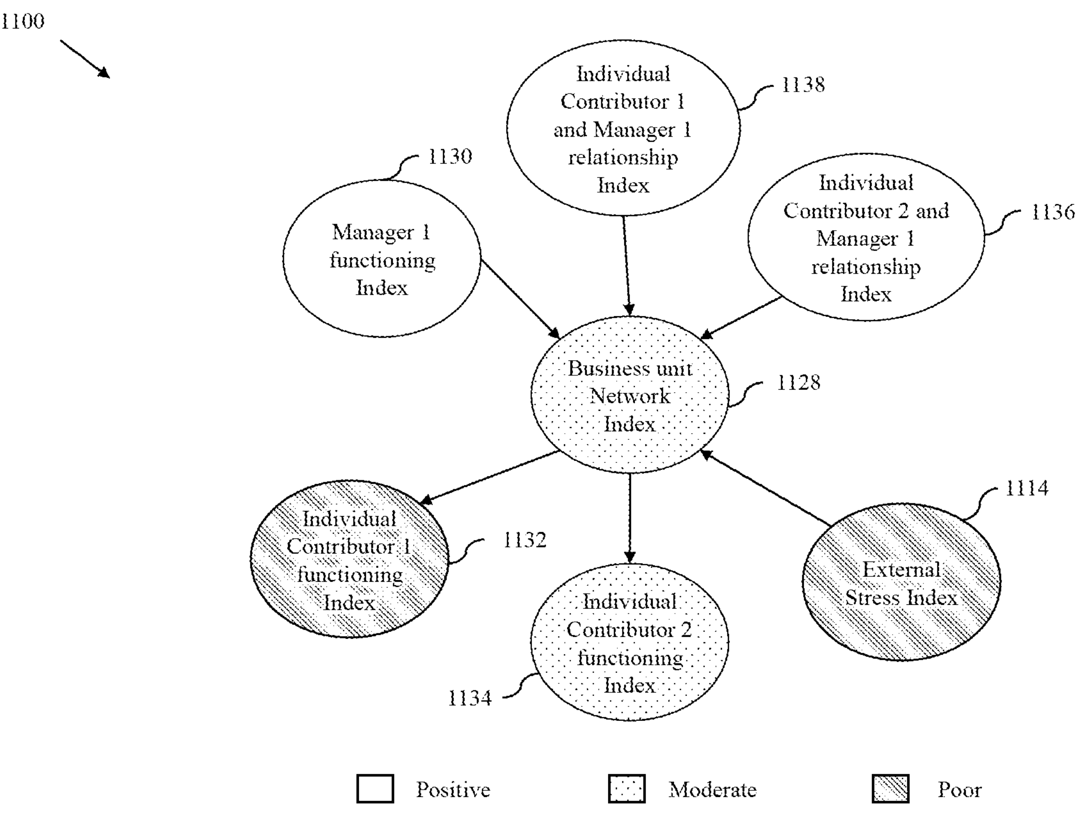
Figure 11C:
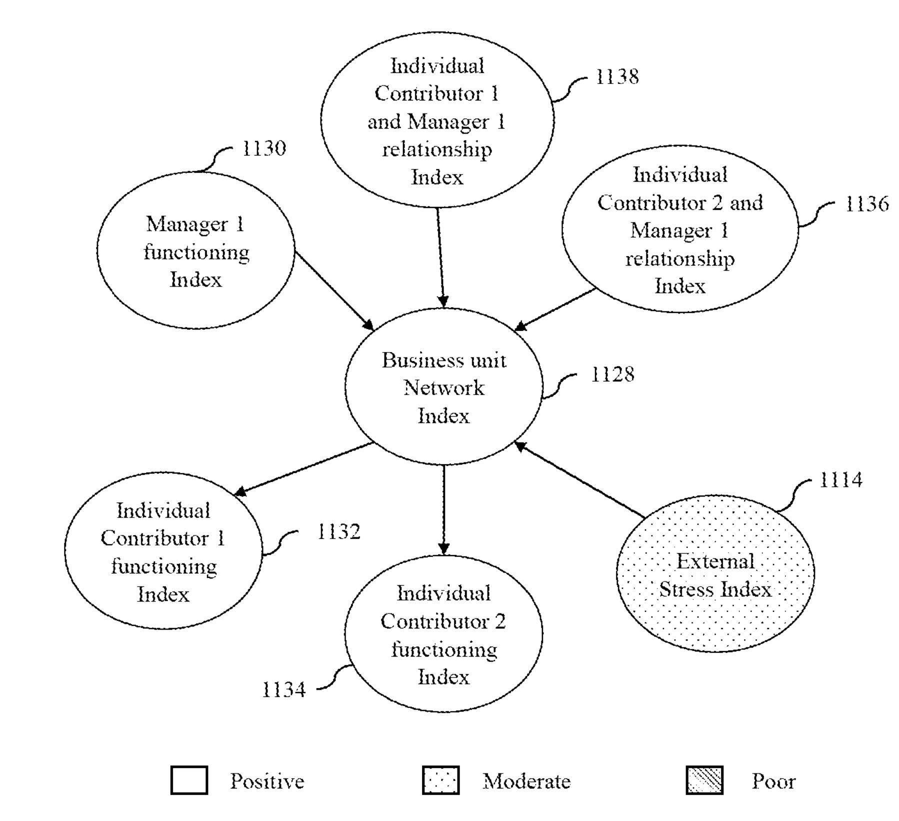

FIGS. 11B-11C, collectively, shows an exemplary embodiment for facilitating online therapeutic services to a business unit, in accordance with an embodiment of the disclosure. In the embodiment, the business unit is facing stress due to an increasingly competitive landscape and missing revenue targets in a last quarter. In the embodiment, an individual contributor-1 is having performance concerns and missed sales targets. Further, an individual contributor-2 has struggled due to supporting the individual contributor-1. In an embodiment, the business unit network index 1128 is generated based on a manager-1 functioning index 1130, an individual contributor-1 functioning index 1132, an individual contributor-2 functioning index 1134, the external stress index 1114, an individual contributor-1 and manager-1 relationship index 1138, and an individual contributor-2 and manager-1 relationship index 1136. Further, the set of interventions are identified based on the data. The set of interventions comprise intensive feedback sessions for the individual contributor-1, and psychotherapy for the individual contributor-2.

Further, the set of online therapeutic services for execution of the set of interventions is recommended. The set of online therapeutic services include four intensive feedback sessions for individual contributor-1, and two psychotherapy sessions for individual contributor-2. The response related to the set of online therapeutic services is monitored over the time. The response includes full response for both the individual contributor-1 and the individual contributor-2. Based on the response, the functioning index improves as shown in the FIG. 11C. The individual contributor-1 functioning index 1132 improves from poor to positive, the individual contributor-2 functioning index 1134 improves from moderate to positive, the external stress index 1114 improves from poor to moderate, and the business unit network index 1128 improves from moderate to positive. Further, the revised online therapeutic services include continued less intensive feedback sessions for the individual contributor-1.

Figure 11D:
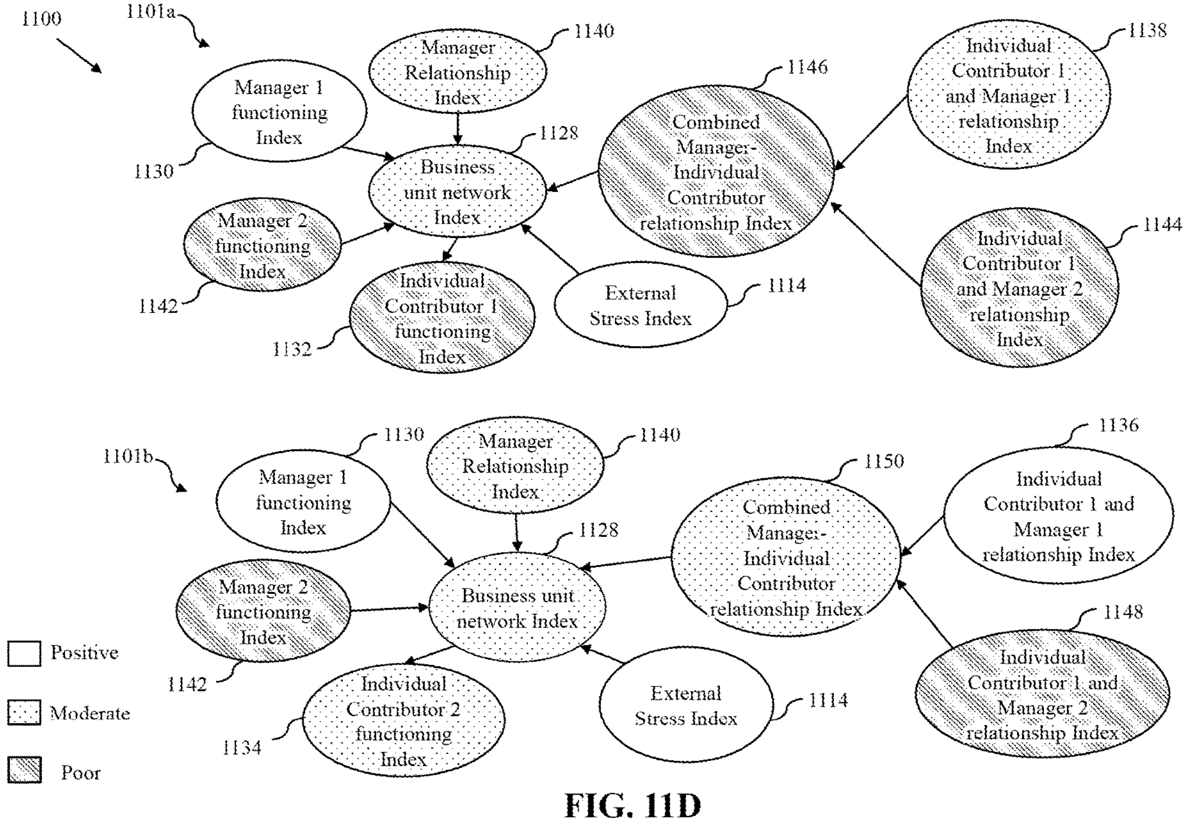
Figure 11E:
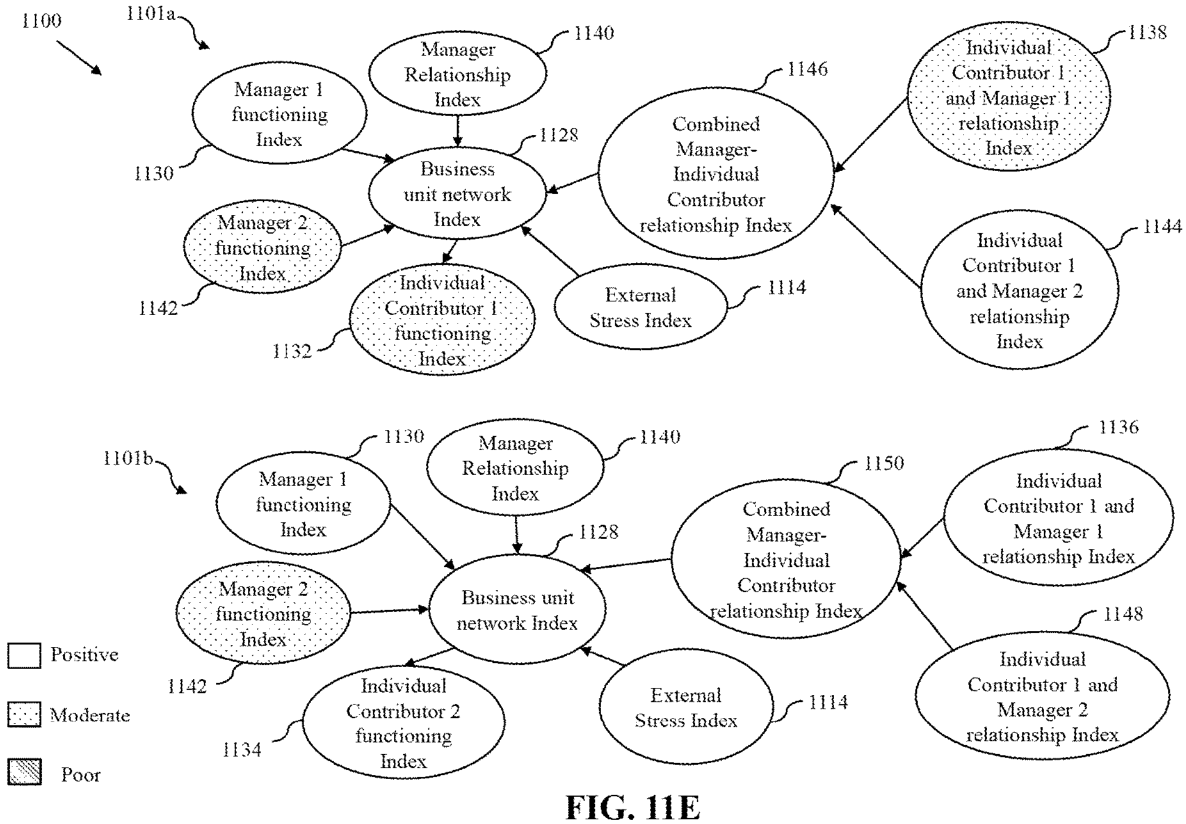

FIGS. 11D-11E, collectively, represent facilitating online therapeutic services to the business unit, in accordance with an embodiment of the disclosure. In the embodiment, the manager-2's social emotional functioning is impacting the relationships with coworkers. Further, the individual contributor-1 and the individual contributor-2 gets impacted by the manager-2's issue. The individual contributor-1 appears to have additional concerns due to frequent interactions. The issue is severe and quick improvement is prioritized. Each individual contributor or employee in a business unit (or business group) or individual working with a business or group, may have their performance viewed against a separate business unit network or subnetwork. For example, see scenario 1101*a* and 1101*b*, two different views both related to business unit 1128. In a scenario 1101*a*, of FIG. 11D, generation of the business unit network index 1128, for the individual contributor-1, is shown. The business unit network index 1128, for the individual contributor-1, is generated based on the manager-1 functioning index 1130, a manager-2 functioning index 1142, the individual contributor-1 functioning index 1132, the external stress index 1114, a manager relationship index 1140, and a combined manager-individual contributor relationship index 1146. The combined manager-individual contributor relationship index 1146, for the individual contributor-1, is generated based on the individual contributor-1 and the manager-1 relationship index 1138, and an individual contributor-1 and manager-2 relationship index 1144. In a scenario 1101*b*, of FIG. 11D, generation of the business unit network index 1128, for the individual contributor-2, is shown. The business unit network index 1128, for the individual contributor-2, is generated based on the manager-1 functioning index 1130, the manager-2 functioning index 1142, the individual contributor-2 functioning index 1134, the external stress index 1114, the manager relationship index 1140, and a combined manager-individual contributor relationship index 1150. The combined manager-individual contributor relationship index 1150, for the individual contributor-2, is generated based on the individual contributor-2 and the manager-1 relationship index 1136 and an individual contributor-2 and manager-2 relationship index 1148. Furthermore, the data related to the business unit is received, and the set of interventions are identified. The set of interventions include the manager-2 psychotherapy, leadership strategy training, and individual contributor-1 psychotherapy.

Further, a set of online therapeutic services related to the set of interventions are recommended. The set of online therapeutic services include four psychotherapy sessions for the manager-2, two leadership strategy sessions with all managers, and four psychotherapy sessions for individual contributor-1. Furthermore, the response to the set of plans is monitored over time. The response includes partial response from the manager-2 and individual contributor-1, and full response from the individual contributor-2. Based on the response, the functioning indexes improves as shown in FIG. 11E. As shown in scenario 1101*a* of FIG. 9E, the manager-2 functioning index 1142, for the individual contributor-1, improves from poor to moderate, the individual contributor-1 functioning index 1132 improves from poor to moderate, the individual contributor-1 and manager-2 relationship index 1144 is improved from poor to positive, and the combined manager-individual contributor relationship index 1146, for the individual contributor-1, improves from moderate to positive. As shown in scenario 1101*b* of FIG. 9E, the manager-2 functioning index 1142, for the individual contributor-2, improves from poor to moderate, the individual contributor-2 functioning index 1134 improves from moderate to positive, the individual contributor-2 and manager-2 relationship index 1148 improves from poor to positive, and the combined manager-individual contributor relationship index 1150, for the individual contributor-2, is improving from moderate to positive. Subsequently, the business unit network index 1128, for the individual contributor-1 and the individual contributor-2, is improved from moderate to positive. Further, the revised online therapeutic services include continuing of the psychotherapy.

Figure 11F:
Figure 11F:
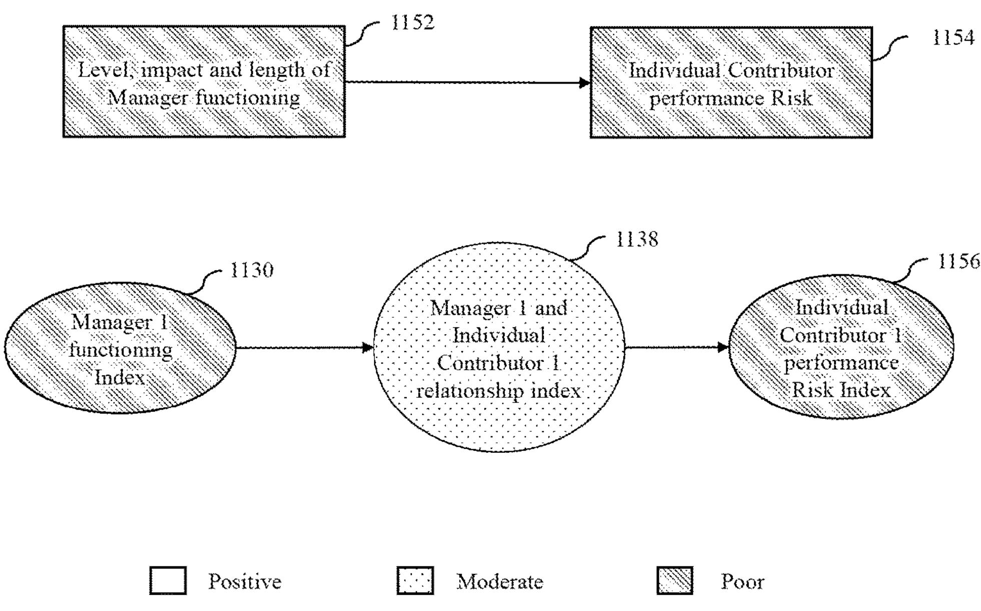
Figure 11G:
Figure 11G:
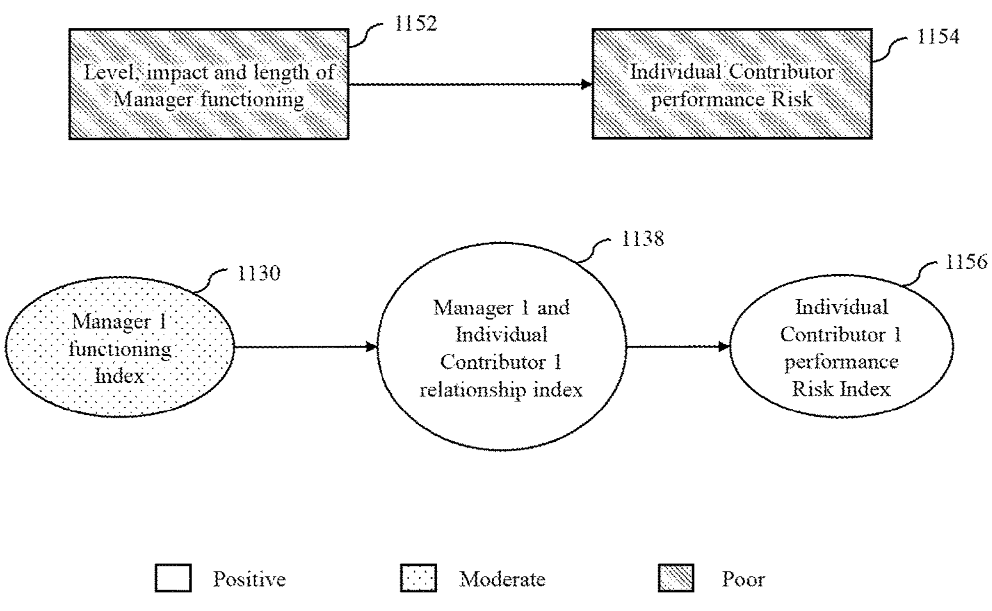

FIGS. 11F-11G, collectively, yet another exemplary embodiment for facilitating online therapeutic services to the business unit, in accordance with an embodiment of the disclosure. In the embodiment, after missing revenue targets the last 3 quarters, and an inability to partner effectively with a former salesperson that is poached by a competitor, the manager-1 is in a poor mental state and ineffective in leading sales staff. The individual contributor-1 may join and replace the former colleague this quarter. The level, impact and length of manager functioning 1152 leads to an individual contributor performance risk 1154. The set of interventions are identified based on analysis of the data of the business unit. The set of interventions include manager-1 psychotherapy, and manager-1 sales management training.

Further, the set of online therapeutic services for execution of the set of interventions are recommended. The set of online therapeutic services include four psychotherapy sessions with manager-1, and two sales management training sessions with the manager-1. The response related to the set of plans is monitored over time. The response includes partial response from the manager-1, and full response for manager-individual contributor relationship. Based on the response, the functioning index improves as shown in the FIG. 11G, the manager-1 functioning index 1130 improves from poor to moderate, the manager-1 and individual contributor-1 relationship index 1138 improves from moderate to positive, and an individual contributor-1 performance risk index 1156 improves from poor to positive. Further, the revised online therapeutic services include continuing with manager-1 mental health support.

The distance, velocity and efficiency calculations can be used for various practical purposes and applications of the invention to deliver therapeutic services. Some examples follow. Specifically, systems and methods to provide automatically a statistically valid basis for choice of mode of online therapeutic service delivered are described below. Also, systems and methods to provide automatically a statistically valid basis for the order of delivery of multiple online therapeutic services is described. Both systems can automatically assign specific service providers through a statistically valid comparison of effect sizes using the indexes described elsewhere.

One embodiment searches for stored data gathered from families, and automatically matches or "pairs" each family with another that is highly similar, before delivering services to either family.

Families are ranked as similar to each other according to a weighted combination of clinically relevant attributes, with weights varying according to the relevant importance of that attribute in context. These attributes are stored in an attributes database in accessible computer memory.

Attributes used for similarity-matching to identify matches or pairs include, but are not limited to:

Age, gender, symptoms, and symptom severity, for the "primary child of concern";

An original, pre-treatment Family Network Index score;

Weighted components of the Family Network Index, which include all available individual and pairwise relationship index values, along with the weights assigned to each to generate the Family Network Index;

Demographic facts about the family, including address, number of children in the home and their age and gender, whether the parents are separated or divorced, whether the biological mother or some other adult is the primary caregiver, which individual, if any, is identified as the "primary child of concern";

- Clinical facts about family members, such as which members of the family are suffering impairing mental health symptoms, and how severe their symptoms are;
- Other medical conditions, including chronic and terminal illnesses, and their severity, and any recent hospitalizations, and which family members have them; and
- Recent severe stressors to the family, such as job loss, current unemployment, witnessing or being the victim of a violent crime, divorce, loss of a relative, loss of a parent or child, and to whom the stress applies.

Pairs of similar families are then automatically separated into two groups or sets, with one from each matched pair assigned to each set or group. Information about each family in the set or group can be stored in relational databases.

In one use of these matches or pairing, all families within group1 are automatically assigned and receive one mode of online therapeutic service, while the families within group2 are automatically assigned and receive a different, alternative mode of online therapeutic service.

For example, an individual in each family may be suffering from anxiety potentially related to trauma. Each affected individual in the first group of families automatically receives a standard course of cognitive behavioral therapy (CBT). Each affected individual in the second group of families automatically receives a standard course of eye movement desensitization and reprocessing (EMDR). Then results can be compared. To give another example, clinical depression of a certain severity can be treated by medication, or by talk therapy. A head-to-head comparison of the two methods for efficacy is only valid when the individuals receiving services are closely matched for severity and duration of symptoms, comorbidities, etc.

In a second use of this matching or pairing, both groups of families receive the same two (or more) modes of therapeutic service. The first group of families receives the two (or more) modes of therapeutic service "simultaneously"—that is, during the same overlapping time interval (whether both are delivered to one individual, or the services are provided to two or more individuals in the family). The second group of families is assigned the same modes of therapeutic service in "seriatim"—that is, starting the second service only after the first service is complete. For example, a child may have school refusal disorder, and the mother clinical levels of anxiety and depression. Both could be treated during an overlapping time interval with online therapy, or the child could be treated first, and then the mother, with the same therapeutic technique.

In a third use of this matching or pairing, both groups of families receive the same two (or more) modes of therapeutic service seriatim, where one course of treatment will be completed before the next begins. The two sets or groups receive the same therapeutic services, but in a different order. For example, a child may have school refusal disorder, and the mother clinical levels of anxiety and depression. The child could be treated first, until certain progress is made, and then the mother, or the mother treated first, until certain progress is made, and then the child.

In each of the above embodiments, after some time interval during which recommended services are delivered, new individual index and pairwise index values are recalculated, and a new Family Network Index generated. Improved family wellness, as measured by the Family Network Index metrics of distance, velocity, and efficiency, enables better results for automated recommendation and online delivery of specific services to future families.

In each of the above embodiments, the use of matched-pairs to generate two groups for comparison greatly increases the power of effect size comparisons between two groups. Once the effect size, as measured by one or more of the Family Network Index metrics, and the group size (total number of families) reach a certain level, statistically significant difference between the two treatment groups are automatically detected.

In a first embodiment above involving two alternative modes of treatment, once statistically significant results are observed, the server automatically recommends to future families the more effective mode and delivers it online.

In a second embodiment, involving comparison between simultaneous and seriatim delivery of two or more therapeutic services, once statistically significant results are observed, the server automatically recommends whether simultaneous or seriatim delivery is superior and delivers the services online in that form.

In a third embodiment, involving comparison between alternative order of delivery for two or more therapeutic services delivered seriatim, once statistically significant results are observed, the server automatically recommends the superior order and delivers them online in that order.

Distance, velocity and efficiency can be used for in other systems such as a system with for rigorous quality control of individual providers with continual process improvement in online care delivery is described below In one embodiment, a "provider client group" is automatically generated, consisting of families all of whom contain one or more individuals who received therapeutic services online from a particular online service provider. The provider may be a doctor, therapist, marriage counsellor, coach, or other type of service provider. (Note that because one family is often served by many providers, families are not uniquely assigned to one provider client group).

A second, "provider benchmark group" is then created automatically, by creating matched pairs, matching each family in the provider client group with a highly-similar family that received online services of the same type, but which did not receive any services from the provider being evaluated.

Families are paired as similar according to a weighted combination of clinically relevant attributes, with weights varying according to the relevant importance of that attribute in context,

- Age, gender, symptoms, and symptom severity, for the "primary child of concern";
- An original, pre-treatment Family Network Index score;
- Weighted components of the Family Network Index, which include all available individual and pairwise relationship index values, along with the weights assigned to each to generate the Family Network Index;
- Demographic facts about the family, including identification, address, number of children in the home and their age and gender, whether the parents are separated or divorced, whether the biological mother or some other adult is the primary caregiver, which individual, if any, is identified as the "primary child of concern";
- Clinical facts about other family members, such as which members of the family are suffering impairing mental health symptoms, and how severe their symptoms are;
- Other medical conditions, including chronic and terminal illnesses, and their severity, and any recent hospitalizations, and which family members have them; and
- Recent severe stressors to the family, such as job loss, current unemployment, witnessing or being the victim of a violent crime, divorce, loss of a relative, loss of a parent or child, and to whom the stress applies.

These attributes are stored separately in an attributes database, or together with the set data.

In addition, to create matched family pairs for the provider client group and provider benchmark group, automated confirmation is performed that the benchmark group family received approximately the same modes and duration of therapeutic services as the provider group family, and had comparable demographics, so that the most accurate possible head-to-head comparison of individuals receiving treatment can be made.

The use of matched-pairs to generate two groups for comparison greatly increases the power of effect size comparisons between two groups. Once the effect size, as measured by one or more of the Family Network Index metrics, and the group size (total number of families) reach a certain level, statistically significant difference between the two treatment groups are automatically detected.

The system automatically compares the observed effect sizes within the provider client group to the effect sizes within the provider benchmark group, using the Network Family Index and individual and pairwise relationship indexes as calculated prior to delivery of therapeutic services, and after delivery of therapeutic services.

The Family Network Index metrics of difference or distance, velocity, and efficiency are used as the basis for these comparisons.

In addition, the Family Network Index components, consisting of weighted individual and pairwise relationship indexes, may also be compared.

In one embodiment, if an individual provider's client group performance is worse than their provider's benchmark group performance to a statistically significant degree, future families with similar attributes to those in the groups will automatically be assigned to alternative service providers with superior performance. A server system as described elsewhere may be used to detect statistically significant degrees of performance variation.

Providers performing well below their benchmark may be replaced, and families automatically assigned to alternative providers with better performance. In the alternative, automatic assignment of families to the low-performing provider may in future be limited to only a subset of families with distinct attributes where the provider's performance was adequate when measured against the matched pairs with those same attributes in the benchmark group. For example, a therapist may perform poorly with children who have diagnosed oppositional defiant disorder, but do well when working with children who have diagnosed anxiety, so in future automated routing of families will be limited to those containing a child with anxiety.

In addition, video sessions with patients, and other session materials from a poorly-performing provides, may be analyzed in an automated fashion, using AI techniques, to determine why their performance is lagging, with subsequent attempts made to retrain that provider.

A Provider may be given a period of time to demonstrate improved performance. Their post-retraining performance can be measured using a new provider client group, containing only client families to whom they have provided services since retraining, matched to a new provider benchmark group.

In one embodiment, if an individual provider's group-level performance is better than their benchmark to a statistically significant degree for individuals or families with certain attributes, future families with similar attributes will automatically be assigned to that therapist.

In one embodiment, it will become clear which therapists have outstanding performance treating a very specific symptom or constellations of symptoms, and the automated quality-control process described about will automatically direct future clients to the best possible therapist for them, which will significantly boost overall performance and client satisfaction.

In addition, Video sessions with patients and other session materials from outstanding practitioners will be analyzed in automated fashion, using AI techniques, to identify best practices that can be taught to and adopted by other providers, thereby improving their performance as well.

Quality control as described above will be performed on a regular basis, with frequency of perhaps once every ninety days, as the only constraint is to create provider client groups that reflect the latest techniques for determining modes and order of services delivered, and are sufficiently large (in terms of total number of families receiving care from a provider in that time interval) to have sufficient power to detect meaningful effect sizes.

One embodiment is a computerized system to provide on-line therapeutic services for measurably improving group functioning. The computerized system comprising: data input devices, wherein time-stamped wellness profile data of individuals and time-stamped data relating specifically to the relationship between pairs of individuals are acquired; interface equipment, wherein the wellness profile data of individuals and the relationship data about pairs of individuals from the data input devices is received; a server system, operably connected to the interface equipment, wherein the wellness profile data of individuals and relationship data about pairs of individuals from the data input devices is gathered; a processor, operably connected to the server system, configured to resolve the gathered wellness profile data of individuals and the gathered relationship data about pairs of individuals into separate but linked categories of a group; data storage, operably connected to the processor, wherein the gathered data is stored by group; a system programmed to access the data storage and generate output at requested times, derived automatically through processing a group's individual and relationship data, including programming to generate a first index, a second and subsequent indexes, as a deterministic function of the available individual and pairwise-relationship data stored as a group or family network. The computerized system can be further programmed to calculate:

- a distance between indexes;
- a velocity or rate of change of an index derived by dividing by time elapsed a difference between two instances of the index;
- an efficiency metric derived by dividing, by a measure of the total expenditure of resources during the time elapsed between a calculation of two indexes, by the difference between those two indexes; and
- recommendations for delivery of additional resources to contribute to improvements in the index.

Finally, the system many include computers connected to a network to deliver, in response to the recommendation, on-line services to individuals within groups; wherein a change of group function is measured by successive indexes.

In another embodiment of the system, the data input devices comprise mobile phones, tablets and laptops.

In another embodiment of the system the data input devices comprise a first set of data input devices for the wellness profile data of individuals and a second set of data input devices for the relationship data between two individuals.

In another embodiment of the system, audio/video interviews of individuals are captured and stored and the data input devices comprise audio/video processors for extracting audio and video that is relevant to the wellness profile data of individuals.

In another embodiment of the system, audio/video interviews of individuals are captured and stored, and the data input devices comprise computers processors for extracting audio and video that is relevant to pairwise relationships wherein the extracting uses one or more of: machine learning, artificial intelligence and rules-based decision making.

In another embodiment of the system, the interface equipment is network equipment allowing communication between the data input devices and the server system over a network.

In another embodiment of the system, a group is one of: a family, network, team, family network and functional network.

In another embodiment of the system, the wellness profile data is converted to an impact score by the processor.

In another embodiment of the system, the impact scores are stored by group category.

In another embodiment of the system, the separate but linked categories constituting a group.

In another embodiment of the system, the index takes the form of one or more of the following types: numerical, nominal, ordinal, ratio and categorical form.

In another embodiment of the system, the measure of the total expenditure of resources comprises one of: services, medicines or modalities.

In another embodiment of the system, the system is further programmed to calculate the index by using a deterministic formula.

In another embodiment of the system, the programmed system is programmed to use weights, wherein weights are applied to each raw score to generate an index.

In another embodiment of the system, the computers are connected to the internet and are enabled to provide services using for real-time audio and video.

One embodiment is a computerized method to provide on-line mental healthcare and other therapeutic services to measurably improve the functioning of a group of individuals. The computerized method comprising the following steps: receiving, from data input devices, information on a group of individuals including identities, raw data for wellness profile of individuals and data relating to relationships between individuals in the group; gathering the wellness profile data of individuals and the relationship data between individuals in the group; processing and scoring, with a computer server, the wellness profile data and relationship data; organizing the scored data into group categories; storing the organized group category data in memory; generating, using a computer system, output including a first index, wherein the first index is automatically derived through processing a groups' stored group category data using a deterministic formula; generating, using the index, the computer system, and a program, recommendations for healthcare services; providing, using computers, on-line healthcare services to the group in accordance with recommendations; calculating, after on-line healthcare services have been rendered, a second index, a distance between indexes, a velocity, an efficiency of services, and a recommendation as to services to be rendered; determining, based up the calculations, whether the group function has measurably improved; providing, using the computers, additional on-line healthcare services until a threshold amount of measurable improvement has been reached.

In another embodiment of the computerized method, the data relating to relationships between individuals in a group relates to two or more relationships.

In another embodiment of the computerized method, the index data relating to relationships between individuals in the group relates three or more relationships.

In another embodiment of the computerized method, the scoring generates a numerical score for the wellness profile of each individual in the group.

In another embodiment of the computerized method, the providing of on-line healthcare services includes one on one therapy with an individual.

In another embodiment of the computerized method, the providing of on-line healthcare services includes group therapy sessions.

Another embodiment includes a computerized method to measure the functioning of a group of individuals and provide on-line mental healthcare and other therapeutic services both on-line and off-line to measurably improve the functioning of the group of individuals. The computerized method comprising the steps of:

receiving, from data input devices, identification of individuals in a group and data about individuals from one of: questionnaire responses and interviews; sorting, using a computer processor, the received data into records identified with an individual and records identified with a pairwise relationship between individuals in the group;

processing the sorted data identified with individuals and pairwise relationships into time stamped numerical scores for individuals and for pairwise relationship;

assigning a unique group identification; computer generating a timestamped group numerical score associated with the unique group identification; storing, in computer memory, the timestamped group numerical score associated with the unique group identification;

making recommendations automatically, using the stored group numerical score, for on-line therapeutic services;

arranging to provide on-line therapeutic services; evaluating the effectiveness of the provided on-line therapeutic services by comparing the stored timestamped group numerical score with a second timestamped group numerical score which is computer generated later in time and determining if there is a measurable improvement to the functioning of the group. Repeating the steps of the computerized process as necessary to until the performance of the group improves to acceptable level.

In another embodiment of the computerized method, the step of receiving comprises receiving data from both questionnaire responses and interviews.

In another embodiment of the computerized method, the steps further comprise the step of timestamping the received data about individuals.

In another embodiment of the computerized method, the step of computer generating a timestamped group numerical score comprises calculating, using weights, the timestamped group numerical score, wherein some timestamped numerical scores for individuals and some timestamped numerical scores for pairwise relationships are weighted differently.

In another embodiment of the computerized method, the step of making recommendations comprises choosing a treatment plan for on-line therapeutic services using: (i) the time stamped individual numerical scores for individuals, (ii) the timestamped numerical score for pairwise relationships and (iii) the timestamped group index.

In another embodiment of the computerized method, the step of making recommendation comprises the step of triaging based on: (i) the time stamped individual numerical scores for individuals, (ii) the timestamped numerical score for pairwise relationships and (iii) the timestamped group index.

In another embodiment of the computerized method, the step of making recommendations comprises prioritizing treatment by analyzing: (i) the time stamped individual numerical scores for individuals, and (ii) the timestamped numerical score for pairwise relationships.

In another embodiment of the computerized method, the step of making recommendations comprises prioritizing treatment for an individual within the group with a highest time stamped individual numerical score.

In another embodiment of the computerized method, the method further comprising the step of determining improvement of group function by calculating the difference between the timestamped group numerical score at different points in time.

In another embodiment of the computerized method, the method steps further comprising the step of comparing the timestamped group numerical score of one group against a timestamped group numerical score of a second group for allocating on-line therapeutic services across groups.

The disclosed embodiments encompass numerous advantages. The disclosure provides various methods and systems for evaluating performance and delivering therapeutic services of a group of entities. The disclosed evaluation methods and systems may conserver resources and help to reduce medical treatment cost. The disclosed evaluation methods and system helps to provide an efficient way of monitoring functioning of the group of entities and providing efficient plans/treatments to the group of entities so that the functioning of the group improves. The disclosed methods and systems facilitate end-to-end administration of the performance evaluation and all the components of the performance evaluation activity for the group of entities. Further, all the steps of the performance evaluation activity are performed automatically. Additionally, the performance evaluation activity may be preconfigured for dynamic 'one-click' administration during the evaluation.

A person of ordinary skill in the art will appreciate that embodiments and scenarios of the disclosed subject matter may be practiced with various computer system configurations, including cloud computing, multi-core multiprocessor systems, minicomputers, mainframe computers, computers linked or clustered with distributed functions, as well as pervasive or miniature computers that may be embedded into virtually any device. Further, the operations may be described as a sequential process, however some of the operations may in fact be performed in parallel, concurrently, and/or in a distributed environment, and with program code stored locally or remotely for access by single or multiprocessor machines. In addition, in some embodiments, the order of operations may be rearranged without departing from the spirit of the disclosed subject matter.

Techniques consistent with the disclosure provide, among other features, systems and methods for evaluating performance of the group of entities. While various embodiments of the disclosed performance evaluation systems and methods have been described above, it should be understood that they have been presented for purposes of example only, and not limitations. It is not exhaustive and does not limit the disclosure to the precise form disclosed. Modifications and variations are possible in light of the above teachings or may be acquired from practicing of the disclosure, without departing from the breadth or scope.

While various embodiments of the disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims. Further, unless stated otherwise, terms such as "first" and "second" are used to arbitrarily distinguish between the elements such terms describe. Thus, these terms are not necessarily intended to indicate temporal or other prioritization of such elements.

The various illustrative logical blocks and modules described in connection with the embodiments disclosed herein can be implemented or performed by a machine, such as a processor. A processor can be a microprocessor, but in the alternative, the processor can be a controller, microcontroller, or state machine, combinations of the same, or the like. A processor can include electrical circuitry configured to process computer-executable instructions. In another embodiment, a processor includes an application specific integrated circuit (ASIC), a field programmable gate array (FPGA) or other programmable device that performs logic operations without processing computer-executable instructions. A processor can also be implemented as a combination of computing devices, e.g., a combination of a digital signal processor (DSP) and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A system to automatically assign, through a statistically valid comparison of effect sizes, modes of online therapeutic services to be delivered to a group of individuals, comprising:

a database having stored data about groups of individuals, wherein each group is identified by an identification and the data includes attributes of each group and a group index, wherein the attributes of each group includes demographics and the group index comprises a measure of the relative optimization of the group which indicates group performance;

a server system, operably connected to the database, programmed to:

search the database to match a first group with a second group that have similar attributes, wherein groups are ranked similar according to weighted combination of clinically relevant attributes;

separate matched groups into two sets, first set and second set, wherein one of the matched groups is placed into each set;

deliver, using network equipment, a first mode of online therapeutic service to the first set and an alternative mode of online therapeutic service to the second set;

calculate a group index for each group after delivery of the online therapeutic services;

determine, based on the calculated group indexes and the stored group indexes, whether the first mode or the alternative mode of online therapeutic service caused an improvement in the group index of a group exceeding an effect size; and recommend and deliver, through a network, to a third group the mode of online therapeutic service which caused the improvement.

2. The system of claim 1 wherein the server system is further programmed to:

divide the improvement in the group index of a group by an amount of time elapsed between group index calculations to arrive at a rate of change of the group index.

3. The system of claim 1 wherein the server system is further programmed to:

divide the improvement in the group index of a group by an amount of time elapsed while the group received delivered therapeutic services to arrive at a rate of change of the group index.

4. The system of claim 1 wherein the server system is further programmed to:

determine a time elapsed between the calculation of the stored group index and the calculated group index;

divide an amount of resources expended during the time elapsed by the improvement in the group index of a group.

5. The system of claim 1 wherein the server system is further programmed to:

determine a time elapsed between the calculation of a group index prior to the group receiving delivered therapeutic services and after receiving the delivered therapeutic services;

divide an amount of resources expended during the time elapsed by the improvement in the group index of a group.

6. The system of claim 1 wherein the delivered online therapeutic services comprise two types of services, simultaneously and in seriatim, and wherein the first mode is to deliver simultaneously and the alternative mode is to deliver in seriatim.

7. The system of claim 1 wherein the online therapeutic services comprise two different orders of delivery, the first mode is a reverse order of delivery of service from the alternative mode.

8. A computerized method for automatically assigning, through a statistically valid comparison of effect sizes, modes of online therapeutic services to be delivered to a group of individuals, comprising:

identifying groups of individuals;

storing group attribute information for identified groups in a database wherein the stored group attribute data includes demographics;

storing group indexes for identified groups, wherein the group indexes comprises a measure of the relative optimization of the identified group which indicates group performance;

accessing the stored group attribute information;

matching, using a computer, a first group with a second group having similar attributes, using the stored group attribute information, wherein groups are categorized as similar according to weighted combination of clinically relevant attributes;

separating, using the computer, matched groups into two sets, a first set and a second set, wherein one of the matched group is placed into each set;

delivering, using a network, a first mode of online therapeutic service to the first set and an alternative mode of online therapeutic service to the second set;

calculating a group index for each group after delivery of the online therapeutic services;

determining, based on the calculated group indexes and the stored group indexes, whether the first mode or the alternative mode of online therapeutic service caused an improvement in the group index of a group exceeding a threshold amount; and delivering, through a network, to a third group the mode of online therapeutic service which caused the improvement.

9. The computerized method of claim 8 wherein the calculated group index and the stored group index are timestamped, the method further comprising:

computing, using the calculated group index and stored group index, an amount of improvement in the group index of a group;

dividing the improvement of the group index by an amount of time elapsed between the calculated group index and stored group index to arrive at a rate of change of the group index;

ascertaining, using the rate of change, whether the first mode or alternative mode of online therapeutic services caused a greater rate of change of the group index.

10. The computerized method of claim 8 further comprising:

determining an amount of time elapsed while a group was receiving delivered online therapeutic services;

computing, using the calculated group index and stored group index, an amount of change in the group index of a group;

divide the amount of change in the group index of a group by the determined amount of time elapsed to arrive at a rate of change of the group index.

11. The computerized method of claim 8 wherein the calculated group index and the stored group index are timestamped, the method further comprising:

determine a time elapsed between the calculation of the stored group index and the calculated group index for the same group;

computing, using the calculated group index and stored group index, an amount of change in the group index of a group;

divide an amount of online therapeutic services expended during the time elapsed by the amount of change in the group index of a group.

12. The computerized method of claim 8 further comprising:

computing, using the calculated group index and stored group index, an amount of change in the group index of a group;

ascertaining whether the computed amount of change in the group index of a group is a positive change or a negative change;

determine, if a positive change, which mode of online therapeutic service provided the positive change.

13. The computerized method of claim 8 further comprising:

computing, using the calculated group index and stored group index, an amount of change in the group index of a group;

determining an amount of time elapsed while a group was receiving delivered online therapeutic services;

dividing the amount of change by the determined time elapsed resulting in velocity of change of a group index;

determine whether the first mode or the alternative mode of online therapeutic services resulted in a greater velocity of change.

14. The computerized method of claim 8 wherein the delivered online therapeutic services comprise two types of services, simultaneously and in seriatim, and wherein the first mode is to deliver simultaneously and the alternative mode is to deliver in seriatim.

15. The computerized method of claim 8, wherein the online therapeutic services comprise two different chronological orders of delivery, the alternative mode is a reverse order of delivery of service from the first mode.

16. A computerized method for automatically assigning based on quantifiable performance online therapeutic service providers for individuals or families and delivering online therapeutic services, comprising:

generating, using a computer, a provider client group of families served by a provider being evaluated, wherein families who contain individuals who received therapeutic services from the provider are included in the group;

storing data regarding the generated provider client group of families in a first database;

accessing, using a processor, an attributes database containing attributes associated with families including family structure;

automatically matching families in the provider client group with other families using a weighted combination of clinically relevant attributes;

generating a provider benchmark group comprised of matched families who have received similar therapeutic services but did not receive any services from the provider being evaluated;

computing a pre-treatment family network index score and a post-treatment family network index score wherein the network index scores represent relative optimization of a family which indicates family performance;

calculating provider performance as a difference between the pre-treatment family index score and the post-treatment family index score for two or more families;

detecting better provider performance between families in the provider client group and families in the provider benchmark group;

automatically assigning providers with the better performance in the provider client group as a whole, or a distinct subset thereof, to subsequent families with similar attributes; and delivering, using network equipment, online therapeutic services based on the assigned providers.

17. The computerized method of claim 16 wherein the provider performance for a provider is measurably inferior compared with the provider performance of other service providers, the method further comprising providing training to the provider having the measurably inferior provider performance.

18. The computerized method of claim 16 further comprising examining, using a processor, treatment methodologies used by providers having better provider performance to use in training other providers.

19. The computerized method of claim 16 wherein some service providers that are found to perform better with families having certain attributes, the method further comprising:

determining, using a processor, whether there is a correlation between a provider's performance and the attributes of a family;

wherein the step of automatically assigning providers further comprises using the correlation at least as a factor in assigning providers to families.

20. The computerized method of claim 16 further comprising:

automatically analyzing provider performance in treating a particular ailment;

wherein the step of automatically assigning providers further comprises using provider performance in treating an ailment at least as a factor in assigning providers.

* * * * *